(12) United States Patent
Shi et al.

(10) Patent No.: US 11,643,405 B2
(45) Date of Patent: May 9, 2023

(54) COMPOUND FOR TREATMENT OR PREVENTION OF LIVER DISEASES

(71) Applicant: JIANGSU ATOM BIOSCIENCE AND PHARMACEUTICAL CO., LTD., Suzhou (CN)

(72) Inventors: Dongfang Shi, Fremont, CA (US); Changjin Fu, Suzhou (CN); Xi Cheng, Suzhou (CN); Weiwei Gong, Suzhou (CN); Jie Gu, Suzhou (CN); Pengfei Li, Suzhou (CN); Min Zhang, Suzhou (CN); Yan Yang, Suzhou (CN); Wenqing Jin, Suzhou (CN)

(73) Assignee: JIANGSU ATOM BIOSCIENCE AND PHARMACEUTICAL CO., LTD., Suzhou (CN)

( * ) Notice: Subject to any disclaimer, the term of this patent is extended or adjusted under 35 U.S.C. 154(b) by 0 days.

(21) Appl. No.: 16/973,443

(22) PCT Filed: Jun. 5, 2019

(86) PCT No.: PCT/CN2019/090135
§ 371 (c)(1),
(2) Date: Dec. 9, 2020

(87) PCT Pub. No.: WO2019/233440
PCT Pub. Date: Dec. 12, 2019

(65) Prior Publication Data
US 2021/0246126 A1 Aug. 12, 2021

(30) Foreign Application Priority Data
Jun. 9, 2018 (CN) .......................... 201810590506.0

(51) Int. Cl.
| | |
|---|---|
| *C07D 407/04* | (2006.01) |
| *A61P 1/16* | (2006.01) |
| *A61K 9/00* | (2006.01) |
| *A61K 9/08* | (2006.01) |

(52) U.S. Cl.
CPC .............. *C07D 407/04* (2013.01); *A61P 1/16* (2018.01); *A61K 9/0053* (2013.01); *A61K 9/08* (2013.01)

(58) Field of Classification Search
CPC ............................ C07D 407/04; A61K 31/357
See application file for complete search history.

(56) References Cited

U.S. PATENT DOCUMENTS 6,218,369 B1 * 4/2001 Bombardelli .......... A61K 36/28
514/34

FOREIGN PATENT DOCUMENTS

WO    WO 01/07034 A1 *    2/2001

OTHER PUBLICATIONS

Ekinci et al., Carbonic anhydrase inhibitors: in vitro inhibition of a isoforms (hCA I, hCA II, bCA III, hCA IV) by flavonoids, Journal of Enzyme Inhibition and Medicinal Chemistry, 28 (2): 283-288 (2013).*
Gazak et al., Molecular mechanisms of silybin and 2,3-dehydrosilybin and antiradical activity—role of individual hydroxyl groups, Free Radical Biology & Medicine, vol. 46, Issue 6, pp. 745-758 (2009).*
PubChem CID 129012666 (Jul. 31, 2017).*
PubChem CID 20646574 (Dec. 5, 2007).*

* cited by examiner

*Primary Examiner* — Deepak R Rao
(74) *Attorney, Agent, or Firm* — CBM Patent Consulting, LLC

(57) ABSTRACT

The invention discloses compounds for treatment or prevention of liver diseases. The compounds are compounds represented by a formula (I) or (II), optical isomers or pharmaceutically acceptable salts of the compounds. The compounds and optical isomers or pharmaceutically acceptable salts of the compounds can be applied to preparation of drugs for treatment or prevention of liver diseases.

8 Claims, 3 Drawing Sheets

COMPOUND FOR TREATMENT OR PREVENTION OF LIVER DISEASES

TECHNICAL FIELD

The invention belongs to the field of medicinal chemistry and specifically relates to a class of compounds for treatment or prevention of liver diseases.

BACKGROUND OF THE INVENTION

With the continuous improvement of people's lifestyle and the changes of diet structure, long-term overnutrition can easily lead to the occurrence of Non-Alcoholic Fatty Liver Disease (NAFLD). According to its pathological process, NAFLD can be divided into (Non-Alcoholic Simple Fatty liver (NAFL) and Non-Alcoholic Steatohepatitis (NASH), which potentially lead to related liver cirrhosis and liver cancer (Fatty Liver and Alcoholic Liver Disease Groups of Branch of Hepatology of Chinese Medical Association. Guidelines for the diagnosis and treatment of nonalcoholic fatty liver disease. Chinese Journal of Hepatology, 2006, 14:161-163). NASH refers to a disease associated with changes similar to alcoholic hepatitis, such as macrovesicular steatosis, ballooning degeneration and intralobular inflammation of the liver cells and patients with no history of excessive drinking. At present, the prevalence of NAFLD in the general population is as high as 15%-20% and 76%-90% in the obese (N. Belemets, N. Kobyliak, O. Virchenko, et al. Effects of polyphenol compounds melanin on NAFLD/NASH prevention. Biomedicine and Pharmacotherapy, 2017, 88: 267-276). It is estimated that the risk of NAFLD in the global population will significantly exceed that of hepatitis B and C in the future. At the same time, NAFLD is also the main cause of chronic liver disease, so there are many related serious health problems, such as liver cirrhosis, liver metastasis, liver cancer and even death (N. Kobyliak, L. Abenavoli. The role of liver biopsy to assess non-alcoholic fatty liver disease. Reviews on Recent Clinical Trials. 2014, 9: 159-169; G. Musso, R. Gambino, M. Cassader, et al. Meta-analysis: natural history of non-alcoholic fatty liver disease (NAFLD) and diagnostic accuracy of non-invasive tests for liver disease severity. Annals of Medincine, 2011, 43: 617-649).

The etiology of NASH is closely related to metabolic syndromes such as obesity, hyperlipidemia and diabetes, but its pathogenesis is complex and has not been fully elucidated so far. One classic is a tale of two "hits" (C. P. Day, O. F. W. James. Steatohepatitis: A tale of two "hits". Gastroenterology, 1998, 114(4): 842-845). The "first hit" (development of liver steatosis) is believed to be mainly caused by insulin resistance (IR). Free fatty acids (FFA) are derived from the breakdown of surrounding fat, ingested food or new lipid production; FFA is used during oxidation, phospholipid formation and triglyceride (TG) synthesis and a dynamic balance is achieved between production and utilization of FFA in the body. Flowever, when IR occurs, the physiological and biochemical reactions regulated by the insulin-mediated signaling pathway are disturbed and its inhibitory effect on lipolysis of adipose tissue is blocked, resulting in excessive lipolysis of adipose tissue, thereby increasing the level of FFA in plasma and making formation of TG greatly exceeds the rate of conversion and clearance, which makes TG accumulate in the liver and causes the occurrence of macrovesicular steatosis of liver cells (C. Postic, J. Girard. Contribution of de novo fatty acid synthesis to hepatic steatosis and insulin resistance: lessons from genetically engineered mice. The Journal of Clinical Investigation, 2008, 118(3): 829-838). The "second hit" (fatty inflammation) is due to the excessive production of reactive oxygen species (ROS) and the reduction of antioxidant defense mechanisms which lead to oxidative stress. A large number of FFA produce ROS during metabolic processes, the ROS undergo lipid peroxidation with the phospholipid bilayer of the cell membrane to generate active metabolites such as malondialdehyde and 4-hydroxynonenol, which cause damage to the structure and function of the cell membrane; at the same time, ROS can also cause mitochondrial damage, the latter can lead to damage to secondary mitochondrial fatty acid $\beta$ oxidation pathway and further promote the steotosis of liver cells, forming a vicious circle; other secondary hit factors include increase of endotoxin, iron overload and activation and overexpression of kupffer cells etc. (P Z Li, K. Fie, J Z Li, et al. The role of kupffer cells in hepatic diseases. Molecular Immunology, 2017, 85: 222-229).

At present, there is no therapeutic drug for NASH in the world. When simple lifestyle adjustment is not enough, some insulin sensitizers, weight loss drugs, antioxidants, liver protection and lipid-lowering drugs are clinically integrated into the treatment plan of NASH. However, these drugs usually have potential safety risks and insufficient efficacy, which can not meet the treatment expectations.

Obeticholic acid developed by Intercept in the United States, which is in the phase III clinical study, is a farnesoid X receptor (FXR) agonist. It can reduce the level of blood lipid through a variety of ways and reduces the accumulation of TG in the liver and the degree of oxidative stress and lipid peroxidation, but it has a significant itching allergic reaction (The Farnesoid X Receptor (FXR) Ligand Obeticholic Acid in NASH Treatment Trial (FLINT). NCT01265498. 2015) and can cause serious liver injury and death risk in high dose (FDA Drug Safety Communication: FDA warns about serious liver injury with Ocaliva (obeticholic acid) for rare chronic liver disease. Sep. 21, 2017). In addition, it was found that 3% of patients had serious cardiovascular adverse events in phase III study (Phase 3 Study of Obeticholic Acid in Patients With Primary Biliary Cirrhosis (POISE). NCT01473524. 2017). Aramchol developed by Galmed Pharmaceuticals was a new type of fatty acid-cholic acid conjugate, used in the treatment of NASH in early stage, but the results of phase Ila clinical trial shows the doseage is higher, which needed to reach 300 mg/day to significantly reduce accumulation of liver fat (R. Safadi, F M Konikoff, M. Mahamid, et al. The fatty acid-bile acid conjugate aramchol reduces liver fat content in patients with nonalcoholic fatty liver disease. Clinical Gastroenterology and Hepatology, 2014 (12): 2085-2091); GS-4997 developed by Gilead is a highly selective small-molecule apoptosis signal-regulated kinase (ASK) inhibitor, which can be used to reduce the pro-hepatic fibrosis response to ROS, although its phase II clinical results show that 43% of subjects have improved fibrosis after treatment, but the number of samples in the study is too small and the data is not compared with placebo, so there is still a lot of uncertainty in the follow-up study (Safety, tolerability and efficacy of GS-4997 alone or in combination with simtuzumab (SIM) in adults with nonalcoholic steatohepatitis (NASH) and fibrosis stages F2-F3. NCT02466516. 2015); Elafibranor developed by Genfit (France) is a PPARa/6 dual agonist, which can improve insulin sensitivity and lipid metabolism disorders and reduce inflammation. But in phase II clinical trials, it failed to reach the end point of the dispearrance proportion of steatohepatitis without exacerbation of liver fibrosis and only mild to moderate patients were evaluated to achieve the desired goal (Phase IIb study to evaluate the efficacy and safety of GFT505 versus placebo in patients with non-alcoholic steatohepatitis (NASH). NCT01694849. 2012). It can be seen that various candidate drugs that are currently in the clinical study phase are not significant in terms of efficacy and all have certain toxic side effects.

Silymarin has anti-oxidant activity and significant liver-protecting effects. By improving mitochondrial function to scavenge oxygen free radicals and reduce carbon monoxide production, it can thereby reduce the level of lipid peroxidation and achieve the effect of inhibiting hepatocyte steatosis (PF Surai. Silymarin as a natural antioxidant: an overview of the current evidence and perspectives. Antioxidants (Basel), 2015(4): 204-247); at the same time, silymarin can also be used to treat NASH comprehensively through multiple ways: it can inhibit the production of a variety of inflammatory factors, such as NF-kB, IL1, IL6, TNFα, IFN-γ and GM-CSF (A. Federico, M. Dallio, C. Loguercio. Silymarin/silybin and chronic liver disease: a marriage of many years. Molecules, 2017(22): 2); it also can alleviate or prevent the process of liver fibrosis by reducing the proliferation of stellate cells induced by platelet-derived factor (PDGF) and down-regulating the levels of type III procollagen, α-SMA and TGF-β (S. Clichici, D. Olteanu, A. Filip, et al. Beneficial effects of silymarin after the discontinuation of CCl4-induced liver fibrosis. Journal of Medicinal Food, 2016(19): 789-797). NAFLD animal models have also confirmed that silymarin has a good liver-protecting effect. Silymarin can improve symptoms and liver biochemical functions of viral chronic hepatitis. It can be seen clinically that some patients have different degrees of improvement in liver histopathology and it also has a certain effect on early liver cirrhosis.

At present, there have been clinical reports on the treatment of NASH with silymarin alone or in combination with metformin, rosiglitazone (Zhongxin Liu. The efficacy of silymarin combined with pioglitazone in the treatment of 76 subjects of non-alcoholic fatty liver disease. Chinese Journal of Clinical Gastroenterology, 2012, 24(5): 288-290; Sheling Lu. Silymarin combined with metformin in the treatment of non-alcoholic fatty liver disease. Journal of Medical Forum, 2016, 37(4): 153-154), but the preliminary efficacy is limited. There are also clinical studies of silymarin in the treatment of NAFLD. After 48 weeks of continuous treatment, the lipidation level of patients has not been significantly improved compared with placebo, but the degree of liver fibrosis has been significantly reduced (WK Chan, N. Raihan. N. Mustapha, et al. A randomized trial of silymarin for the treatment of non-alcoholic steatohepatitis. Clinical Gastroenterology and Hepatology, 2017(15): 1940-1949). However, silymarin also has problems of poor solubility, poor oral absorption and low bioavailability, which affect its clinical efficacy.

The treatment of NASH is a long-term clinical medication process, but the current drugs in clinical research stage have various problems such as unclear efficacy, big side effects and unfitness for long-term use. Therefore, the NASH market urgently needs drugs with good efficacy and low toxicity.

SUMMARY OF THE INVENTION

One object of the present invention is to provide a class of compounds with potential therapeutic or preventive effects on liver diseases on the basis of the prior art.

Another object of the present invention is to provide a use of the above compounds in the treatment or prevention of diseases.

The objects of the present invention can be achieved by the following measures:

The present invention provides compounds represented by a formula (I) or (II) and optical isomers or pharmaceutically acceptable salts thereof,

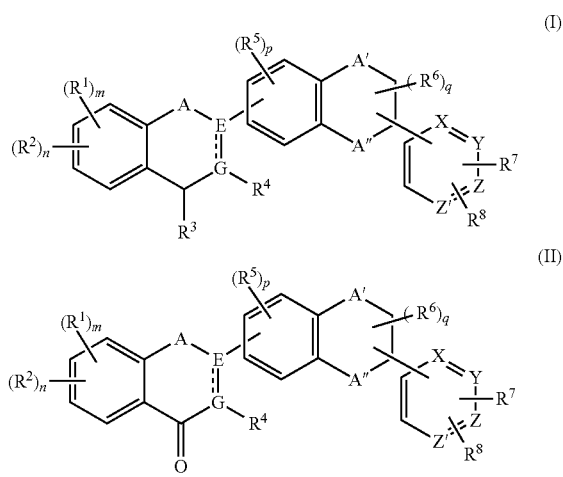

wherein,
$R^1$ or $R^2$ is each independently selected from one or more of the group consisting of hydrogen, deuterium, hydroxyl, halogen, cyano, carboxyl, $C_{1-5}$ alkyl, substituted $C_{1-5}$ alkyl, $C_{1-5}$ alkoxy, substituted $C_{1-5}$ alkoxy, $C_{1-3}$ alkylthio and substituted $C_{1-3}$ alkylthio;

$R^3$ or $R^4$ is each independently selected from the group consisting of hydrogen, deuterium, hydroxyl, amino, substituted amino, nitro, halogen, cyano, carboxyl, $C_{1-5}$ alkyl, substituted $C_{1-5}$ alkyl, $C_{1-3}$ alkoxy and substituted $C_{1-3}$ alkoxy, the substituent is selected from one or more of the group consisting of deuterium, hydroxyl, amino, nitro, halogen, cyano, carboxyl, $C_{1-3}$ alkyl and glycosyl;

$R^5$ is selected from one or more of the group consisting of hydrogen, deuterium, hydroxyl, halogen, cyano, carboxyl, $C_{1-5}$ alkyl, substituted $C_{1-5}$ alkyl, $C_{1-3}$ alkoxy, substituted $C_{1-3}$ alkoxy, $C_{1-3}$ alkylthio and substituted $C_{1-3}$ alkylthio;

$R^6$ is selected from one or more of the group consisting of hydrogen, deuterium, hydroxyl, halogen, cyano, amino, substituted amino, carboxyl, $C_{1-5}$ alkyl, substituted $C_{1-5}$ alkyl, $C_{1-3}$ alkoxy and substituted $C_{1-3}$ alkoxy, the substituent is selected from one or more of the group consisting of deuterium, hydroxyl, amino, nitro, halogen, cyano, carboxyl and $C_{1-3}$ alkyl;

$R^7$ or $R^8$ is each independently selected from the group consisting of hydrogen, deuterium, hydroxyl, halogen, amino, substituted amino, nitro, cyano, $C_{1-3}$ alkyl, substituted $C_{1-3}$ alkyl, $C_{1-3}$ alkoxy and substituted $C_{1-3}$ alkoxy, the substituent is selected from one or more of the group consisting of deuterium, hydroxyl, amino, nitro, halogen and cyano;

A is selected from the group consisting of oxygen, sulfur or CHR', R' is selected from the group consisting of hydroxyl, amino, cyano, carboxyl and substituted $C_{1-5}$ alkyl and the substituent is selected from one or more of the group consisting of deuterium, hydroxyl, amino, cyano and carboxyl;

A' or A" is each independently selected from the group consisting of oxygen, sulfur, CO and CHR, and R is selected from the group consisting of hydrogen, deuterium, hydroxyl, amino, nitro, cyano, $C_{1-5}$ alkyl and substituted $C_{1-5}$ alkyl, the substituent is selected from one or more of the group consisting of deuterium, hydroxyl, amino, nitro, carboxyl, halogen and cyano;

E or G is each independently selected from C or CH and a carbon-carbon single bond or a carbon-carbon double bond is between E and G;

X, Y, Z or Z' is each independently selected from CH or N;

m, n, p or q is 0, 1, 2 or 3;

The substituents in $R^1$, $R^2$ or $R^5$ are each independently selected from one or more of the group consisting of deuterium, hydroxyl, amino, nitro, halogen, cyano, carboxyl and glycosyl;

In the compounds represented by formula (II), A' and A" are not simultaneously selected from oxygen.

In a preferred embodiment, $R^1$ or $R^2$ is each independently selected from one or more of the group consisting of hydrogen, hydroxyl, halogen, cyano, carboxyl, $C_{1-3}$ alkyl, substituted $C_{1-3}$ alkyl, $C_{1-3}$ alkoxy, substituted $C_{1-3}$ alkoxy, $C_{1-3}$ alkylthio and substituted $C_{1-3}$ alkylthio, the substituent is selected from one or more of the group consisting of deuterium, hydroxyl, amino, nitro, halogen, cyano, carboxyl and glycosyl.

In another preferred embodiment, $R^1$ or $R^2$ is each preferably independently selected from one or more of the group consisting of hydroxyl, fluorine, chlorine, cyano, $C_{1-3}$ alkyl, substituted $C_{1-3}$ alkyl, $C_{1-2}$ alkoxy or substituted $C_{1-2}$ alkoxy, the substituent is selected from one or more of the group consisting of deuterium, hydroxyl, amino, nitro, fluorine, chlorine, cyano and carboxyl.

When m, n, p or q in the present invention is greater than 2, it means that there can be multiple defined corresponding groups (such as $R^1$ defined by m) and these multiple groups can be the same groups selected from a limited scope (such as scope defined by $R^1$), can also be different groups selected from the limited scope.

In a preferred embodiment, m or n is 0, 1, or 2.

In another preferred embodiment, m or n is 1 or 2.

$R^1$ or $R^2$ is each independently selected from hydroxyl, halogen, cyano, $C_{1-3}$ alkyl, $C_{1-3}$ alkoxy or substituted $C_{1-2}$ alkoxy and the substituent is selected from deuterium, hydroxyl, amino, fluorine or carboxyl; m or n is 0, 1, or 2.

In a preferred embodiment, $R^3$ or $R^4$ is each independently selected from the group consisting of hydrogen, deuterium, hydroxyl, amino, nitro, cyano, $C_{1-3}$ alkyl, substituted $C_{1-5}$ alkyl, $C_{1-3}$ alkoxy and substituted $C_{1-3}$ alkoxy, and the substituent is selected from one or more of the group consisting of deuterium, hydroxyl, amino, nitro, cyano, carboxyl and glycosyl.

In another preferred embodiment, $R^3$ or $R^4$ is each independently selected from the group consisting of hydrogen, deuterium, hydroxyl, amino, $C_{1-3}$ alkyl and $C_{1-3}$ alkoxy.

In another preferred embodiment, $R^3$ or $R^4$ is each independently selected from the group consisting of hydrogen, hydroxyl, amino, $C_{1-3}$ alkyl, substituted $C_{1-5}$ alkyl, $C_{1-3}$ alkoxy and substituted $C_{1-3}$ alkoxy, the substituent is selected from one or more of the group consisting of deuterium, hydroxyl, amino, fluorine and carboxyl.

In a preferred embodiment, $R^5$ is selected from one or more of the group consisting of hydrogen, deuterium, hydroxyl, halogen, cyano, $C_{1-3}$ alkyl, substituted $C_{1-3}$ alkyl, $C_{1-3}$ alkoxy and substituted $C_{1-3}$ alkoxy, and the substituent is selected from one or more of the group consisting of deuterium, hydroxyl, amino, nitro, halogen, cyano, carboxyl and glycosyl.

In another preferred embodiment, $R^5$ is selected from one or more of the group consisting of hydrogen, deuterium, hydroxyl, halogen, cyano and $C_{1-2}$ alkoxy.

In another preferred embodiment, $R^5$ is selected from the group consisting of hydrogen, hydroxyl, halogen, cyano, $C_{1-2}$ alkoxy and substituted $C_{1-3}$ alkoxy, and the substituent is selected from the group consisting of deuterium, hydroxyl, fluorine and carboxyl.

In a preferred embodiment, $R^6$ is selected from one or more of the group consisting of hydrogen, deuterium, hydroxyl, halogen, cyano, amino, $C_{1-5}$ alkyl, substituted $C_{1-5}$ alkyl, $C_{1-3}$ alkoxy and substituted $C_{1-3}$ alkoxy, and the substituent is selected from one or more of the group consisting of deuterium, hydroxyl, amino, nitro, halogen, cyano and carboxyl.

In another preferred embodiment, $R^6$ is selected from the group consisting of hydrogen, deuterium, hydroxyl, amino, $C_{1-3}$ alkyl, substituted $C_{1-5}$ alkyl, $C_{1-3}$ alkoxy and substituted $C_{1-3}$ alkoxy, and the substituent is selected from one or more of the group consisting of deuterium, hydroxyl, amino, fluorine, carboxyl and cyano.

In a preferred embodiment, p is 0, 1, 2, or 3.

In another preferred embodiment, p is 0 or 1.

In a preferred embodiment, q is 0, 1, or 2.

In another preferred embodiment, q is 0 or 1.

In another preferred embodiment, $R^6$ is selected from one or more of the group consisting of hydrogen, deuterium, hydroxyl, cyano, amino, $C_{1-3}$ alkyl, substituted $C_{1-3}$ alkyl, $C_{1-3}$ alkoxy and substituted $C_{1-3}$ alkoxy, and the substituent is selected from the group consisting of deuterium, hydroxyl, amino, fluorine and carboxyl.

In a preferred embodiment, Fe or $R^8$ is each independently selected from the group consisting of hydrogen, deuterium, hydroxyl, halogen, amino, cyano, $C_{1-3}$ alkyl, substituted $C_{1-3}$ alkyl, $C_{1-3}$ alkoxy and substituted $C_{1-3}$ alkoxy, and the substituent is selected from one or more of the group consisting of deuterium, hydroxyl, amino and halogen.

In another preferred embodiment, Fe or $R^8$ is each independently selected from the group consisting of hydrogen, deuterium, hydroxyl, $C_{1-3}$ alkoxy and substituted $C_{1-3}$ alkoxy, and the substituent is selected from one or more of the group consisting of deuterium, hydroxyl, amino and halogen.

In another preferred embodiment, Fe or $R^8$ is each independently selected from one or more of the group consisting of hydrogen, hydroxyl, cyano, $C_{1-3}$ alkyl, substituted $C_{1-3}$ alkyl, $C_{1-3}$ alkoxy and substituted $C_{1-3}$ alkoxy, and the substituent is selected from one or more of the group consisting of deuterium, hydroxyl, amino and fluorine.

In a preferred embodiment, A is selected from the group consisting of oxygen, sulfur and CHR', R' is selected from the group consisting of hydroxyl, amino, cyano, carboxyl and substituted $C_{1-3}$ alkyl, and the substituent is selected from one or more of the group consisting of hydroxyl, amino, cyano and carboxyl.

In another preferred embodiment, A is selected from the group consisting of oxygen, sulfur and CHR', and R' is selected from the group consisting of hydroxyl, amino, cyano, hydroxy-substituted $C_{1-3}$ alkyl and amino-substituted $C_{1-3}$ alkyl.

In a preferred embodiment, A is selected from oxygen or sulfur.

In another preferred embodiment, A is selected from oxygen.

In a preferred embodiment, A' or A" is each independently selected from oxygen, sulfur, CO or CHR.

In another preferred embodiment, A' or A" is each independently selected from oxygen, sulfur or CO.

In a preferred embodiment, R is selected from the group consisting of hydrogen, deuterium, hydroxyl, amino, nitro, cyano, $C_{1-3}$ alkyl and substituted $C_{1-3}$ alkyl, and the substituent is selected from one or more of the group consisting of hydroxyl, amino, carboxyl and cyano.

In another preferred embodiment, R is selected from the group consisting of hydroxyl, amino and substituted $C_{1-3}$ alkyl, and the substituent is selected from the group consisting of deuterium, hydroxyl and amino.

In the present invention, "E or G is each independently selected from C or CH" means that E or G is C respectively, or E or G is CH, respectively. When E or G is C, respectively, there is a carbon-carbon double bond between E and G, and when E or G is CH, respectively, there is a carbon-carbon single bond between E and G. In a preferred embodiment, E or G is each independently selected from CH, and there is a carbon-carbon single bond between E and G.

In a preferred embodiment, X or Y is each independently selected from CH or N.

In another preferred embodiment, X and Y are not simultaneously selected from N.

In a preferred embodiment, Z or Z' is selected from CH.

The substituent groups in the present invention, such as substituted alkyl, substituted alkoxy, substituted alkylthio, substituted amino, etc., when not specifically defined, the substituent groups are selected from one or more of the group consisting of deuterium, hydroxyl, amino, nitro, halogen, cyano, carboxyl, $C_{1-3}$ alkyl, $C_{1-3}$ alkoxy and glycosyl.

When there are multiple substituent groups in each group of the present invention (such as $R^1$, $R^2$, $R^3$, $R^4$, $R^5$, $R^6$, $R^7$, $R^8$, etc.), these substituent groups can be selected from the same substituent groups or different substituent groups.

In a preferred embodiment, the compounds of the present invention are selected from the following compounds,
2-{8-hydroxy-3-(4-hydroxy-3-methoxyphenyl)-2-hydroxymethyl-2,3-dihydrobenzo[b][1,4]dioxan-6-yl}chroman-3,4,5,7-tetraol (4);
(2R,3S)-2-{(2R,3R)-3-(4-hydroxy-3-methoxyphenyl)-2-hydroxymethyl-2,3-dihydrobenzo[b][1,4]dioxan-6-yl}chroman-3,4,5,7-tetraol (5);
(2R,3S)-2-{(2R,3R)-3-(4-hydroxy-3-methoxyphenyl)-2-hydroxymethyl-2,3-dihydrobenzo[b][1,4]dioxan-6-yl}chroman-3,5,7-triol (6);
2-{8-hydroxy-3-(4-hydroxy-3-methoxyphenyl)-2-hydroxymethyl-2,3-dihydrobenzo[b][1,4]dioxan-6-yl}chroman-3,5,7-triol (7);
2-{3-(6-methoxypyridin-3-yl)-2,3-dihydrobenzo[b][1,4]dioxan-6-yl}chroman-3,4,5,7-tetraol (22);
2-{3-(5-methoxypyridin-2-yl)-2-methyl-2,3-dihydrobenzo[b][1,4]dioxan-6-yl}chroman-3,4,5,7-tetraol (38);
2-{3-(5-hydroxypyridin-2-yl)-2-methyl-2,3-dihydrobenzo[b][1,4]dioxan-6-yl}chroman-3,4,5,7-tetraol (45);
(2R,3S)-4-amino-2-{(2R,3R)-3-(4-hydroxy-3-methoxyphenyl)-2-hydroxymethyl-2,3-dihydrobenzo[b][1,4]dioxan-6-yl}chroman-3,5,7-triol (47);
(2R,3S)-2-{(2R,3R)-2-hydroxymethyl-3-[3-methoxy-4-(trideuteromethoxy)phenyl]-2,3-dihydrobenzo[b][1,4]dioxan-6-yl}-5,7-bis(trideuteromethoxy)chroman-3-ol (55);
2-{8-hydroxy-3-(4-hydroxy-3-methoxyphenyl)-2-hydroxymethyl-2,3-dihydrobenzo[b][1,4]dioxan-6-yl}-7-methoxy-chroman-3,4,5-triol (66);
2-{8-hydroxy-3-(4-hydroxy-3-methoxyphenyl)-2-hydroxymethyl-2,3-dihydrobenzo[b][1,4]dioxan-6-yl}-7-methoxychroman-3,5-diol (67);
7-{(3-hydroxy-5,7-dimethoxychroman-2-yl)-2-(4-hydroxy-3-methoxyphenyl)-3-hydroxymethyl-2,3-dihydrobenzo[b][1,4]dioxane}-5-ol (78);
2-{8-hydroxy-3-(4-hydroxy-3-methoxyphenyl)-2-hydroxymethyl-2,3-dihydrobenzo[b][1,4]dioxan-6-yl}-5-methoxychroman-3,7-diol (85);
2-{8-hydroxy-3-(4-hydroxy-3-methoxyphenyl)-2-hydroxymethyl-2,3-dihydrobenzo[b][1,4]dioxan-6-yl}-5,7-dimethoxychroman-3,4-diol (92);
7-fluoro-2-{8-hydroxy-3-(4-hydroxy-3-methoxyphenyl)-2-hydroxymethyl-2,3-dihydrobenzo[b][1,4]dioxan-6-yl}chroman-3,4,5-triol (101);
7-ethoxy-2-{8-hydroxy-3-(4-hydroxy-3-methoxyphenyl)-2-hydroxymethyl-2,3-dihydrobenzo[b][1,4]dioxan-6-yl}chroman-3,5-diol (105);
5-ethoxy-2-{8-hydroxy-3-(4-hydroxy-3-methoxyphenyl)-2-hydroxymethyl-2,3-dihydrobenzo[b][1,4]dioxan-6-yl}chroman-3,7-diol (109);
2-{8-bromo-3-(4-hydroxy-3-methoxyphenyl)-2-hydroxymethyl-2,3-dihydrobenzo[b][1,4]dioxan-6-yl}chroman-3,4,5,7-tetraol (117);
2-{8-bromo-3-(4-hydroxy-3-methoxyphenyl)-2-hydroxymethyl-2,3-dihydrobenzo[b][1,4]dioxan-6-yl}chroman-3,5,7-triol (118);
2-(4-hydroxy-3-methoxyphenyl)-3-hydroxymethyl-7-(3,5,7-trihydroxychroman-2-yl)-2,3-dihydrobenzo[b][1,4]dioxan-5-carbonitrile (119);
(2R,3S)-2-{2-aminomethyl-(2R,3R)-3-(4-hydroxy-3-methoxyphenyl)-2,3-dihydrobenzo[b][1,4]dioxan-6-yl}chroman-3,5,7-triol (126);
2-{8-hydroxy-3-(4-hydroxy-3-methoxyphenyl)-2-hydroxymethyl-2,3-dihydrobenzo[b][1,4]dioxan-6-yl}chroman-3,4,6,7-tetraol (136);
2-{8-hydroxy-3-(4-hydroxy-3-methoxyphenyl)-2-hydroxymethyl-2,3-dihydrobenzo[b][1,4]dioxan-6-yl}chroman-3,6,7-triol (137);
2-{3-(4-hydroxy-3-methoxyphenyl)-2-hydroxymethyl-2,3-dihydrobenzo[b][1,4]dioxan-6-yl}chroman-3,6,7-triol (140).

The present invention also provides a pharmaceutical composition, which uses the compounds, optical isomers or pharmaceutically acceptable salts of the present invention as active ingredients or main active ingredients, supplemented by pharmaceutically acceptable excipients. That is, in the pharmaceutical composition of the present application, in addition to the compounds of the present invention, optical isomers or pharmaceutically acceptable salts thereof as active ingredients, other types of active ingredients can be further added to achieve multiple purposes of enhancing efficacy and reducing side effects through combination medication.

The compounds, optical isomers, or pharmaceutically acceptable salts thereof involved in the present invention can be used in the preparation of drugs for the treatment or prevention of liver diseases, especially in the preparation of drugs for the treatment or prevention of fatty liver, liver fibrosis and liver cirrhosis. On the other hand, the compounds of the present invention, optical isomers or pharmaceutically acceptable salts thereof can be used in the treatment or prevention of liver diseases, especially in the treatment or prevention of fatty liver, liver fibrosis and liver cirrhosis.

Unless otherwise stated, the following terms used in the claims and specification have the following meanings:

"Hydrogen" refers to protium (1H), which is the main stable isotope of hydrogen.

"Deuterium" refers to a stable isotope of hydrogen, also known as heavy hydrogen, and its element symbol is D.

"Halogen" means fluorine atom, chlorine atom, bromine atom or iodine atom.

"Hydroxy" refers to the —OH group.

"Amino" refers to the —NH$_2$ group.

"Cyano" refers to the —CN group.

"Nitro" refers to the —NO$_2$ group.

"Carboxyl" refers to the —COOH group.

"Alkyl" means a saturated aliphatic hydrocarbon group of 1-10 carbon atoms, including straight-chain and branched-chain groups (the numerical range mentioned in this application, such as "1-10", refers to the group, in this case, an alkyl group, can contain 1 carbon atom, 2 carbon atoms, 3 carbon atoms, etc., up to 10 carbon atoms). An alkyl group containing 1-4 carbon atoms is called a lower alkyl group. When a lower alkyl group has no substituents, it is called an unsubstituted lower alkyl group. The alkyl group can be $C_{1-6}$ alkyl, $C_{1-5}$ alkyl, $C_{1-4}$ alkyl, $C_{1-3}$ alkyl, $C_{1-2}$ alkyl, $C_{2-3}$ alkyl, $C_{2-4}$ alkyl, etc. Specific alkyl groups include, but are not limited to, methyl, ethyl, propyl, 2-propyl, n-butyl, isobutyl, or tert-butyl. Alkyl groups can be substituted or unsubstituted.

"Alkoxy" means —O-(unsubstituted alkyl) and —O-(unsubstituted cycloalkyl) group, which further means —O-(unsubstituted alkyl). Representative examples include, but are not limited to, methoxy, ethoxy, propoxy, cyclopropoxy, etc.

"Alkylthio" means —S-(unsubstituted alkyl) and —S-(unsubstituted cycloalkyl) group, which further means —S-(unsubstituted alkyl). Representative examples include, but are not limited to, methylthio, ethylthio, propylthio, cyclopropylthio, etc.

"CO" means —C(=O)— group.

"E or G is each independently selected from C or CH" means that when there is a carbon-carbon single bond between E and G, E or G is each independently selected from CH, and when there is a carbon-carbon double bond between E and G, E Or G is each independently selected from C.

"Glycosyl" means a monosaccharide residue or a polysaccharide residue. The monosaccharides used herein are 3-C monosaccharides to 8-C monosaccharides, preferably 6-carbon monosaccharides having the chemical formula $C_6H_{12}O_6$ (ie, hexose). The hexose can be D configuration, L configuration or a combination thereof. Hexoses are generally classified according to functional groups. For example, aldhexose has an aldehyde group in position 1, for example, allose, altrose, glucose, mannose, gulose, idose, galactose and talose; while kethexose has a keto group in position 2, for example, allulose, fructose, sorbose and tagatose. Hexose also contains 6 hydroxyl groups. The aldehyde or ketone functional groups in the hexose can react with adjacent hydroxyl functional groups to form intramolecular hemiacetals or hemiketals, respectively. If the resulting cyclose has a 5-membered ring, it is furanose. If the resulting cyclose is a 6-membered ring, it is a pyranose. The ring opens and closes spontaneously, allowing the bond between the carbonyl group and the adjacent carbon atom to rotate, resulting in two different configurations ($\alpha$ and $\beta$). The hexose can be in the form of S configuration or the R configuration.

"Pharmaceutically acceptable salts" are salts comprising a compound of general formula (I) or (II) and an organic acid or inorganic acid, and represents those salts that retain the biological effectiveness and properties of the parent compound. Such salts include:

(1) acid addition salts, obtained by reacting a free base of the parent compound with an inorganic acid or organic acid, the inorganic acid include, such as (but not limited to) hydrochloric acid, hydrobromic acid, nitric acid, phosphoric acid, metaphosphoric acid, sulfuric acid, sulfurous acid and perchloric acid, the organic acid include, such as (but not limited to) acetic acid, propionic acid, acrylic acid, oxalic acid, (D) or (L) malic acid, fumaric acid, maleic acid, hydroxybenzoic acid, γ-hydroxybutyric acid, methoxybenzoic acid, phthalic acid, methanesulfonic acid, ethanesulfonic acid, naphthalene-1-sulfonic acid, naphthalene-2-sulfonic acid, p-toluenesulfonic acid, salicylic acid, tartaric acid, citric acid, lactic acid, mandelic acid, succinic acid or malonic acid, etc.

(2) salts formed by replacing acidic protons in the parent compound with metal ions or the coordinating acidic protons in the parent compound with organic bases, the metal ions include, such as alkali metal ions, alkaline earth metal ions or aluminum ions, the organic bases include, such as ethanolamine, diethanolamine, triethanolamine, tromethamine, N-methylglucamine, etc.

"Pharmaceutical composition" refers to a mixture of one or more compounds described herein or their pharmaceutically acceptable salts and prodrugs and other chemical ingredients, such as pharmaceutically acceptable carriers and excipients. The purpose of the pharmaceutical composition is to facilitate the administration of the compounds to the organism.

"Prodrug" refer to a compound that has pharmacological effects after being transformed in vivo. The prodrug itself has no biological activity or very low activity, and becomes an active substance after being metabolized in vivo. The purpose of this process is to increase the bioavailability of the drug, strengthen the targeting ability, and reduce the toxicity and side effects of the drug.

The present invention further claims a pharmaceutical composition comprising any one of the above-mentioned compounds, its pharmaceutically acceptable salt or easily hydrolyzable prodrug amide and other pharmaceutically active ingredients.

The present invention also includes any one of the above-mentioned compounds, its pharmaceutically acceptable salt, easily hydrolyzable prodrug amide or isomer, which can be formulated into any clinically or pharmaceutically acceptable dosage form in a manner known in the art. When used for oral administration, it can be formulated into conventional solid formulations, such as tablet, capsule, pill, granule, etc.; it can also be formulated into oral liquid formulations, such as oral solution, oral suspension, and syrup, etc.

In the case of formulation, it is prepared using diluents or excipients such as fillers, extenders, binders, wetting agents, disintegrants, and surfactants that are commonly used. The solid formulation for oral administration can be prepared by mixing the compound with more than one excipient, such as starch, calcium carbonate, sucrose, lactose, or gelatin. In addition to simple excipients, lubricants such as magnesium stearate and talc are also used. Liquid formlations for oral administration may include various excipients other than a simple diluent such as water and liquid paraffin, such as wetting agents, sweeteners, fragrances, preservatives, etc. In formulations for non-oral administration, as non-aqueous solvents, suspensions, such as propylene glycol, polyethylene glycol, vegetable oils such as olive oil, and injectable esters such as ethyl oleate can be used. The substrates as adjuvants, such as witepsol, polyethylene glycol, Tween 61, cocoa butter, glyceryl laurate, glycerinated gelatin, etc. can be used.

The application amount of the compound as the active ingredient of the pharmaceutical composition of the present invention can be determined according to the age, gender, weight, and disease, and the specific dosage can be determined according to the route of administration, the degree of the disease, gender, weight, and age, etc. Therefore, the administration dosage does not limit the scope of the present invention in any form. The pharmaceutical composition can be administered to mammals such as rats, mice, livestock, humans and the like in various ways. All modes of administration are expected, for example, oral, rectal or intravenous, intramuscular, subcutaneous, inhalation intrabronchial, intrauterine, dural or intracerebrovascular administration.

Compared with the existing drugs (especially silymarin), the solubility of the compounds of the present invention in different solutions has been greatly improved, which can more effectively increase the absorption efficiency of the drug by the human body, and greatly improve the related therapeutic effects. The compounds represented by formula (I) or (II), optical isomers or pharmaceutically acceptable salts thereof provided by the present invention have good therapeutic effects and low toxicity on liver diseases, especially fatty liver. Experiments show that the some of the compounds involved in the invention have a significant therapeutic effect on zebrafish non-alcoholic fatty liver, and can also significantly improve and treat non-alcoholic fatty liver in mice. Therefore, they are used in the drugs for treatment or prevention of liver diseases, especially fatty liver, liver fibrosis and liver cirrhosis and have a good application prospect.

Figure 1:
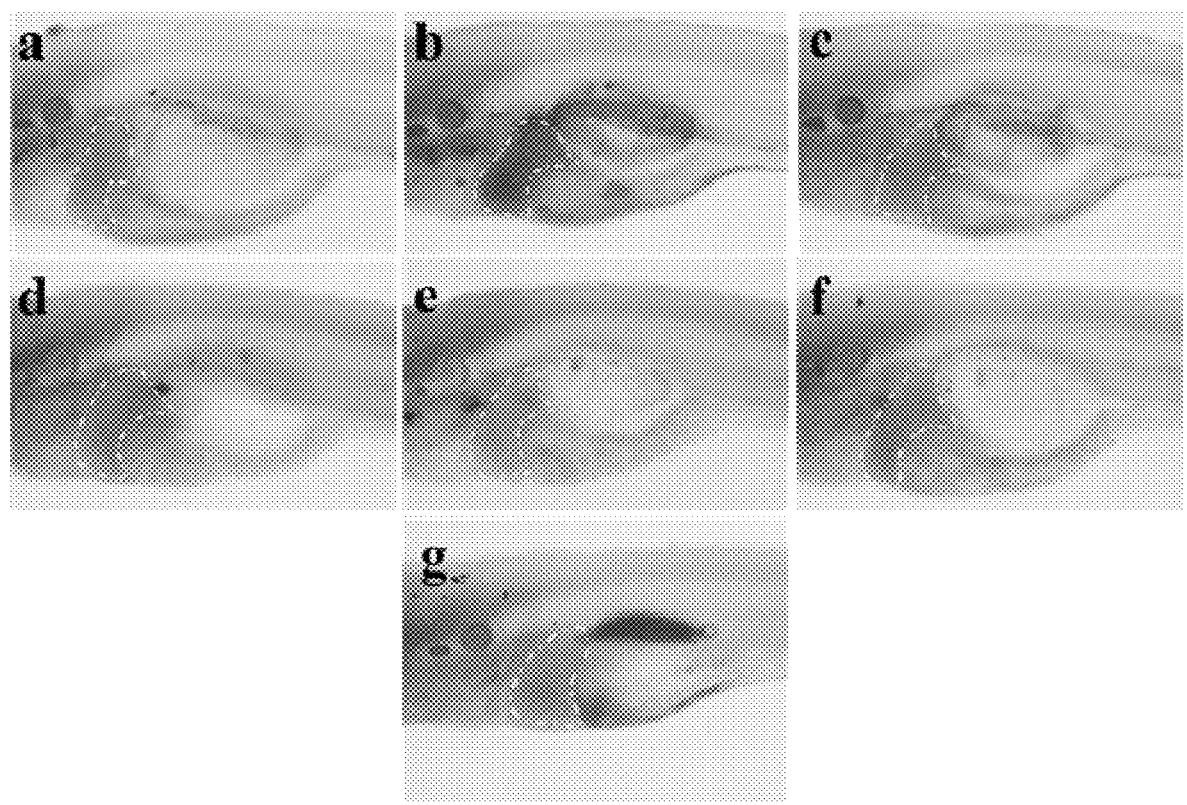
FIG. 1 is a microscopic examination photo of zebrafish with oil red 0 staining after administration of each test compound.
Figure 2:
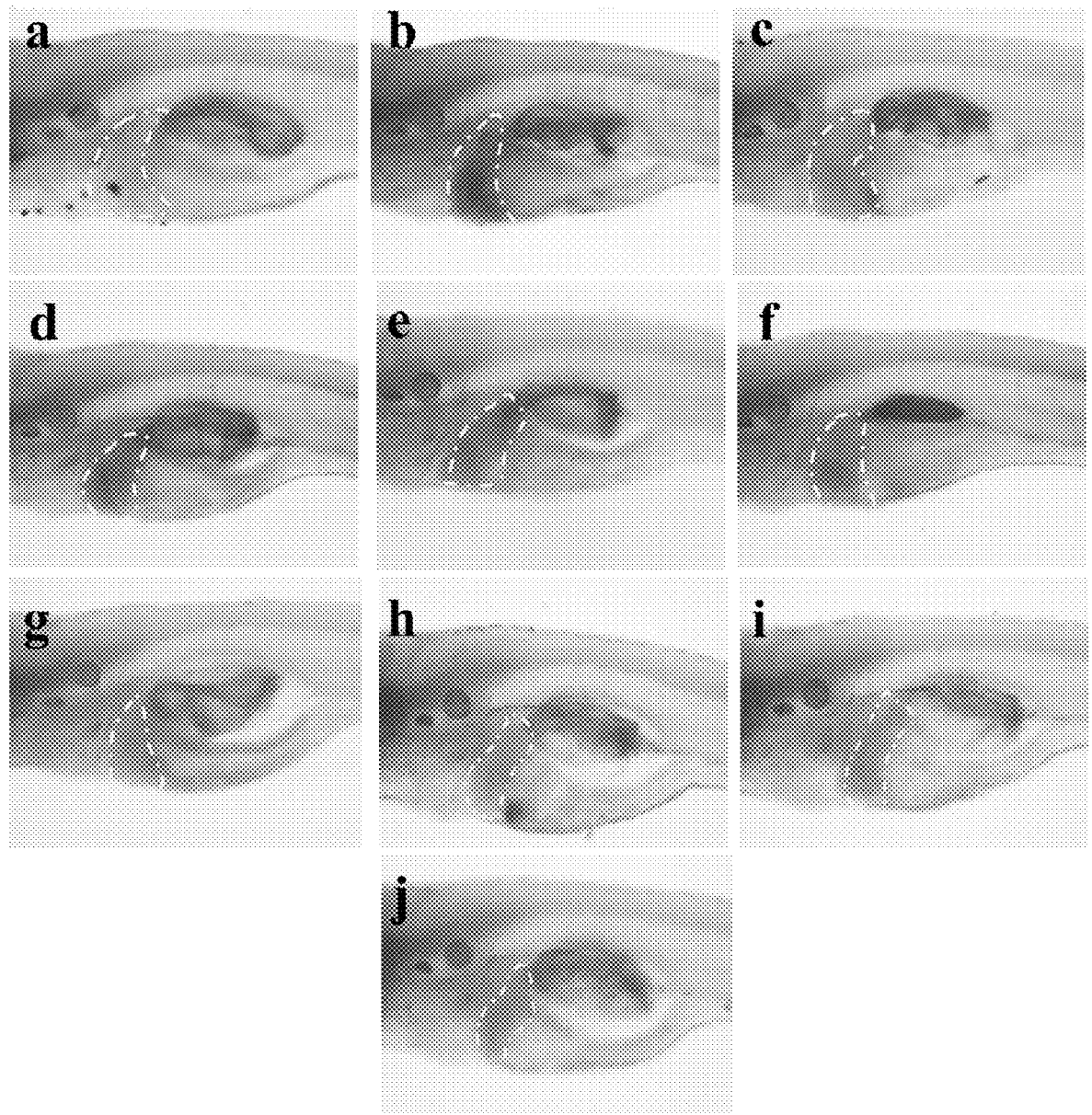
Figure 3:
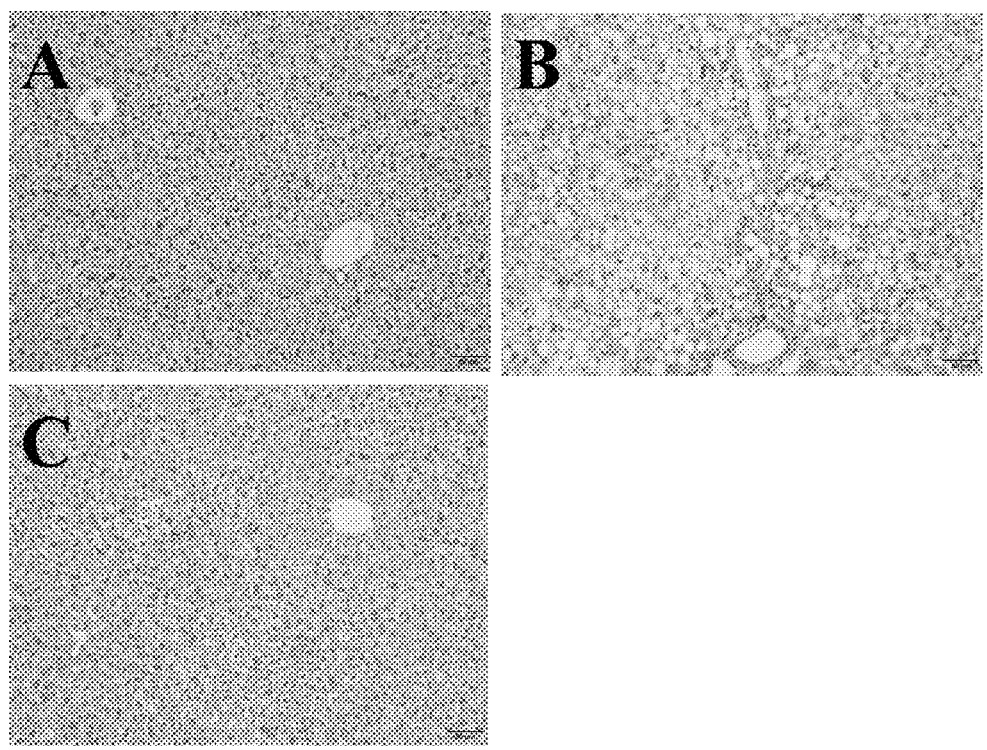

wherein, the dotted area shows the liver, a is the normal control group, b is the model control group, c is the positive control group of S-adenosylmethionine (50 μM), and d is the positive control group of silymarin (200 μM), e is compound 4 group (200 μM), f is compound 6 group (200 μM), g is compound 7 group (200 μM);

FIG. 2 is a microscopic examination photo of zebrafish with oil red 0 staining after administration of each test compound;

wherein, the dotted area shows the liver, a is the normal control group, b is the model control group, c is the positive control group of S-adenosylmethionine (50 μM), and d is the positive control group of silymarin (100 μM), e is compound 4 group (100 μM), f is compound 6 group (100 μM), g is compound 7 group (100 μM), h is compound 67 group (100 μM), i is compound 85 group (100 μM), j is compound 92 group (100 μM);

FIG. 3 is a photo of histopathological staining (HE staining, 400×);

wherein, A is the normal control group; B is the model control group; C is the compound 7 low-dose group (35 mg/kg).

SPECIFIC MODE FOR CARRYING OUT EMBODIMENTS

The present invention will be further described with reference to the following examples, but the protection scope of the present invention is not limited to the following examples.

Example 1: Synthesis of 2-{8-hydroxy-3-(4-hydroxy-3-methoxyphenyl)-2-hydroxymethyl-2,3-dihydrobenzo[b][1,4]dioxan-6-yl}chroman-3,4,5,7-tetraol (4)

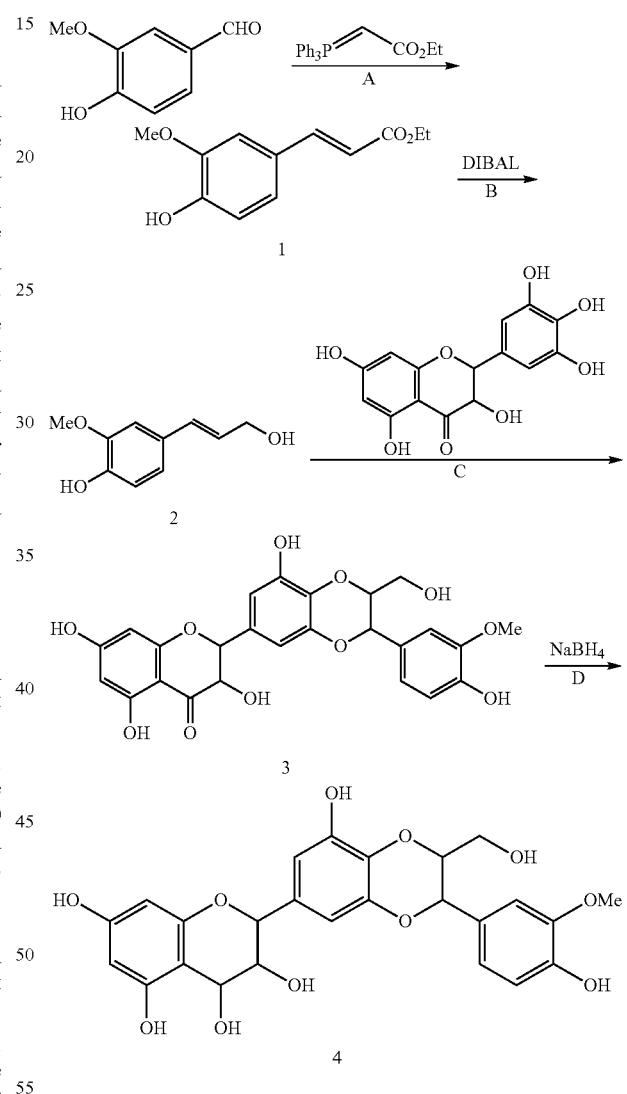

Step A: A mixture of 4-hydroxy-3-methoxybenzaldehyde (2.0 g, 13.1 mmol), ethoxyformylmethylene triphenylphosphine (5.04 g, 14.5 mmol) and dichloromethane (40 mL) was stirred overnight at room temperature. The solvent was evaporated under reduced pressure, and the product was purified by column chromatography (200-300 mesh silica gel, ethyl acetate:petroleum ether=1:20-1:10 elution) to give ethyl 3-(4-hydroxy-3-methoxyphenyl)acrylate (1) (2.5 g). The yield was 85.9%.

Step B: At −50° C., to a solution of compound 1 (2.48 g, 11.2 mmol) in THF (25 mL) was added dropwise a solution of 1.5 M diisobutylaluminum hydride in THF (25 mL). After the addition, the temperature was raised to room temperature and stirring was continued for 0.5 hour. The reaction solution was poured slowly into ice water (40 mL), and the pH was adjusted to 5-6 with 2 M citric acid solution. Ethyl acetate (50 mL×3) was used for extraction, and the combined organic phase was washed with saturated brine (30 mL), and dried over anhydrous sodium sulfate. The solvent was evaporated under reduced pressure, and the product was purified by column chromatography (200-300 mesh silica gel, ethyl acetate:petroleum ether=5:1-2:1 elution) to give 4-(3-hydroxyprop-1-ene-1-yl) methoxyphenol (2) (1.62 g). The yield was 80.3%. $^1$H NMR (DMSO-d$_6$, 400 MHz) δ 8.99 (s, 1H), 6.99 (d, J=2.0 Hz, 1H), 6.81-6.78 (m, 1H), 6.72-6.70 (m, 1H), 6.44-6.40 (m, 1H), 6.21-6.14 (m, 1H), 4.77-4.74 (m, 1H), 4.09-4.06 (m, 2H), 3.81 (s, 3H).

Step C: A mixture of 3,5,7-trihydroxy-2-(3,4,5-trihydroxyphenyl)chroman-4-one (622 mg, 1.94 mmol), compound 2 (350 mg, 1.94 mmol)), acetone (10 mL) and benzene (20 mL) was stirred at 50° C. for 10 minutes, and then silver carbonate (536 mg, 1.94 mmol) was added. After the addition, the resulting mixture was stirred at this temperature overnight. After cooling to room temperature, THF (15 mL) was added, filtration was performed to remove insolubles. The solvent was evaporated under reduced pressure, and the product was purified by column chromatography (200-300 mesh silica gel, methanol:dichloromethane=1:100-1:60 elution) to give 3,5,7-trihydroxy-2-{8-hydroxy-3-(4-hydroxy-3-methoxyphenyl)-2-hydroxymethyl-2,3-dihydrobenzo[b][1,4]dioxan-6-yl}chroman-4-one (3) (200 mg). The yield was 20.7%. $^1$H NMR (DMSO-d$_6$, 400 MHz) δ 11.88 (s, 1H), 10.84 (s, 1H), 9.21 (s, 1H), 9.15 (s, 1H), 7.00 (d, J=1.6 Hz, 1H), 6.86-6.77 (m, 2H), 6.58-6.53 (m, 2H), 5.91-5.79 (m, 3H), 4.99-4.96 (m, 1H), 4.87-4.83 (m, 2H), 4.53-4.48 (m, 1H), 4.11 (s, 1H), 3.78 (s, 3H), 3.51-3.48 (m, 2H). MS (EI, m/z): 497.4 [M−H]$^-$.

Step D: A mixture containing compound 3 (170 mg, 0.341 mmol), methanol (6 mL) and sodium borohydride (32 mg, 0.846 mmol) was stirred at room temperature for 2 hours, and then sodium borohydride (32 mg, 0.846 mmol) was added, and the resulting mixture was stirred overnight at room temperature. After adding water (15 mL), the pH was adjusted to 5-6 with 2 M citric acid solution. Ethyl acetate/THF (3V/1V, 15 mL×3) was used for extraction, and the combined organic phase was washed with saturated brine (10 mL), and dried over anhydrous sodium sulfate. The solvent was evaporated under reduced pressure, and the product was purified by column chromatography (200-300 mesh silica gel, dichloromethane:ethyl acetate:THF=5:1:1-2:1:1 elution) to give 2-{8-hydroxy-3-(4-hydroxy-3-methoxyphenyl)-2-hydroxymethyl-2,3-dihydrobenzo[b][1,4]dioxan-6-yl}chroman-3,4,5,7-tetraol (4). $^1$H NMR (DMSO-d$_6$, 400 MHz) δ 9.20 (bs, 4H), 6.98 (d, J=2.0 Hz, 1H), 6.86-6.79 (m, 2H), 6.48 (s, 1H), 6.39 (d, J=1.6 Hz, 1H), 5.85 (d, J=2.4 Hz, 1H), 5.68-5.67 (m, 1H), 5.18-5.16 (m, 1H), 4.85-4.83 (m, 2H), 4.69-4.68 (m, 1H), 4.51-4.48 (m, 1H), 4.08 (bs, 1H), 3.78 (s, 3H), 3.67-3.60 (m, 2H), 3.50-3.40 (m, 2H). MS (EI, m/z): 499.2 [M−H]$^-$.

Example 2: Synthesis of (2R,3S)-2-{(2R,3R)-3-(4-hydroxy-3-methoxyphenyl)-2-hydroxymethyl-2,3-dihydrobenzo[b][1,4]dioxan-6-yl}chroman-3,4,5,7-tetraol (5)

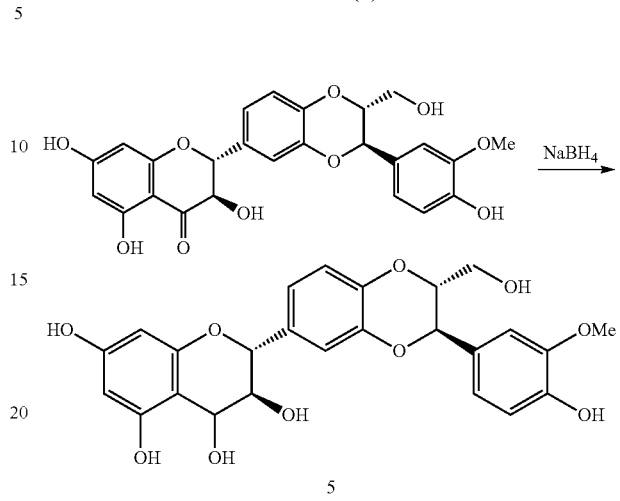

(2R,3R)-3,5,7-trihydroxy-2-((2R,3R)-3-(4-hydroxy-3-methoxyphenyl)-2-hydroxymethyl-2,3-dihydrobenzo[b][1,4]dioxan-6-yl}chroman-4-one (purchased from Shanghai Dibo Biotechnology Co., Ltd., production batch number EE09) was used as a raw material to synthesize compound 5, the experimental operation was performed in accordance with the preparation method of step D in Example 1. $^1$H NMR (DMSO-de, 400 MHz) δ 9.28-9.14 (s, 3H), 7.02-6.79 (m, 6H), 5.88-5.87 (m, 1H), 5.70-5.69 (m, 1H), 5.58 (s, 1H), 5.20 (s, 1H), 4.95-4.88 (m, 2H), 4.72 (s, 1H), 4.64-4.60 (m, 1H), 4.14 (s, 1H), 3.80-3.75 (m, 4H), 3.54 (s, 1H), 3.36-3.28 (m, 1H). MS (EI, m/z): 483.2 [M−H]$^-$.

Example 3: Synthesis of (2R,3S)-2-{(2R,3R)-3-(4-hydroxy-3-methoxyphenyl)-2-hydroxymethyl-2,3-dihydrobenzo[b][1,4]dioxan-6-yl}chroman-3,5,7-triol (6)

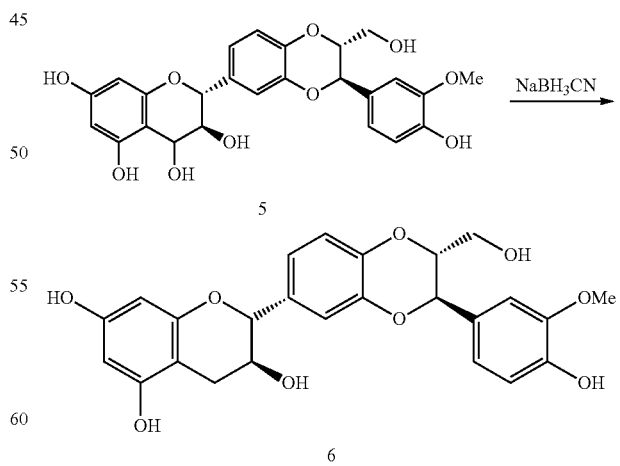

To a solution of compound 5 (103 mg, 0.213 mmol) in acetic acid (3 mL) was added sodium cyanoborohydride (50 mg, 0.796 mmol) in portions. After the addition, the resulting mixture was stirred at room temperature for 0.5 hour.

After adding water (10 mL), ethyl acetate (15 mL×3) was used for extraction, the combined organic phase was washed with saturated sodium bicarbonate solution (10 mL), and dried over anhydrous sodium sulfate. The solvent was evaporated under reduced pressure, and the product was purified by column chromatography (200-300 mesh silica gel, ethyl acetate:petroleum ether=5:1 elution) to give (2R, 3S)-2-{(2R,3R)-3-(4-hydroxy-3-methoxyphenyl)-2-hydroxymethyl-2,3-dihydrobenzo[b][1,4]dioxan-6-yl}chroman-3,5,7-triol (6). $^1$H NMR (DMSO-$d_6$, 400 MHz) δ 9.20 (s, 1H), 9.14 (s, 1H), 8.95 (s, 1H), 6.99-6.78 (m, 6H), 5.89 (d, J=2.0 Hz, 1H), 5.70 (s, 1H), 4.96-4.86 (m, 3H), 4.59-4.56 (m, 1H), 4.13 (s, 1H), 3.89-3.87 (m, 1H), 3.77 (s, 3H), 3.54-3.51 (m, 1H), 3.35-3.27 (m, 1H), 2.68-2.65 (m, 1H), 2.40-2.34 (m, 1H). MS (EI, m/z): 467.2 [M−H]$^-$.

Example 4: synthesis of 2-{8-hydroxy-3-(4-hydroxy-3-methoxyphenyl)-2-hydroxymethyl-2,3-dihydrobenzo[b][1,4]dioxan-6-yl}chroman-3,5,7-triol (7)

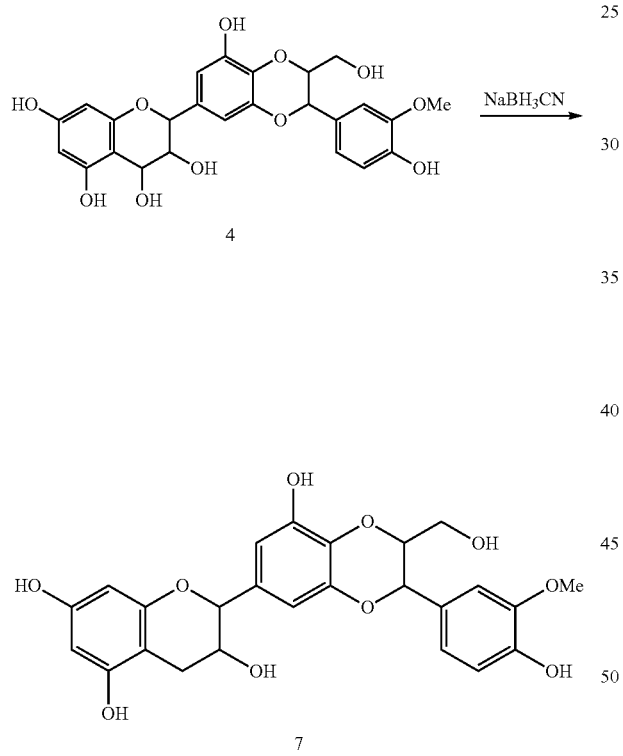

With compound 4 as a raw material, the experimental operation of synthesizing compound 7 was performed in accordance with the preparation method of Example 3. $^1$H NMR (DMSO-$d_6$, 400 MHz) δ 9.17 (s, 1H), 9.12 (s, 1H), 9.07 (s, 1H), 8.93 (s, 1H), 6.98-6.97 (m, 1H), 6.85-6.76 (m, 2H), 6.42 (d, J=2.0 Hz, 1H), 6.34 (d, J=2.0 Hz, 1H), 5.88 (d, J=2.0 Hz, 1H), 5.69 (d, J=2.0 Hz, 1H), 4.92-4.90 (m, 1H), 4.84-4.79 (m, 2H), 4.51-4.49 (m, 1H), 4.09-4.05 (m, 1H), 3.85-3.80 (m, 1H), 3.77 (s, 3H), 3.49-3.45 (m, 1H), 3.40-3.38 (m, 1H), 2.64-2.60 (m, 1H), 2.38-2.32 (m, 1H). MS (EI, m/z): 483.2 [M−H]$^-$.

Example 5: Synthesis of 3,5,7-trihydroxy-2-{3-(6-methoxypyridin-3-yl)-2,3-dihydrobenzo[b][1,4]dioxan-6-yl}chroman-4-one (21) and 2-{3-(6-methoxypyridin-3-yl)-2,3-dihydrobenzo[b][1,4]dioxan-6-yl}chroman-3,4,5,7-tetraol (22)

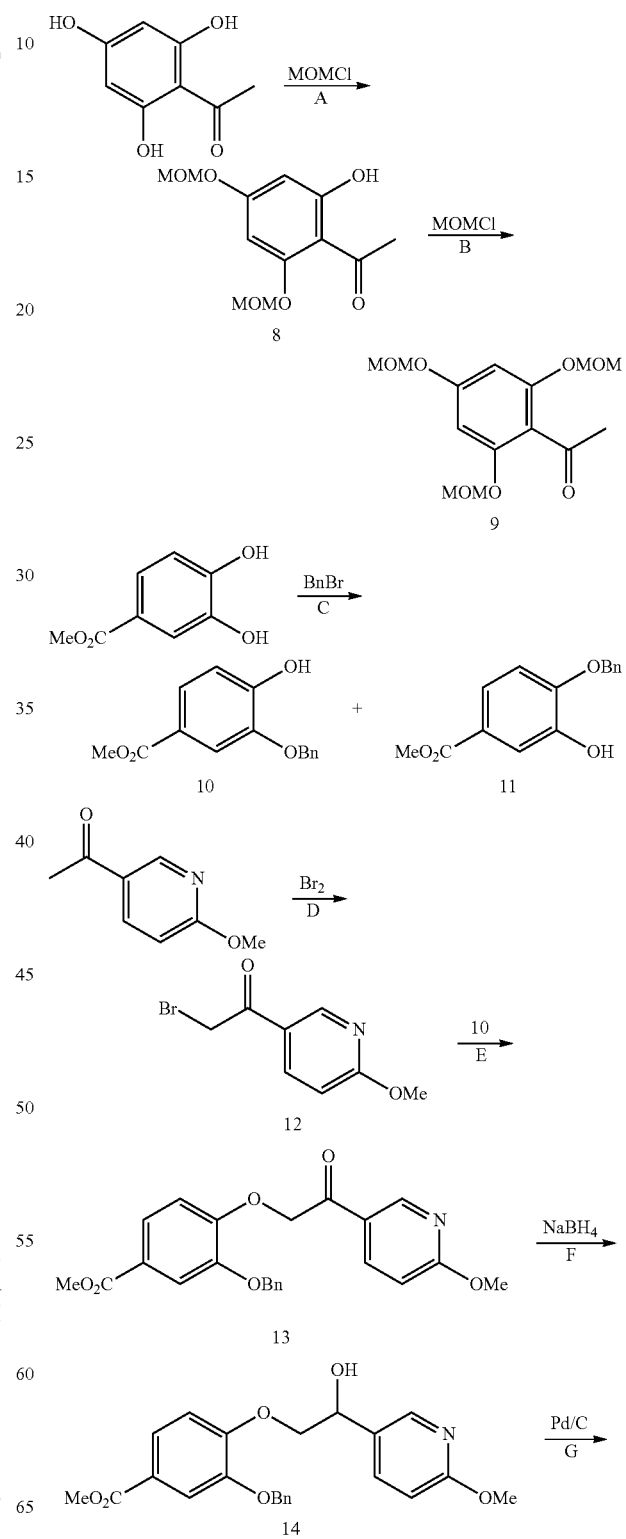

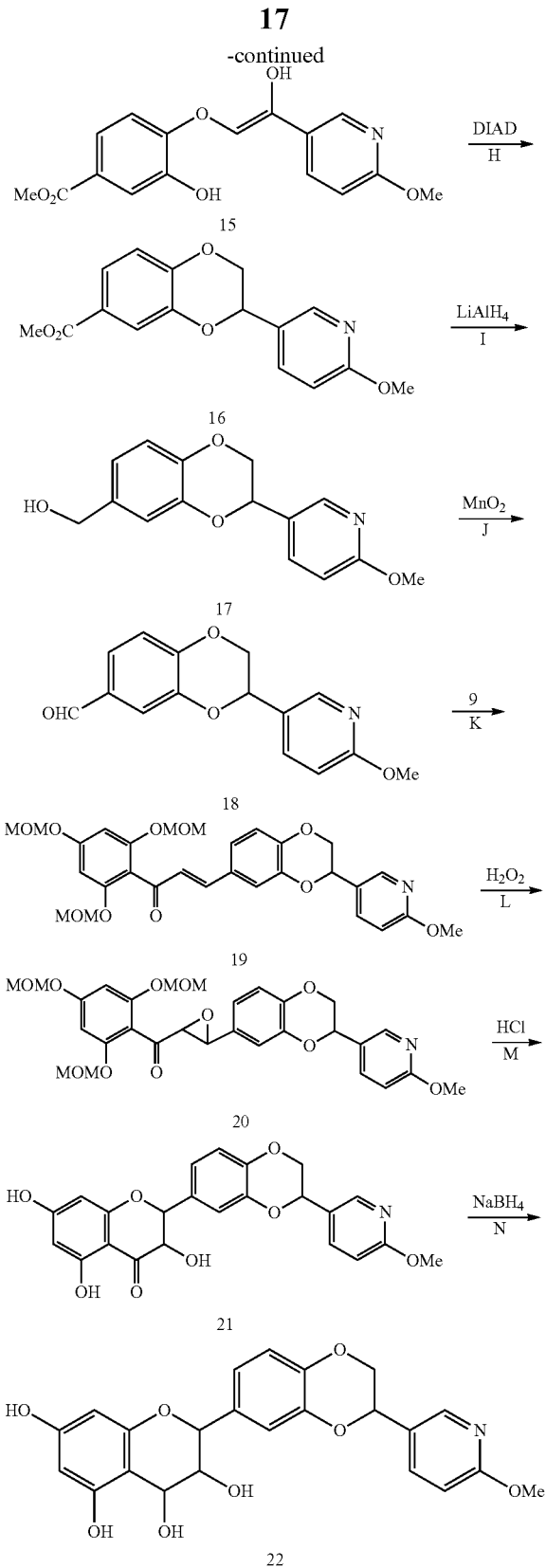

Step A: A mixture of 2,4,6-trihydroxyacetophenone (5.0 g, 29.7 mmol), chloromethyl methyl ether (9.7 g, 120.5 mmol), potassium carbonate (37.1 g, 269 mmol) and acetone (100 mL) was stirred under reflux for 2 hours. The solvent was evaporated under reduced pressure. Water (50 mL) was added, and the mixture was extracted with ethyl acetate (40 mL×3). The combined organic phase was washed with saturated brine (30 mL) and dried over anhydrous sodium sulfate. The solvent was evaporated under reduced pressure, and the product was purified by column chromatography (200-300 mesh silica gel, methyl tert-butyl ether:petroleum ether=1:15-1:8 elution) to give 1-[2-hydroxy-4, 6-bis(methoxymethoxy)]acetophenone (8) (5.1 g). The yield was 67.0%. $^1$H NMR (DMSO-$d_6$, 400 MHz) δ 13.34 (s, 1H), 6.23 (d, J=2.4 Hz, 1H), 6.19 (d, J=2.4 Hz, 1H), 5.30 (s, 2H), 5.23 (s, 2H), 3.44 (s, 3H), 3.38 (s, 3H), 2.60 (s, 3H).

Step B: Under an ice water bath, chloromethyl methyl ether (2.52 g, 31.3 mmol) was added dropwise to a mixture containing compound 8 (4.0 g, 15.6 mmol), sodium hydroxide (1.84 g, 46 mmol), water (4 mL), tetrabutylammonium bromide (252 mg, 0.782 mmol) and dichloromethane (60 mL). After the addition, the resulting mixture was stirred at room temperature for 1 hour. Afer adding water (40 mL), extraction was performed with dichloromethane (60 mL×2), the combined organic phase was washed with saturated brine (30 mL), and dried over anhydrous sodium sulfate. The solvent was evaporated under reduced pressure to give 2,4,6-tris(methoxymethoxy)acetophenone (9) (4.6 g). The yield was 98.2%.

Step C: To a mixture containing methyl 3,4-dihydroxybenzoate (25.0 g, 149 mmol), potassium carbonate (20.5 g, 149 mmol) and acetonitrile (500 mL) was added dropwise benzyl bromide (25.4 g, 149 mmol). After the addition, the resulting mixture was stirred overnight under reflux. Most of the solvent was evaporated under reduced pressure, water (400 mL) was added, extraction was performed with ethyl acetate (200 mL×3), and the combined organic phase was washed with saturated brine (100 mL) and dried over anhydrous sodium sulfate. The solvent was evaporated under reduced pressure, and the product was purified by column chromatography (200-300 mesh silica gel, ethyl acetate:petroleum ether:dichloromethane=1:50:1-1:50:2 elution) to give methyl 3-benzyloxy-4-hydroxybenzoate (10) (4.7 g) and methyl 4-benzyloxy-3-hydroxybenzoate (11) (11.3 g). The yields were 12.2% and 29.4% respectively.

Step D: 5-acetyl-2-methoxypyridine (2.54 g, 16.8 mmol) was dissolved in acetic acid (40 mL), 47% aqueous hydrobromic acid (5.79 g, 33.6 mmol) was added, and then bromine (2.95 g, 18.5 mmol) in acetic acid (5 mL) was added. After the addition, the temperature was raised to 40° C., and after stirring for about 3 hours, bromine (600 mg, 3.75 mmol) was added, and then stirring was continued for 5 hours. After adding water (150 mL), extraction was performed with methyl tert-butyl ether (60 mL×4), and the combined organic phase was washed with saturated brine (40 mL) and dried over anhydrous sodium sulfate. The solvent was evaporated under reduced pressure, and the product was purified by column chromatography (200-300 mesh silica gel, ethyl acetate:petroleum ether=1:100-1:10 elution) to give 2-bromo-1-(6-methoxy pyridin-3-yl)ethanone (12) (1.91 g). The yield was 49.4%.

Step E: A mixture containing compound 10 (1.84 g, 7.12 mmol), compound 12 (1.64 g, 7.13 mmol), cesium carbonate (2.90 g, 8.90 mmol) and acetonitrile (25 mL) was stirred at 30° C. for 2 hours. After adding water (120 mL), extraction was performed with ethyl acetate (60 mL×3), the combined organic phase was washed with water (40 mL) and saturated brine (40 mL) successively, and dried over anhydrous sodium sulfate. The solvent was evaporated under reduced pressure to give methyl 3-benzyloxy-4-[2-(6-methoxypyridin-3-yl)-2-oxoethoxy]benzoate (13) (2.83 g). The yield was 97.4%. $^1$H NMR (DMSO-$d_6$, 400 MHz) δ 8.90 (d, J=2.4 Hz, 1H), 8.23 (dd, J=2.4, 8.8 Hz, 1H), 7.62-7.48 (m, 4H), 7.42-7.29 (m, 3H), 7.06 (d, J=8.8 Hz, 1H), 6.97 (d, J=8.8 Hz, 1H), 5.68 (s, 2H), 5.20 (s, 2H), 3.97 (s, 3H), 3.81 (s, 3H).

Step F: To a solution of compound 13 (2.83 g, 6.95 mmol) in methanol (40 mL) was added sodium borohydride (526 mg, 13.9 mmol) in batches. After the addition, the resulting mixture was stirred at room temperature for 4 hours. After adding water (120 mL), extraction was performed with ethyl acetate (60 mL×3), and the combined organic phase was washed with water (40 mL) and saturated brine (40 mL) successively, and dried over anhydrous sodium sulfate. The solvent was evaporated under reduced pressure to give methyl 3-benzyloxy-4-[2-hydroxy-2-(6-methoxypyridin-3-yl)ethoxy]benzoate (14) (2.61 g). The yield was 91.7%.

Step G: To a solution of compound 14 (2.6 g, 6.35 mmol) in THF (40 mL) was added 5% palladium on carbon (260 mg) and the resulting mixture was stirred under hydrogen at 30° C. for 3 hours under normal pressure. After filtering through celite and the solvent was evaporated under reduced pressure to give 3-hydroxy-2-(3-hydroxy-4-methoxyphenyl)-5,7-bis(methoxymethoxy)chroman-4-one (15) (1.96 g). The yield was 96.7%.

Step H: To a solution of compound 15 (1.94 g, 6.08 mmol) and triphenylphosphine (2.15 g, 8.20 mmol) in THF (35 mL) was added diisopropyl azodiacetate (1.66 g, 8.21 mmol), after the addition, the resulting mixture was stirred under reflux for 3.5 hours under nitrogen. The solvent was evaporated under reduced pressure and the product was purified by column chromatography (200-300 mesh silica gel, ethyl acetate:dichloromethane=1:1-10:1 elution) to give methyl 3-(6-methoxypyridine-3-yl)-2,3-dihydrobenzo[b][1,4]dioxan-6-carboxylate (16) (1.75 g). The yield was 95.5%. $^1$H NMR (DMSO-$d_6$, 400 MHz) δ 8.30 (d, J=2.4 Hz, 1H), 7.82 (dd, J=2.4, 8.8 Hz, 1H), 7.53-7.49 (m, 2H), 7.06 (d, J=8.8 Hz, 1H), 6.99 (d, J=8.8 Hz, 1H), 5.33-5.30 (m, 1H), 4.53-4.50 (m, 1H), 4.32-4.27 (m, 1H), 3.87 (s, 3H), 3.81 (s, 3H). MS (EI, m/z): 302.1 [M+H]$^+$.

Step I: Under an ice-water bath, a solution of compound 16 (1.75 g, 5.81 mmol) in THF (7 mL) was added dropwise to a mixture containing lithium aluminum hydride (441 mg, 11.6 mmol) and THF (15 mL). After the addition, the stirring was continued for 5 minutes, then the temperature was raised to room temperature and the stirring was continued for 30 minutes. After the reaction was over, the temperature was reduced to 0~5° C., and water (0.5 mL), 10% sodium hydroxide solution (1.0 mL) and water (1.5 mL) in sequence were slowly added to the reaction mixture. After the addition was complete, the temperature was raised to room temperature and the stirring was continued for 5 minutes. After filtration through celite to remove insolubles, ethyl acetate was added (60 mL) to the filtrate, which was washed with saturated brine (15 mL×2) and dried over anhydrous sodium sulfate, and the solvent was evaporated under reduced pressure to give 3-(6-methoxypyridin-3-yl)-2,3-dihydrobenzo[b][1,4]dioxan-6-methanol (17) (1.52 g). The yield was 95.7%.

Step J: A mixture containing compound 17 (1.50 g, 5.49 mmol), manganese dioxide (2.39 g, 27.5 mmol) and chloroform (15 mL) was stirred at 43° C. overnight. After filtration through celite to remove insolubles, the solvent was evaporated under reduced pressure and the product was purified by column chromatography (200-300 mesh silica gel, ethyl acetate:petroleum ether=1:25~1:12 elution) to give 3-(6-methoxypyridin-3-yl)-2,3-dihydrobenzo[b][1,4]dioxan-6-carbaldehyde (18) (1.26 g). The yield was 84.6%.

Step K: At room temperature, compound 18 (300 mg, 1.11 mmol) and compound 9 (332 mg, 1.11 mmol) were added to potassium hydroxide (186 mg, 3.32 mol) in ethanol (10 mL). After that, the resulting mixture was stirred at 30° C. overnight. Most of the solvent was evaporated under reduced pressure, water (70 mL) was added, extraction was performed with ethyl acetate (70 mL×3), and the combined organic phase was washed with saturated brine (40 mL), and dried over anhydrous sodium sulfate. The solvent was evaporated under reduced pressure, and the product was purified by column chromatography (200-300 mesh silica gel, ethyl acetate:petroleum ether=1:20-1:2 elution) to give 3-{3-(6-methoxypyridin-3-yl)-2,3-dihydrobenzo[b][1,4]dioxan-6-yl}-1-[2,4,6-tris(methoxymethoxy)phenyl]prop-2-en-1-one (19) (510 mg). The yield was 83.0%.

Step L: Sodium hydroxide (360 mg, 9.0 mmol) was dissolved in water (1.5 mL) and methanol (15 mL), then compound 19 (500 mg, 0.903 mmol) and 30% hydrogen peroxide (1.03 g, 9.09 mmol) in sequence were added, the resulting mixture was stirred at 25° C. overnight. Saturated brine (40 mL) was added, extraction was performed with ethyl acetate (40 mL×3), and the combined organic phase was washed with saturated brine (20 mL), and dried over anhydrous sodium sulfate. The solvent was evaporated under reduced pressure to give {3-{3-(6-methoxypyridin-3-yl)-2,3-dihydrobenzo[b][1,4]dioxan-6-yl}ethylene oxide-2-yl}[2,4,6-tris(methoxymethoxy)phenyl]methanone (20) (500 mg). The yield was 97.2%.

Step M: To a solution of compound 20 (490 mg, 0.860 mmol) in methanol (9 mL) and THF (3 mL) was added dropwise concentrated hydrochloric acid (1.2 mL). After the addition, the resulting mixture was stirred at 65° C. for 2 hours. Most of the solvent was evaporated under reduced pressure. Water (20 mL) was added, extraction was performed with ethyl acetate (25 mL×3). The combined organic phase was washed with saturated brine (15 mL) and dried over anhydrous sodium sulfate. The solvent was evaporated under reduced pressure and the product was purified by column chromatography (200-300 mesh silica gel, ethyl acetate:petroleum ether:dichloromethane=1:15:1-1:4:1 elution) to give 3,5,7-trihydroxy-2-{3-(6-methoxypyridin-3-yl)-2,3-dihydrobenzo[b][1,4]dioxan-6-yl}chroman-4-one (21). $^1$H NMR (DMSO-de, 400 MHz) δ 11.89 (s, 1H), 10.85 (s, 1H), 8.31 (d, J=2.0 Hz, 1H), 7.85-7.82 (m, 1H), 7.14-7.13 (m, 1H), 7.05-7.02 (m, 1H), 6.98-6.96 (m, 1H), 6.90 (d, J=8.8 Hz, 1H), 5.92-5.91 (m, 1H), 5.88-5.87 (m, 1H), 5.83-5.82 (m, 1H), 5.29-5.27 (m, 1H), 5.11-5.08 (m, 1H), 4.64-4.59 (m, 1H), 4.46-4.43 (m, 1H), 4.24-4.17 (m, 1H), 3.87 (s, 3H). MS (EI, m/z): 436.1 [M–H]$^-$.

Step N: Compound 21 was reduced with sodium borohydride to give 2-{3-(6-methoxypyridin-3-yl)-2,3-dihydrobenzo[1,4]dioxan-6-yl}chroman-3,4,5,7-tetraol (22), the specific experimental operations were in accordance with the preparation method of step D in Example 1. MS (EI, m/z): 438.1 [M–H]$^-$.

Example 6: Synthesis of 3,5,7-trihydroxy-2-{3-(6-methoxypyridin-3-yl)-2-methyl-2,3-dihydrobenzo[b][1, 4]dioxan-6-yl}chroman-4-one (37) and 2-{3-(5-methoxypyridin-2-yl)-2-methyl-2,3-dihydrobenzo[b][1,4]dioxan-6-yl}chroman-3,4,5,7-tetraol (38)

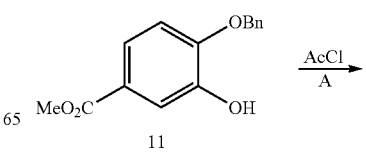

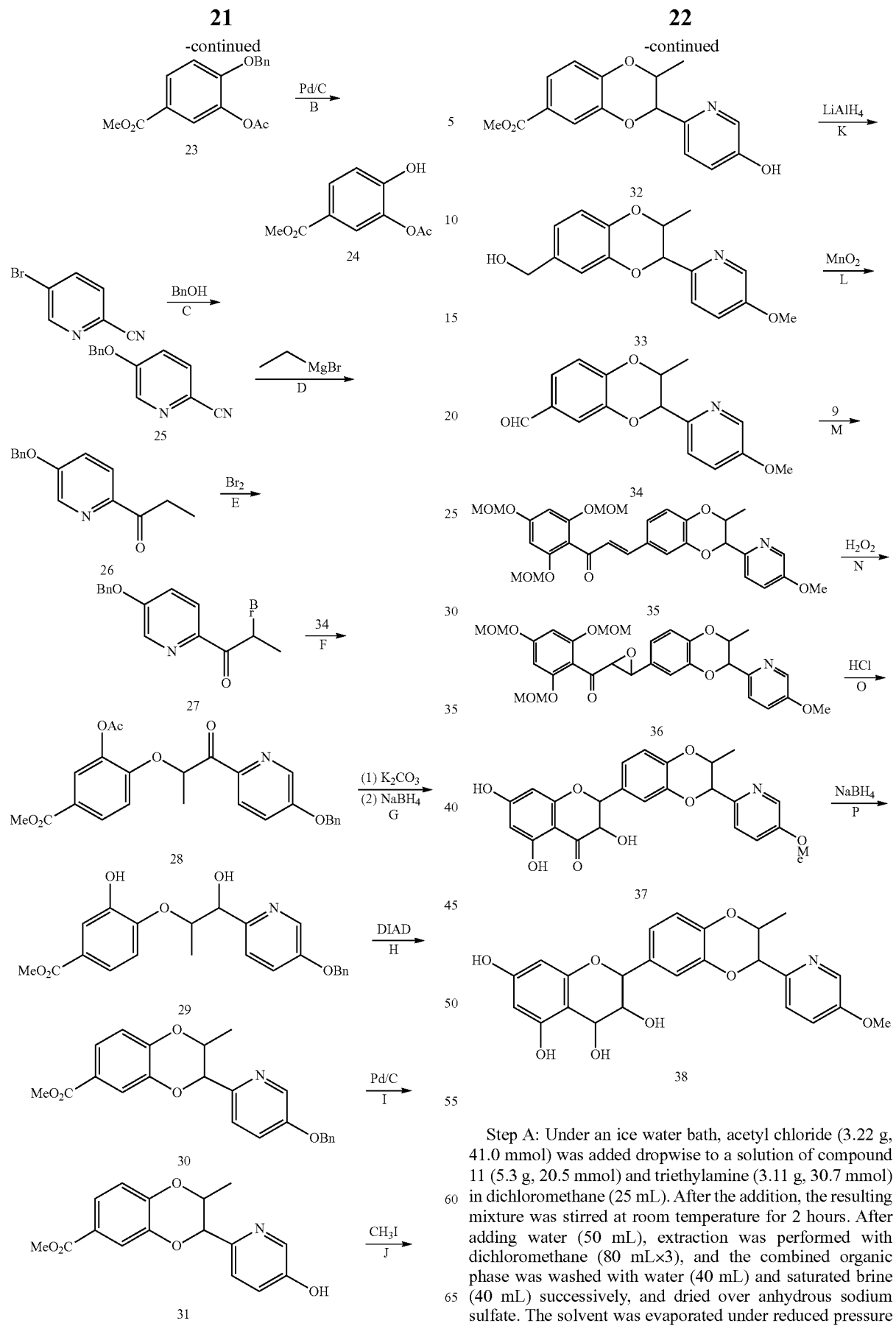

Step A: Under an ice water bath, acetyl chloride (3.22 g, 41.0 mmol) was added dropwise to a solution of compound 11 (5.3 g, 20.5 mmol) and triethylamine (3.11 g, 30.7 mmol) in dichloromethane (25 mL). After the addition, the resulting mixture was stirred at room temperature for 2 hours. After adding water (50 mL), extraction was performed with dichloromethane (80 mL×3), and the combined organic phase was washed with water (40 mL) and saturated brine (40 mL) successively, and dried over anhydrous sodium sulfate. The solvent was evaporated under reduced pressure and the product was recrystallized from dichloromethane/ petroleum ether to give methyl 3-acetoxy-4-benzyloxybenzoate (23) (5.5 g). The yield was 89.3%.

Step B: To a solution of compound 23 (8.6 g, 28.6 mmol) in THF (120 mL) was added 5% palladium on carbon (800 mg), and the resulting mixture was stirred under hydrogen at 25° C. and normal pressure overnight. After filtering through celite, the solvent was evaporated under reduced pressure, and the product was recrystallized from petroleum ether to give methyl 3-acetoxy-4-hydroxybenzoate (24) (5.7 g). The yield was 94.8%.

Step C: Benzyl alcohol (7.68 g, 71.0 mmol) was dropwise added to a suspension of 60% sodium hydride (2.84 g, 71.0 mmol) in DMF (60 mL) at 0-5° C. After the addition, the stirring was continued for 10 minutes and then 5-bromo-2-cyanopyridine (10.0 g, 54.6 mmol) was added in portions. The resulting mixture was continuously stirred at this temperature for 15 minutes. After adding water (180 mL) and then filtering, the filter cake was washed with water (100 mL) and then recrystallized with ethyl acetate/petroleum ether to give 5-benzyloxy-2-cyanopyridine (25) (9.2 g). The yield was 80.2%.

Step D: At −5-0° C., 2 M ethylmagnesium bromide in THF solution (26.5 mL, 53 mmol) was dropwise added to a solution of compound 25 (8.6 g, 40.9 mmol) in THF (30 mL). After the addition, the resulting mixture was stirred at this temperature for 1 hour. Water (90 mL) was slowly added, the pH was adjusted to 3-4 with 2 M hydrochloric acid and extraction was performed with ethyl acetate (100 mL×3). The combined organic phase was washed with water (50 mL) and saturated brine (50 mL) in sequence and dried over anhydrous sodium sulfate. The solvent was evaporated under reduced pressure to give 1-(5-benzyloxypyridin-2-yl)propan-1-one (26) (9.74 g). The yield was 98.7%.

The experimental operations of steps E and F were performed according to the preparation methods of steps D and E in Example 5 to give methyl 3-acetoxy-4-{[1-(5-benzyloxypyridin-2-yl)-1-oxypropan-2-yl]oxy}benzoate (28). $^1$H NMR (DMSO-d$_6$, 400 MHz) δ 8.54 (d, J=2.8 Hz, 1H), 8.03 (d, J=8.8 Hz, 1H), 7.75-7.67 (m, 3H), 7.52-7.50 (m, 2H), 7.45-7.36 (m, 3H), 6.91 (d, J=8.4 Hz, 1H), 6.28 (q, J=6.8 Hz, 1H), 5.34 (s, 2H), 3.81 (s, 3H), 2.30 (s, 3H), 1.57 (d, J=6.8 Hz, 3H).

Step G: A mixture containing compound 28 (5.0 g, 11.1 mmol), potassium carbonate (3.08 g, 22.3 mmol) and methanol (120 mL) was stirred at 5-10° C. for 15 minutes, then sodium borohydride (1.26 g, 33.3 mmol) was added and the resulting mixture was stirred at room temperature for 0.5 hour. Saturated brine (360 mL) was added and the pH was adjusted to 7-8 with 2 M citric acid solution. After extraction with ethyl acetate (100 mL×3), the combined organic phase was washed with saturated brine (50 mL×2), dried over anhydrous sodium sulfate and then filtered through a short silica gel pad. The solvent was evaporated under reduced pressure to give methyl 4-{[1-(5-benzyloxypyridin-2-yl)-1-hydroxyprop-2-yl]oxy}-3-hydroxybenzoate (29) (4.49 g). The yield was 98.8%. $^1$H NMR (CDCl$_3$, 400 MHz) δ 8.32 (s, 1H), 7.60 (d, J=2.0 Hz, 1H), 7.52-7.50 (m, 1H), 7.42-7.34 (m, 7H), 6.96 (d, J=8.4 Hz, 1H), 5.12 (s, 2H), 4.85-4.84 (m, 1H), 4.58-4.56 (m, 1H), 3.87 (s, 3H), 1.32 (d, J=6.4 Hz, 3H).

Step H: To a solution of compound 29 (4.49 g, 11.0 mmol) and triphenylphosphine (3.88 g, 14.8 mmol) in THF (20 mL) was added diisopropyl azodiacetate (2.99 g, 14.8 mmol). After the addition was complete, the resulting mixture was stirred under reflux for 2.5 hours under nitrogen. After cooling to room temperature, the solvent was evaporated under reduced pressure. The product was purified by column chromatography (200-300 mesh silica gel, ethyl acetate: petroleum ether=1:30-1:10 elution) to give methyl 3-(5-benzyloxy) Pyridin-2-yl)-2-methyl-2,3-dihydrobenzo[b][1,4]dioxan-6-carboxylate (30) (3.87 g). The yield was 89.9%.

Step I: To a solution of compound 30 (2.78 g, 7.10 mmol) in DMF (30 mL) was added 5% palladium on carbon (280 mg) and the resulting mixture was stirred under hydrogen at 40° C. for 4 hours under normal pressure. After filtration through celite, water (120 mL) was added, extraction was performed with ethyl acetate (60 mL×3), and the combined organic phase was washed with water (30 mL×2) and saturated brine (30 mL) in sequence, and dried over anhydrous sodium sulfate. The solvent was evaporated under reduced pressure to give methyl 3-(5-hydroxypyridin-2-yl)-2-methyl-2,3-dihydrobenzo[b][1,4]dioxan-6-carboxylate (31) (1.80 g). The yield was 84.1%.

Step J: The mixture containing compound 31 (575 mg, 1.91 mmol), potassium carbonate (343 mg, 2.49 mmol), methyl iodide (406 mg, 2.86 mmol) and DMF (10 mL) was stirred at 30° C. overnight. After adding water (40 mL), extraction was performed with ethyl acetate (20 mL×3), and the combined organic phase was washed with water (15 mL×2) and saturated brine (15 mL) in sequence, and dried over anhydrous sodium sulfate. The solvent was evaporated under reduced pressure to give methyl 3-(5-methoxypyridin-2-yl)-2-methyl-2,3-dihydrobenzo[b][1,4]dioxan-6-carboxylate (32) (617 mg). The yield was 100%.

The experimental operations of steps K and L were performed according to the preparation methods of steps G and H in Example 6, to give 3-(5-methoxymethoxypyridin-2-yl)-2-methyl-2,3-dihydrobenzo[b][1,4]dioxan-6-carbaldehyde (34). $^1$H NMR (DMSO-d$_6$, 400 MHz) δ 9.83 (s, 1H), 8.34 (d, J=2.4 Hz, 1H), 7.53-7.46 (m, 4H), 7.13 (d, J=8.4 Hz, 1H), 4.96 (d, J=7.2 Hz, 1H), 4.62-4.58 (m, 1H), 3.86 (s, 3H), 1.17 (d, J=7.2 Hz, 3H).

The experimental operations of steps M, N and O were carried out in accordance with the preparation methods of steps I, J and K in Example 6, to give 3,5,7-trihydroxy-2-{3-(5-methoxypyridin-2-yl)-2-Methyl-2,3-dihydrobenzo[b][1,4]dioxan-6-yl}chroman-4-one (37). $^1$H NMR (DMSO-d$_6$, 400 MHz) δ 11.90 (s, 1H), 10.87 (s, 1H), 8.34 (s, 1H), 7.50 (s, 2H), 7.11-6.96 (m, 3H), 5.92-5.84 (m, 3H), 5.10-5.08 (m, 1H), 4.88-4.86 (m, 1H), 4.61 (s, 1H), 4.45 (s, 1H), 3.87 (s, 3H), 1.15 (s, 3H). MS (EI, m/z): 450.1 [M−H]$^-$.

Step P: Compound 37 was reduced with sodium borohydride to give 2-{3-(5-methoxypyridin-2-yl)-2-methyl-2,3-dihydrobenzo[b][1,4]dioxan-6-yl}chroman-3,4,5,7-tetraol (38), the specific experimental operation was performed in accordance with the preparation method of step D in Example 1. MS (EI, m/z): 452.1 [M−H]$^-$.

Example 7: Synthesis of 3,5,7-trihydroxy-2-{3-(6-hydroxypyridin-3-yl)-2-methyl-2,3-dihydrobenzo[b][1,4]dioxan-6-yl}chroman-4-one (44) and 2-{3-(5-hydroxypyridin-2-yl)-2-methyl-2,3-dihydrobenzo[b][1,4]dioxan-6-yl}chroman-3,4,5,7-tetraol (45)

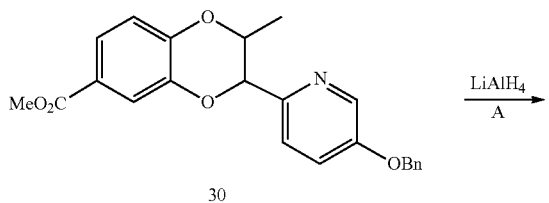

30

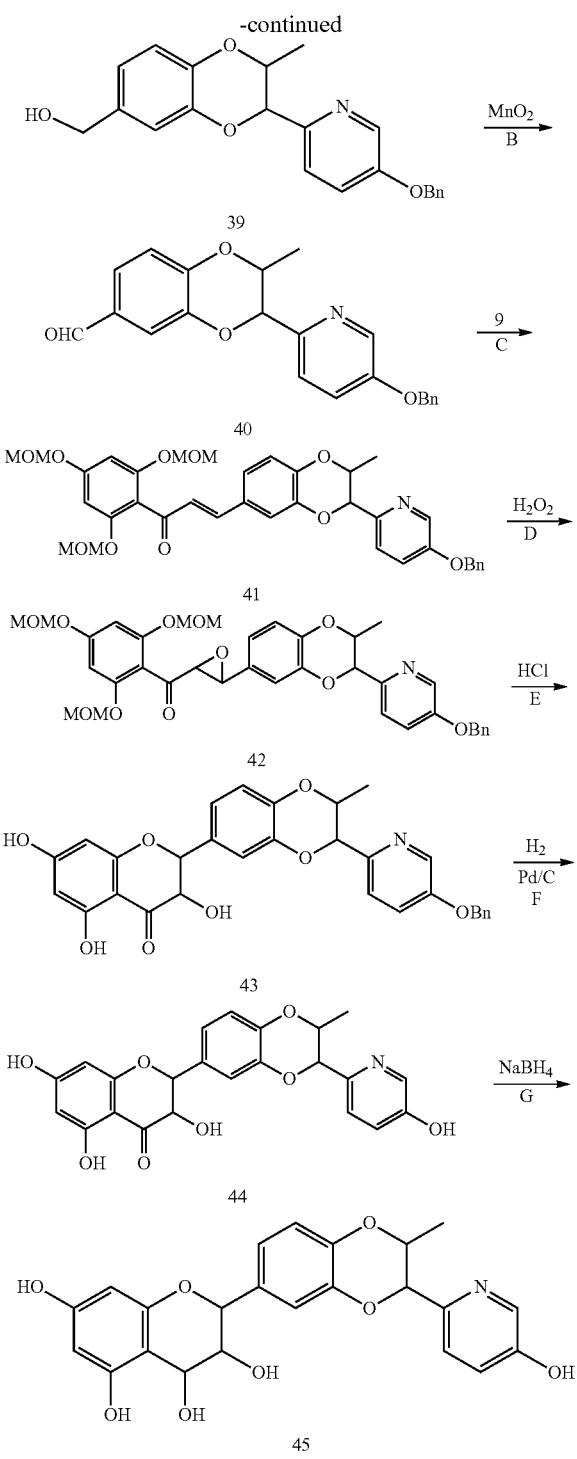

Step F: To a solution of compound 43 (780 mg, 1.57 mmol) in DMF (10 mL) was added 5% palladium on carbon (80 mg), and the resulting mixture was stirred under hydrogen at 40° C. and normal pressure overnight. After filtering through celite, water (40 mL) was added. After filtering, the filter cake was dissolved with ethyl acetate (20 mL×3), followed by washing with saturated brine (20 mL) and drying with anhydrous sodium sulfate. The solvent was evaporated under reduced pressure and the resulting product was recrystallized with ethyl acetate/petroleum ether to give 3,5,7-trihydroxy-2-{3-(5-hydroxypyridin-2-yl)-2-methyl-2,3-dihydrobenzo[b][1,4]dioxan-6-yl}chroman-4-one (44). $^1$H NMR (DMSO-d$_6$, 400 MHz) δ 11.90 (s, 1H), 10.87 (s, 1H), 10.16 (s, 1H), 8.17 (d, J=2.8 Hz, 1H), 7.39-7.37 (m, 1H), 7.26-7.23 (m, 1H), 7.10 (s, 1H), 7.03-7.01 (m, 1H), 6.96-6.94 (m, 1H), 5.92-5.82 (m, 3H), 5.10-5.07 (m, 1H), 4.80-4.78 (m, 1H), 4.63-4.59 (m, 1H), 4.43-4.39 (m, 1H), 1.15 (d, J=6.4 Hz, 3H). MS (EI, m/z): 436.1 [M−H]$^−$.

Step G: Compound 44 was reduced with sodium borohydride to give 2-{3-(5-hydroxypyridin-2-yl)-2-methyl-2,3-dihydrobenzo[b][1,4]dioxan-6-yl}chroman-3,4,5,7-tetraol (45), the specific experimental operations were performed in accordance with the preparation method of step D in Example 1. MS (EI, m/z): 438.1 [M−H]$^−$.

Example 8: Synthesis of (2R,3S)-3,5,7-trihydroxy-2-{(2R,3R)-3-(4-hydroxy-3-methoxyphenyl)-2-hydroxymethyl-2,3-dihydrobenzo[b][1,4]dioxan-6-yl}chroman-4-one oxime (46) and (2R,3S)-4-amino-2-{(2R,3R)-3-(4-hydroxy-3-methoxyphenyl)-2-hydroxymethyl-2,3-dihydrobenzo[b][1,4]dioxan-6-yl}chroman-3,5,7-triol (47)

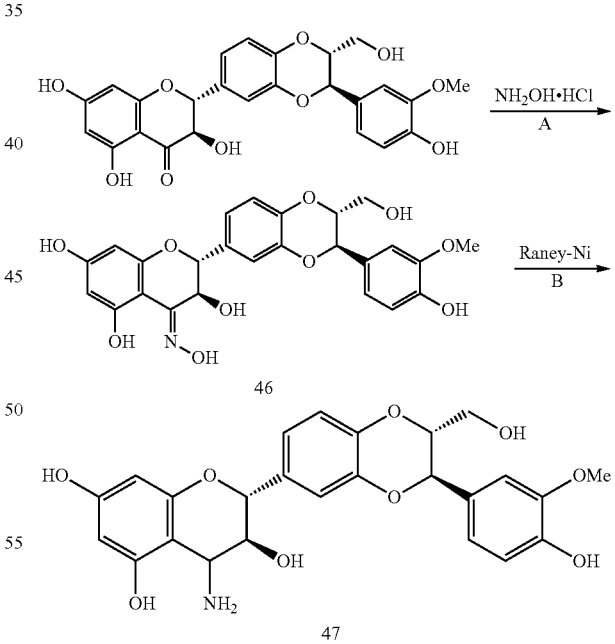

Using compound 30 as a raw material, the experimental operations of steps A, B, C, D and E were performed in accordance with the preparation methods of steps I, J, K, L and M in Example 5 to give 2-{3-(5-benzyloxypyridin-2-yl)-2-methyl-2,3-dihydrobenzo[b][1,4]dioxan-6-yl}-3,5,7-trihydroxychroman-4-one (43). $^1$H NMR (DMSO-d$_6$, 400 MHz) δ 11.90 (s, 1H), 10.86 (s, 1H), 8.40 (d, J=2.8 Hz, 1H), 7.56-7.36 (m, 7H), 7.11-6.94 (m, 3H), 5.92-5.82 (m, 3H), 5.22 (s, 2H), 5.10-5.07 (m, 1H), 4.87-4.86 (m, 1H), 4.63-4.58 (m, 1H), 4.47-4.42 (m, 1H), 1.14 (d, J=6.0 Hz, 3H).

Step A: A mixture of (2R,3R)-3,5,7-trihydroxy-2-{(2R,3R)-3-(4-hydroxy-3-methoxyphenyl)-2-hydroxymethyl-2,3-dihydrobenzo[b][1,4]dioxan-6-yl}chroman-4-one (500 mg, 1.04 mmol), hydroxylamine hydrochloride (94 mg, 1.35 mmol) and pyridine (5 mL) of the mixture was stirred at 70° C. overnight. After the reaction, the product was purified by column chromatography (200~300 mesh silica gel, dichloromethane:methanol=1:100~1:40 elution) to give (2R,3S)-3,5,7-trihydroxy-2-{(2R,3R)-3-(4-hydroxy-3-methoxyphenyl)-2-hydroxymethyl-2,3-dihydrobenzo[b][1,4]dioxane-6-yl}chroman-4-one oxime (46) (481 mg). The yield was 93.0%. $^1$H NMR (DMSO-$d_6$, 400 MHz) δ 11.34-11.32 (m, 1H), 11.09-10.80 (m, 1H), 9.85 (s, 1H), 9.15-9.14 (m, 1H), 7.08-6.72 (m, 5H), 6.56-6.46 (m, 1H), 5.93-5.85 (m, 2H), 5.36-5.32 (m, 1H), 4.96-4.90 (m, 3H), 4.17-4.14 (m, 1H), 3.79-3.75 (m, 3H), 3.62-3.60 (m, 3H). MS (EI, m/z): 496.1 [M–H]$^-$.

Step B: A mixture containing compound 46 (100 mg, 0.207 mmol), Raney nickel (10 mg) and methanol (15 mL) was stirred under reflux under hydrogen overnight. After cooling to room temperature and filtering, the filter cake was washed with a small amount of ethyl acetate. The solvent was evaporated under reduced pressure and the product was purified by column chromatography (200~300 mesh silica gel, methanol:dichloromethane=1:50-1:20 elution) to give (2R,3S)-4-amino-2-{(2R,3R)-3-(4-hydroxy-3-methoxyphenyl)-2-hydroxymethyl-2,3-dihydrobenzo[b][1,4]dioxan-6-yl}chroman-3,5,7-triol (47). $^1$H NMR (DMSO-$d_6$, 400 MHz) δ 9.27-9.02 (m, 3H), 7.03-6.81 (m, 7H), 5.78-5.64 (m, 3H), 5.18-5.14 (m, 1H), 4.96-4.90 (m, 3H), 4.61-4.59 (m, 1H), 4.18-4.13 (m, 1H), 3.80-3.63 (m, 3H), 3.61-3.53 (m, 3H). MS (EI, m/z): 482.2 [M–H]$^-$.

Example 9: Synthesis of (2R,3S)-2-{(2R,3R)-2-hydroxymethyl-3-[3-methoxy-4-(trideuteromethoxy)phenyl]-2,3-dihydrobenzo[b][1,4]dioxan-6-yl}-5,7-bis(trideuteromethoxy)chroman-3-ol (55)

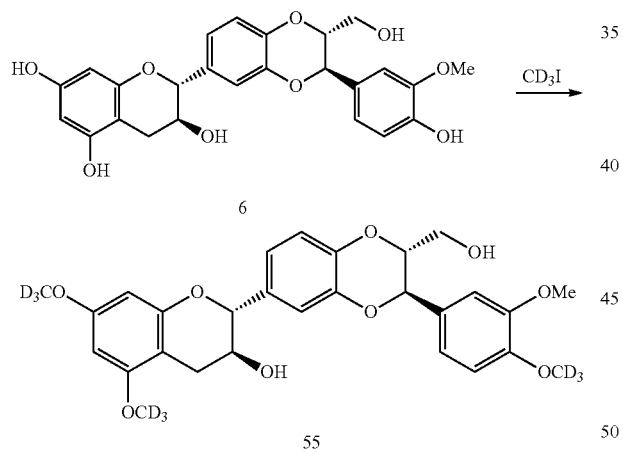

A mixture containing compound 6 (110 mg, 0.235 mmol), potassium carbonate (195 mg, 1.41 mmol), deuterated methyl iodide (136 mg, 0.938 mmol) and DMF (5 mL) was stirred at room temperature overnight. After adding water (20 mL), extraction was performed with ethyl acetate (20 mL×3), and the combined organic phase was washed with saturated brine (10 mL×2), and dried over anhydrous sodium sulfate. The solvent was evaporated under reduced pressure and the product was purified by column chromatography (200-300 mesh silica gel, ethyl acetate:THF:dichloromethane=1:1:40-1:1:20 elution) to give (2R,3S)-2-{(2R,3R)-2-hydroxymethyl-3-[3-methoxy-4-(trideuteromethoxy)phenyl]-2,3-dihydrobenzo[b][1,4]dioxan-6-yl}-5,7-bis(trideuteromethoxy)chroman-3-ol (55). $^1$H NMR (DMSO-$d_6$, 400 MHz) δ 7.03-6.86 (m, 6H), 6.11 (d, J=2.4 Hz, 1H), 6.03 (d, J=2.4 Hz, 1H), 5.05 (d, J=5.2 Hz, 1H), 4.97-4.92 (m, 2H), 4.69-4.66 (m, 1H), 4.19-4.15 (m, 1H), 3.97-3.92 (m, 1H), 3.82-3.74 (m, 4H), 3.55-3.51 (m, 1H), 2.69-2.65 (m, 1H), 2.46-2.40 (m, 1H). MS (ESI, m/z): 518.3 [M–H]$^-$.

Example 10: Synthesis of 2-{8-hydroxy-3-(4-hydroxy-3-methoxyphenyl)-2-hydroxymethyl-2,3-dihydrobenzo[b][1,4]dioxan-6-yl}-7-methoxy-chroman-3,4,5-triol (66)

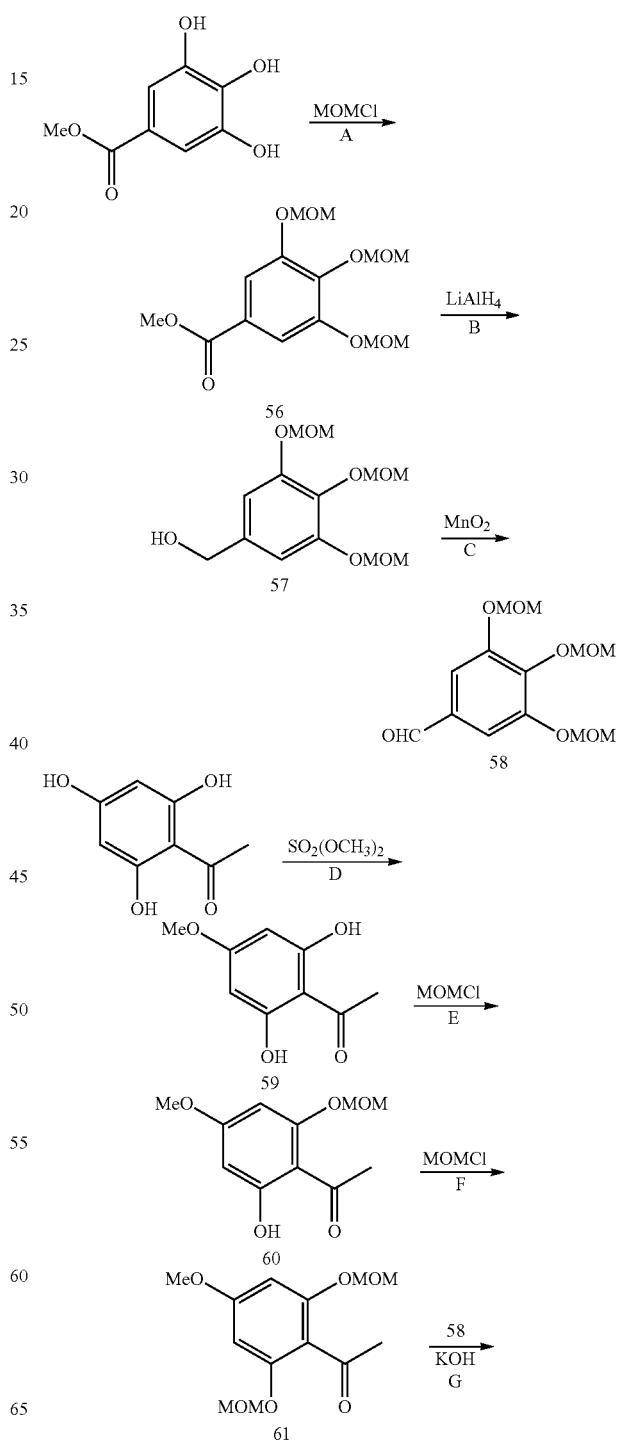

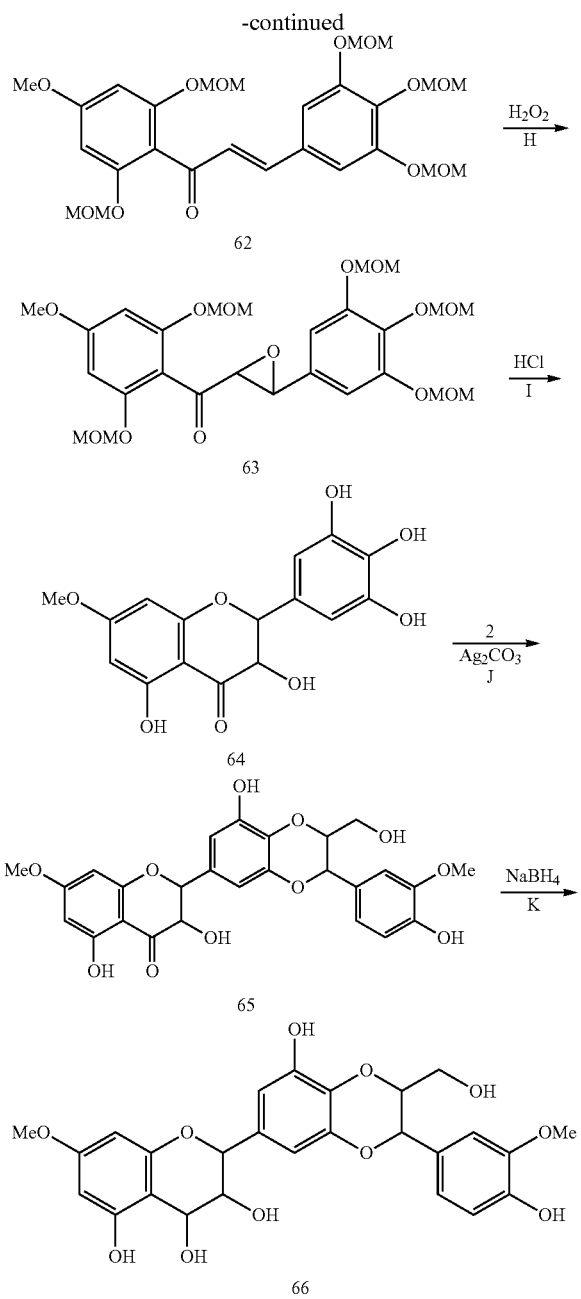

Step B: Lithium tetrahydroaluminum (2.88 g, 75.9 mmol) was suspended in THF, a solution of compound 56 (20.0 g, 63.2 mmol) in THF was slowly added under an ice-salt bath, and after the addition, the stirring was continued for 40 minutes at this temperature. Water (3 mL), 10% sodium hydroxide solution (6 mL) and water (9 mL) in sequence were added dropwise to the reaction solution, stirred for 10 minutes, filtered through celite, and dried over anhydrous sodium sulfate. The solvent was evaporated under reduced pressure to give (3,4,5-trimethoxymethoxyphenyl)methanol (57) (18.1 g) with a yield of 99.5%.

Step C: A mixture containing compound 57 (18.0 g, 62.4 mmol), chloroform (150 mL) and manganese dioxide (27.3 g, 312 mmol) was stirred overnight at 43° C., the reaction solution was filtered through a pad of celite, The filter residue was rinsed with dichloromethane, and the solvent was evaporated under reduced pressure to give 3,4,5-trimethoxymethoxy-benzaldehyde (58) (17.9 g) with a yield of 100%.

Step D: A mixture containing 2,4,6-trihydroxyacetophenone (25.6 g, 149 mmol), potassium carbonate (20.6 g, 149 mmol), dimethyl sulfate (28.1 g, 223 mmol) and acetone (250 mL) was stirred under reflux for 2 hours. The reaction solution was cooled to room temperature, filtered to remove insolubles and the solvent was evaporated under reduced pressure. The product was purified by column chromatography (200-300 mesh silica gel, ethyl acetate:dichloromethane:petroleum ether=1:1:40-1:1:6). After elution, 1-(2,6-dihydroxy-4-methoxy-phenyl)ethanone (59) (8.51 g) was obtained. The yield was 31.4%.

Step E: Compound 59 (8.50 g, 46.7 mmol) and N,N-diisopropylethylamine (15.1 g, 117 mmol) were dissolve in dichloromethane (50 ml), then chloromethyl methyl ether (5.63 g, 70.0 mmol) was added dropwise under an ice water bath. After the addition, the temperature was raised to room temperature and the stirring was continued for 1 hour. Water (50 mL) was added, the layers were separated, the aqueous layer was washed with dichloromethane (30 mL). The combined organic phase was washed with saturated brine (50 mL) and dried over anhydrous sodium sulfate. The solvent was evaporated under reduced pressure and the product was purified by column chromatography (200-300 mesh silica gel, ethyl acetate:petroleum ether=1:40-1:20 elution) to give 1-(2-hydroxy-4-methoxy)-6-methoxymethoxy-phenyl)ethanone (60) (8.31 g), the yield was 78.6%.

Using compound 60 as a raw material, the experimental operation for synthesizing compound 64 was performed according to the preparation methods of steps B, K, L and M in Example 5 to give 3,5-dihydroxy-7-methoxy-2-(3,4,5-trihydroxy-phenyl)chroman-4-one (64) (1.70 g). $^1$H NMR (DMSO-$d_6$, 400 MHz) δ 11.86 (s, 1H), 8.96 (s, 2H), 8.24 (s, 1H), 6.45 (s, 2H), 6.10 (d, J=2.4 Hz, 1H), 6.07 (d, J=2.4 Hz, 1H), 5.84 (d, J=6.4 Hz, 1H), 4.95 (d, J=10.8 Hz, 1H), 4.49-4.45 (m, 1H), 3.78 (s, 3H).

Using compound 64 as a raw material, the experimental operation for synthesizing compound 65 was performed according to the preparation method of step C in Example 1 to give 3,5-dihydroxy-2-{8-hydroxy-3-(4-hydroxy-3-methoxyphenyl)-2-hydroxymethyl-2,3-dihydrobenzo[b][1,4]dioxan-6-yl}-7-methoxychroman-4-one (65). $^1$H NMR (DMSO-$d_6$, 400 MHz) δ 11.85 (s, 1H), 9.23 (s, 1H), 9.16 (s, 1H), 7.00 (s, 1H), 6.86-6.77 (m, 2H), 6.11 (s, 1H), 6.09 (d, J=2.0 Hz, 1H), 5.87 (d, J=2.4 Hz, 1H), 5.04 (d, J=11.2 Hz, 1H), 4.87-4.85 (m, 2H), 4.60-4.56 (m, 1H), 4.14-4.10 (m, 1H), 3.79 (s, 3H), 3.78 (s, 3H), 3.51-3.44 (m, 3H).

Step A: Methyl gallate (30.0 g, 163 mmol) and N,N-diisopropylethylamine (126 g, 977 mmol) were dissolved in dichloromethane (120 mL), then chloromethyl methyl ether (52.5 g, 652 mmol) was added dropwise under an ice water bath, after the addition, the temperature was raised to room temperature the stirring was continued for 1.5 hours, water (240 mL) was added, the layers were separated, and the aqueous layer was extracted with dichloromethane (50 mL×2). The combined organic phase was washed with water (50 mL×2) and saturated brine (50 mL) in sequence, and dried over anhydrous sodium sulfate. The solvent was evaporated under reduced pressure, and the product was purified by column chromatography (200-300 mesh silica gel, ethyl acetate:dichloromethane:petroleum ether=1:1:10-1:1:6, elution) to give methyl 3, 4, 5-tri-methoxymethoxy-benzoate (56) (47.9 g). The yield was 93.0%.

Using compound 65 as a raw material, the experimental operation for synthesizing compound 66 was carried out according to the preparation method of step D in Example 1 to give 2-{8-hydroxy-3-(4-hydroxy-3-methoxyphenyl)-2-hydroxymethyl-2,3-dihydrobenzo[b][1,4]dioxan-6-yl}-7-methoxy-chroman-3,4,5-triol (66). MS (ESI, m/z): 515.2 [M+H]$^+$.

Example 11: Synthesis of 2-{8-hydroxy-3-(4-hydroxy-3-methoxyphenyl)-2-hydroxymethyl-2,3-dihydrobenzo[b][1,4]dioxan-6-yl}-7-methoxychroman-3,5-diol (67)

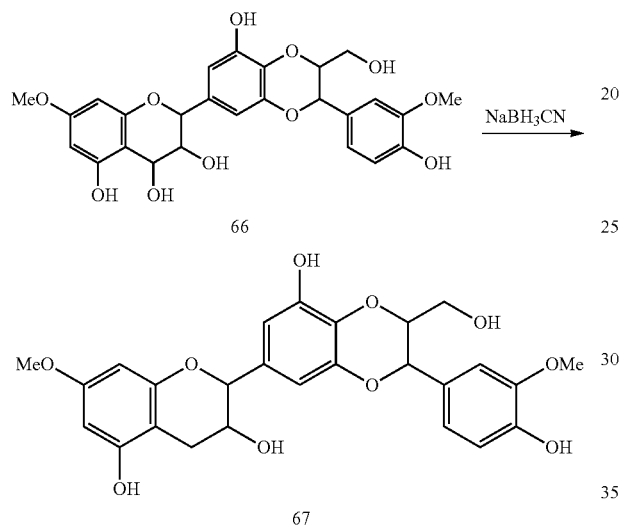

Using compound 66 as a raw material, the experimental operation for synthesizing compound 67 was carried out according to the preparation method of the procedure in Example 3 (67). $^1$H NMR (DMSO-d$_6$, 400 MHz) δ 9.39 (s, 1H), 9.13-9.09 (m, 2H), 6.98 (s, 1H), 6.85-6.76 (m, 2H), 5.98 (d, J=2.4 Hz, 1H), 5.89 (d, J=2.4 Hz, 1H), 4.98 (d, J=5.2 Hz, 1H), 4.84-4.80 (m, 2H), 4.58-4.56 (m, 1H), 4.10-4.07 (m, 1H), 3.90-3.85 (m, 1H), 3.78 (s, 3H), 3.62 (s, 3H), 3.49-3.45 (m, 1H), 3.41-3.38 (m, 1H), 2.66-2.61 (m, 1H), 2.43-2.37 (m, 1H). MS (ESI, m/z): 499.2 [M+H]$^+$.

Example 12: Synthesis of 7-{(3-hydroxy-5,7-dimethoxychroman-2-yl)-2-(4-hydroxy-3-methoxyphenyl)-3-hydroxymethyl-2,3-dihydrobenzo[b][1,4]dioxane}-5-ol (78)

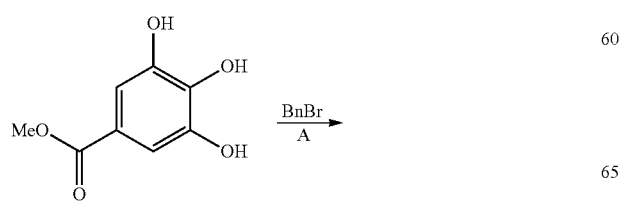

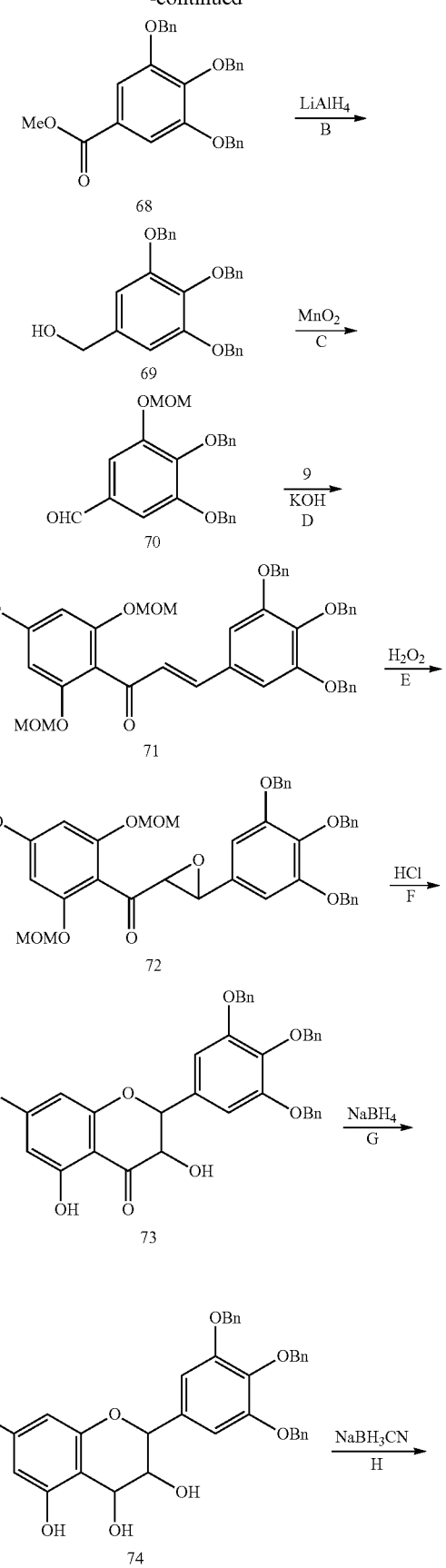

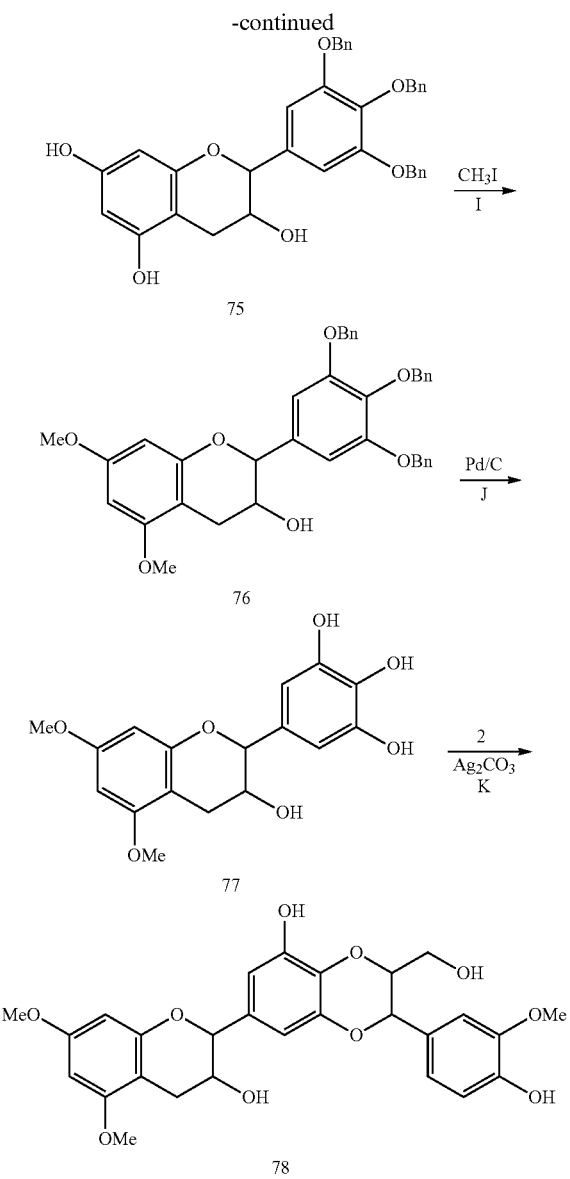

δ 11.92 (s, 1H), 10.90 (s, 1H), 7.50-7.26 (m, 15H), 7.06 (s, 2H), 5.94 (d, J=2.0 Hz, 1H), 5.17-5.09 (m, 6H), 4.95 (s, 2H), 4.76-4.72 (m, 1H).

Using compound 73 as a raw material, the experimental operation for synthesizing compound 74 was performed according to the preparation method of step D in Example 1 to give 2-(3,4,5-tribenzyloxy-phenyl)chroman-3,4,5,7-tetraol (74).

Using compound 74 as a raw material, the experimental operation for synthesizing compound 75 was carried out according to the preparation method of Example 3 to give 2-(3,4,5-tribenzyloxy-phenyl)chroman-3,5,7-triol (75).

Step I: A mixture of compound 75 (1.10 g, 1.91 mmol), potassium carbonate (792 mg, 5.72 mmol), methyl iodide (682 mg, 4.77 mmol) and DMF (25 mL) was stirred at room temperature overnight. Water (50 ml) was added, extraction was performed with ethyl acetate (25 ml×2) and the combined organic phase was washed with water (50 mL×2) and saturated brine (50 mL) in sequence and dried over anhydrous sodium sulfate. The solvent was evaporated under reduced pressure and the product was purified by column chromatography (200-300 mesh silica gel, ethyl acetate: dichloromethane:petroleum ether=1:1:20-1:1:8 elution) to give 5,7-dimethoxy-2-(3,4,5-tribenzyloxyphenyl)chroman-3-ol (76) (1.00 g), the yield was 86.7%.

Using compound 76 as a raw material, the experimental operation for synthesizing compound 77 was carried out according to the preparation method of step G in Example 5 to give 5-(3-hydroxy-5,7-dimethoxy-chroman-2-yl)-benzene-1,2,3-triol (77) (500 mg), the yield was 91.4%. $^1$H NMR (DMSO-d$_6$, 400 MHz) δ 8.79 (s, 2H), 8.03 (s, 1H), 6.25 (s, 2H), 6.10 (d, J=2.4 Hz, 1H), 6.02 (d, J=2.4 Hz, 1H), 5.95 (d, J=4.8 Hz, 1H), 4.53 (d, J=6.8 Hz, 1H), 3.87-3.81 (m, 1H), 3.73 (s, 3H), 3.69 (s, 3H), 2.65-2.59 (m, 1H), 2.44-2.38 (m, 1H).

Using compound 77 as a raw material, the experimental operation for synthesizing compound 78 was performed in accordance with the preparation method of step C in Example 1 to give 7-(3-hydroxy-5,7-dimethoxy-chroman-2-yl)-2-(4-hydroxy-3-methoxy-phenyl)-3-hydroxymethyl-2,3-dihydrobenzo[b][1,4]dioxan-5-ol (78). $^1$H NMR (DMSO-de, 400 MHz) δ 9.17-9.15 (m, 2H), 6.97 (s, 1H), 6.84-6.78 (m, 2H), 6.42 (d, J=2.0 Hz, 1H), 6.33 (d, J=2.0 Hz, 1H), 6.15 (d, J=2.0 Hz, 1H), 6.03 (d, J=2.0 Hz, 1H), 5.05 (d, J=4.8 Hz, 1H), 4.87-4.81 (m, 2H), 4.61 (d, J=6.8 Hz, 1H), 4.10-4.06 (m, 1H), 3.77 (s, 3H), 3.73 (s, 3H), 3.68 (s, 3H), 3.57-3.51 (m, 2H), 2.64-2.58 (m, 1H), 2.45-2.39 (m, 1H). MS (ESI, m/z): 513.2 [M+H]$^+$.

Example 13: Synthesis of 2-{8-hydroxy-3-(4-hydroxy-3-methoxyphenyl)-2-hydroxymethyl-2,3-dihydrobenzo[b][1,4]dioxan-6-yl}-5-methoxychroman-3,7-diol (85)

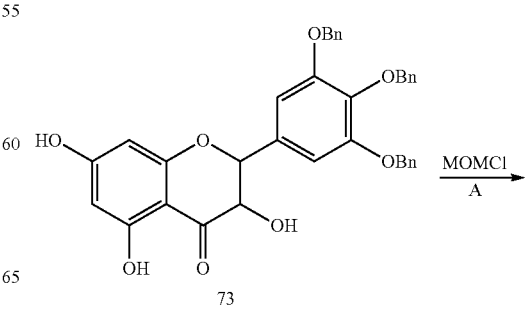

Step A: A mixture containing methyl gallate (20.0 g, 109 mmol), potassium carbonate (90.1 g, 652 mmol), DMF (120 mL) and benzyl bromide (74.3 g, 434 mmol) was stirred at 40° C. overnight. After adding water (240 mL), extraction was performed with dichloromethane (120 mL×2), and the combined organic phase was washed with water (50 mL×2) and saturated brine (50 mL) in sequence, and dried over anhydrous sodium sulfate. The solvent was evaporated under reduced pressure to give methyl 3,4,5-tribenzyloxy-benzoate (68) (46.5 g) with a yield of 94.2%.

Using compound 68 as a raw material, the experimental operation for synthesizing compound 70 was carried out in accordance with the preparation methods of steps B and C in Example 10 to give 3,4,5-tris-benzyloxy-benzaldehyde (70).

Using compound 70 as a raw material, the experimental operation for synthesizing compound 73 was carried out according to the preparation method of steps K, L and M in Example 5 to give 3,5,7-trihydroxy-2-(3,4,5-tribenzyloxy)-phenyl)chroman-4one (73). $^1$H NMR (DMSO-d$_6$, 400 MHz)

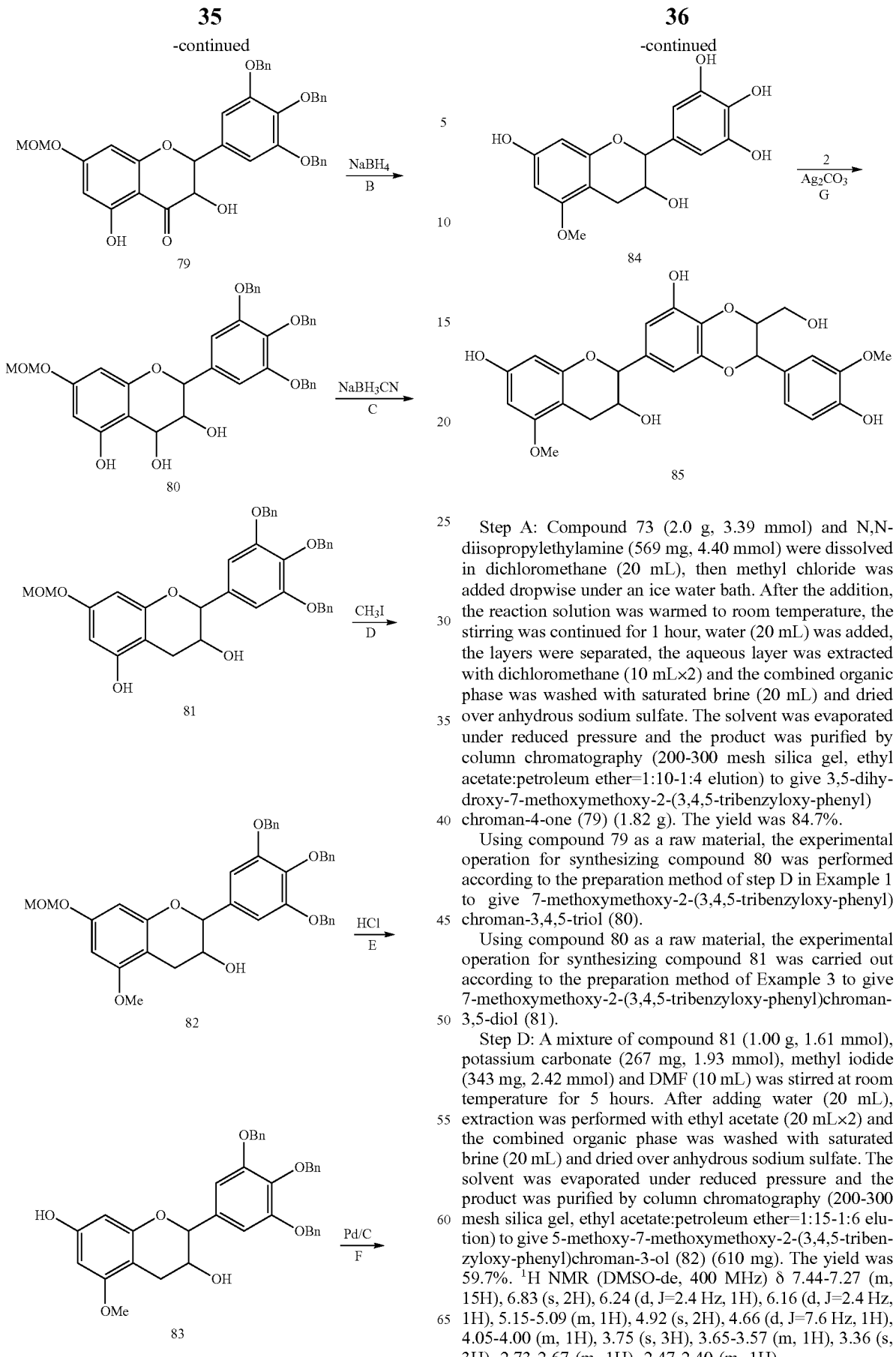

Step A: Compound 73 (2.0 g, 3.39 mmol) and N,N-diisopropylethylamine (569 mg, 4.40 mmol) were dissolved in dichloromethane (20 mL), then methyl chloride was added dropwise under an ice water bath. After the addition, the reaction solution was warmed to room temperature, the stirring was continued for 1 hour, water (20 mL) was added, the layers were separated, the aqueous layer was extracted with dichloromethane (10 mL×2) and the combined organic phase was washed with saturated brine (20 mL) and dried over anhydrous sodium sulfate. The solvent was evaporated under reduced pressure and the product was purified by column chromatography (200-300 mesh silica gel, ethyl acetate:petroleum ether=1:10-1:4 elution) to give 3,5-dihydroxy-7-methoxymethoxy-2-(3,4,5-tribenzyloxy-phenyl) chroman-4-one (79) (1.82 g). The yield was 84.7%.

Using compound 79 as a raw material, the experimental operation for synthesizing compound 80 was performed according to the preparation method of step D in Example 1 to give 7-methoxymethoxy-2-(3,4,5-tribenzyloxy-phenyl) chroman-3,4,5-triol (80).

Using compound 80 as a raw material, the experimental operation for synthesizing compound 81 was carried out according to the preparation method of Example 3 to give 7-methoxymethoxy-2-(3,4,5-tribenzyloxy-phenyl)chroman-3,5-diol (81).

Step D: A mixture of compound 81 (1.00 g, 1.61 mmol), potassium carbonate (267 mg, 1.93 mmol), methyl iodide (343 mg, 2.42 mmol) and DMF (10 mL) was stirred at room temperature for 5 hours. After adding water (20 mL), extraction was performed with ethyl acetate (20 mL×2) and the combined organic phase was washed with saturated brine (20 mL) and dried over anhydrous sodium sulfate. The solvent was evaporated under reduced pressure and the product was purified by column chromatography (200-300 mesh silica gel, ethyl acetate:petroleum ether=1:15-1:6 elution) to give 5-methoxy-7-methoxymethoxy-2-(3,4,5-tribenzyloxy-phenyl)chroman-3-ol (82) (610 mg). The yield was 59.7%. $^1$H NMR (DMSO-d$_6$, 400 MHz) δ 7.44-7.27 (m, 15H), 6.83 (s, 2H), 6.24 (d, J=2.4 Hz, 1H), 6.16 (d, J=2.4 Hz, 1H), 5.15-5.09 (m, 1H), 4.92 (s, 2H), 4.66 (d, J=7.6 Hz, 1H), 4.05-4.00 (m, 1H), 3.75 (s, 3H), 3.65-3.57 (m, 1H), 3.36 (s, 3H), 2.73-2.67 (m, 1H), 2.47-2.40 (m, 1H).

Step E: A mixture of compound 82 (580 mg, 0.914 mmol), methanol (6 mL), tetrahydrofuran (2 mL) and concentrated hydrochloric acid (2 mL) was stirred at 40° C. for 30 minutes. Water (20 mL) was added, extraction was performed with ethyl acetate (20 mL×2), and the combined organic phase was washed with saturated brine (20 mL) and dried over anhydrous sodium sulfate. The solvent was evaporated under reduced pressure to give 5-methoxy-2-(3,4,5-tribenzyloxy-phenyl)chroman-3,7-diol (83) (510 mg). The yield was 98.1%.

Using compound 83 as a raw material, the experimental operation for synthesizing compound 84 was carried out according to the preparation method of step G in Example 5 to give 5-(3,7-dihydroxy-5-methoxychroman-2-yl)benzene-1,2,3-triol (84).

Using compound 84 as a raw material, the experimental operation for synthesizing compound 85 was performed according to the preparation method of step C in Example 1 to give 2-{8-hydroxy-3-(4-hydroxy-3-methoxyphenyl)-2-hydroxymethyl-2,3-dihydrobenzo[b][1,4]dioxan-6-yl}-5-methoxychroman-3,7-diol (85). $^1$H NMR (DMSO-$d_6$, 400 MHz) δ 9.23 (s, 1H), 9.15 (s, 1H), 9.12 (s, 1H), 6.97 (s, 1H), 6.84-6.75 (m, 2H), 6.41 (d, J=2.0 Hz, 1H), 6.33 (d, J=2.0 Hz, 1H), 5.97 (d, J=2.4 Hz, 1H), 5.85 (d, J=2.4 Hz, 1H), 4.98 (d, J=4.8 Hz, 1H), 4.83-4.10 (m, 2H), 4.55 (d, J=6.8 Hz, 1H), 4.09-4.05 (m, 1H), 3.88-3.84 (m, 1H), 3.83 (s, 3H), 3.77 (s, 3H), 3.68-3.66 (m, 1H), 3.50-3.48 (m, 1H), 2.63-2.55 (m, 1H), 2.40-2.34 (m, 1H). MS (ESI, m/z): 497.2 [M−H]$^-$.

Example 14: Synthesis of 2-{8-hydroxy-3-(4-hydroxy-3-methoxyphenyl)-2-hydroxymethyl-2,3-dihydrobenzo[b][1,4]dioxan-6-yl}-5,7-dimethoxychroman-3,4-diol (92)

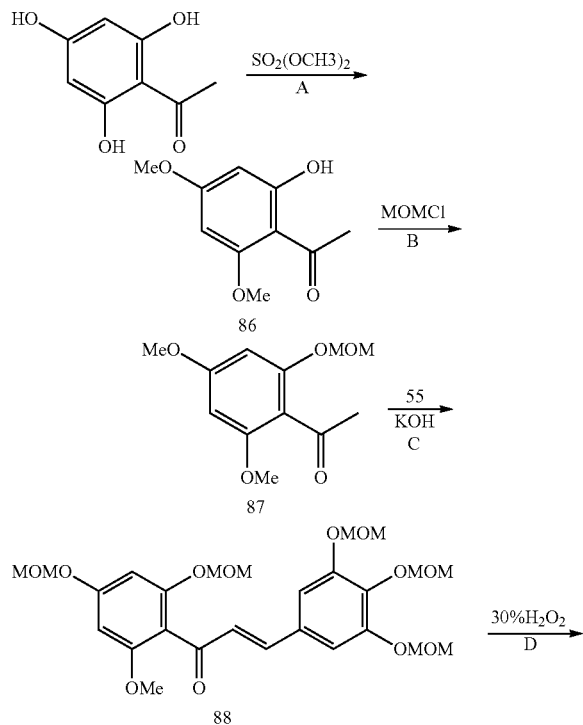

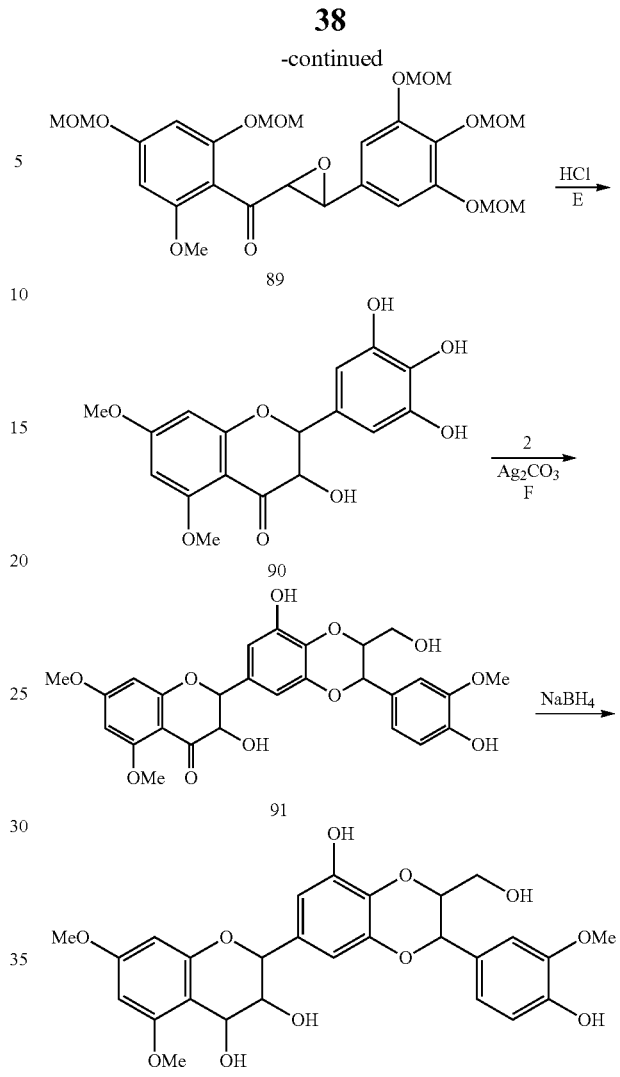

Step A: A mixture containing 2,4,6-trihydroxyacetophenone (25.0 g, 149 mmol), potassium carbonate (20.6 g, 149 mmol), dimethyl sulfate (28.1 g, 223 mmol) and acetone (250 mL) was stirred under reflux for 2 hours. The reaction solution was cooled to room temperature, filtered to remove insolubles, the solvent was evaporated under reduced pressure, and the product was purified by column chromatography (200-300 mesh silica gel, ethyl acetate:dichloromethane:petroleum ether=1:1:40-1:1:6). After elution, 1-(4-hydroxy-2,6-methoxy-phenyl)ethanone (86) (16.0 g) was obtained with a yield of 54.9%.

Using compound 86 as a raw material, the experimental operation for synthesizing compound 91 was performed according to the preparation method of step D in Example 1 to give 3-hydroxy-2-{8-hydroxy-3-(4-hydroxy-3-methoxyphenyl)-2-hydroxymethyl-2,3-dihydrobenzo[b][1,4]dioxan-6-yl}-5,7-dimethoxychroman-4-one (91). $^1$H NMR (DMSO-$d_6$, 400 MHz) δ 9.19 (s, 1H), 9.15 (s, 1H), 7.00 (s, 1H), 6.86-6.76 (m, 2H), 6.56 (d, J=2.4 Hz, 1H), 6.52 (d, J=2.4 Hz, 1H), 6.21 (d, J=2.4 Hz, 1H), 6.17 (d, J=2.4 Hz, 1H), 5.36 (d, J=4.8 Hz, 1H), 4.97-4.85 (m, 2H), 4.29-4.26 (m, 1H), 4.11-4.09 (m, 1H), 3.80 (s, 3H), 3.79 (s, 3H), 3.77 (s, 3H), 3.51-3.49 (m, 1H), 3.47-3.46 (m, 1H). MS (ESI, m/z): 549.2 [M+Na]$^+$.

Using compound 91 as a raw material, the experimental operation for synthesizing compound 92 was performed according to the preparation method of step D in Example 1 to give 2-{8-hydroxy-3-(4-hydroxy-3-methoxyphenyl)-2-hydroxymethyl-2,3-dihydrobenzo[b][1,4]dioxan-6-yl}-5,7-dimethoxychroman-3,4-diol (92). $^1$H NMR (DMSO-$d_6$, 400 MHz) δ 9.15 (s, 1H), 9.10 (s, 1H), 6.99 (s, 1H), 6.85-6.75 (m, 2H), 6.46 (d, J=2.0 Hz, 1H), 6.36 (d, J=2.0 Hz, 1H), 6.14 (d, J=2.4 Hz, 1H), 6.02 (d, J=2.4 Hz, 1H), 5.18 (d, J=5.6 Hz, 1H), 4.90-4.81 (m, 2H), 4.60-4.58 (m, 2H), 4.50 (d, J=4.4 Hz, 1H), 4.09-4.06 (m, 1H), 3.77 (s, 3H), 3.75 (s, 3H), 3.70 (s, 3H), 3.46-3.43 (m, 3H). MS (ESI, m/z): 551.2 [M+Na]$^+$.

Example 15: Synthesis of 7-fluoro-2-{8-hydroxy-3-(4-hydroxy-3-methoxyphenyl)-2-hydroxymethyl-2,3-dihydrobenzo[b][1,4]dioxan-6-yl}chroman-3,4,5-triol (101)

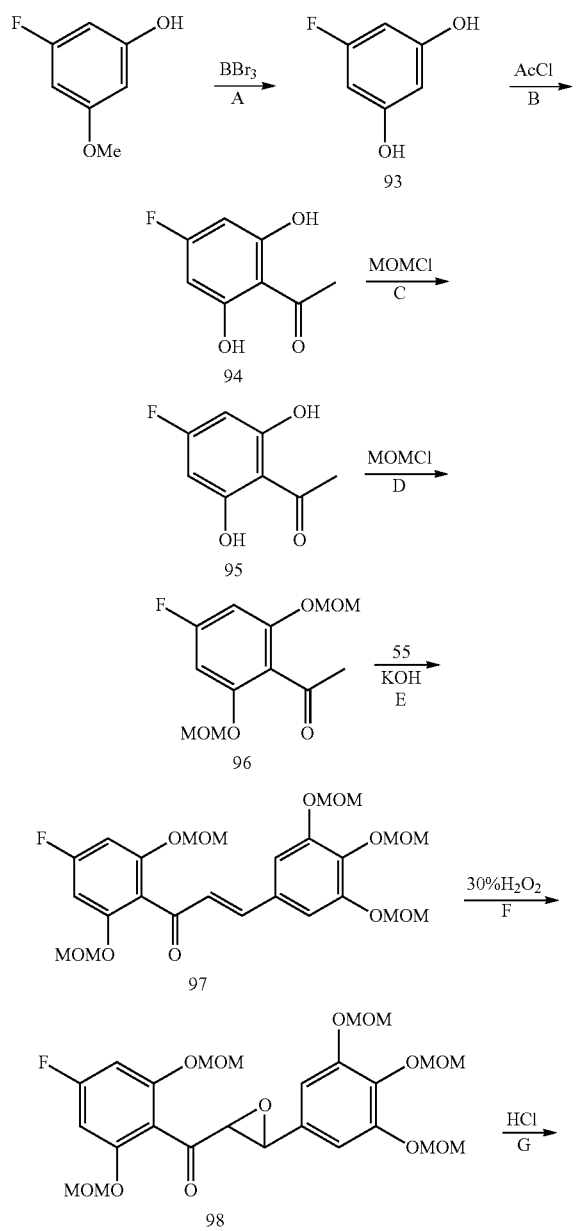

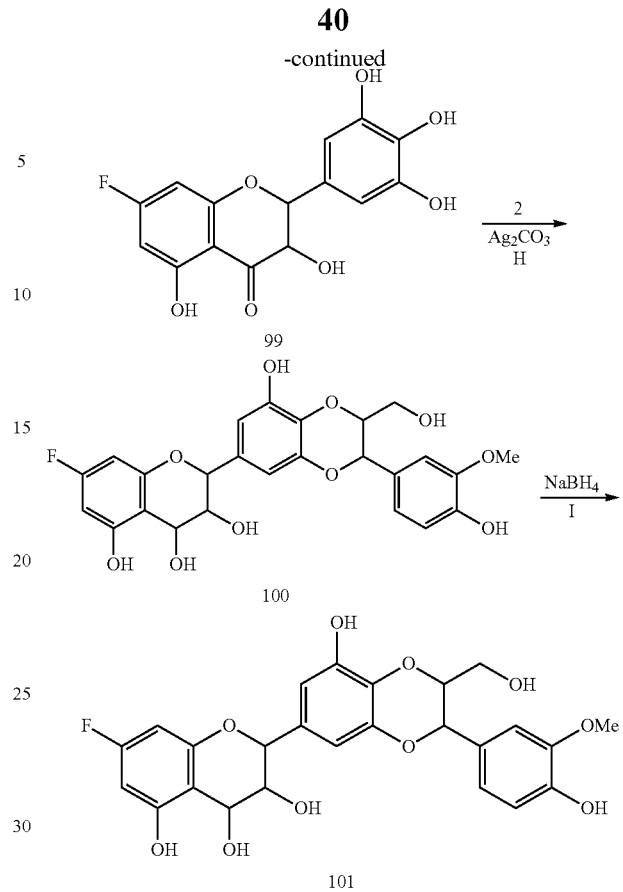

Step A: The compound 1,3-dimethoxy-5-fluorobenzene (6.50 g, 41.6 mmol) was dissolved in dichloromethane (65 ml) and boron tribromide (24.0 g, 24.0 g, 95.7 mmol) was added dropwise ander an ice water bath. After the addition, the reaction solution was warmed to room temperature and the stirring was continued overnight. The reaction solution was added dropwise to ice water, the pH value was adjusted to 7-8 with saturated sodium bicarbonate solution, extraction was performed with ethyl acetate (100 mL×2), and the combined organic phase was washed with saturated brine (100 mL) and dried over unhydrous sodium sulfate. The solvent was evaporated under reduced pressure, and the product was purified by column chromatography (200~300 mesh silica gel, ethyl acetate:petroleum ether=1:20-1:10 elution) to give 5-fluorobenzene-1,3-diol (93) (4.82 g). The yield was 90.4%.

Step B: A mixture of compound 93 (4.80 g, 37.5 mmol), aluminum trichloride (15.0 g, 112 mmol) and chlorobenzene (50 ml) was stirred at 45° C. for 10 minutes. Acetyl chloride (4.12 g, 52.5 mmol) was slowly added dropwise to the reaction system and stirred overnight at 75° C. The reaction system was added dropwise to ice water, the pH was adjusted to 3-4 with 2 M hydrochloric acid, ethyl acetate (60 ml×2) was added for extraction, and the combined organic phase was washed with saturated brine (60 mL), and dried over anhydrous sodium sulfate. The solvent was evaporated under reduced pressure, and the product was purified by column chromatography (200-300 mesh silica gel, ethyl acetate:petroleum ether=1:40-1:20 elution) to give 1-(4-fluoro-2,6-dihydroxy-phenyl)ethanone (94) (2.48 g). The yield was 38.9%.

Using compound 94 as a raw material, the experimental operation for synthesizing compound 101 was performed according to the preparation method of steps E, F, G, H, I, J and K in Example 10 to give 7-fluoro-2-{8-hydroxy-3-(4-hydroxy-3-methoxyphenyl)-2-hydroxymethyl-2,3-dihydrobenzo[b][1,4]dioxan-6-yl}chroman-3,4,5-triol (101). $^1$H NMR (DMSO-d$_6$, 400 MHz) δ 9.91 (br, 1H), 9.21 (br, 2H), 6.98 (s, 1H), 6.94-6.76 (m, 2H), 6.48 (d, J=1.2 Hz, 1H), 6.39 (d, J=1.2 Hz, 1H), 6.22-6.19 (m, 1H), 6.14-6.11 (m, 1H), 5.32-5.31 (d, J=6.0 Hz, 1H), 4.83 (d, J=8.0 Hz, 1H), 4.72 (d, J=6.8 Hz, 1H), 4.64 (d, J=8.8 Hz, 1H), 4.10-4.07 (m, 1H), 3.77 (s, 3H), 3.74-3.65 (m, 2H), 3.54-3.52 (m, 1H). MS (ESI, m/z): 501.2 [M−H]$^-$.

Example 16: Synthesis of 7-ethoxy-2-{8-hydroxy-3-(4-hydroxy-3-methoxyphenyl)-2-hydroxymethyl-2,3-dihydrobenzo[b][1,4]dioxan-6-yl}chroman-3,5-diol (105)

Step A: A mixture containing compound 81 (750 mg, 1.21 mmol), potassium carbonate (217 mg, 1.57 mmol), benzyl bromide (310 mg, 1.81 mmol) and DMF (10 mL) was stirred at room temperature overnight. After adding water (20 mL), extraction was performed with ethyl acetate (20 mL×2), and the combined organic phase was washed with saturated brine (20 mL) and dried over anhydrous sodium sulfate. The solvent was evaporated under reduced pressure, and the product was purified by column chromatography (200-300 mesh silica gel, ethyl acetate:petroleum ether=1:10-1:5 elution) to give 5-benzyloxy-7-methoxymethoxy-2-(3,4,5-tribenzyloxy-phenyl)chroman-3-ol (102) (640 mg). The yield was 74.5%.

Using compound 102 as a raw material, the experimental operation for synthesizing compound 105 was performed according to the preparation method of steps E, F and G in Example 12 to give 7-ethoxy-2-{8-hydroxy-3-(4-hydroxy-3-methoxyphenyl)-2-hydroxymethyl-2,3-dihydrobenzo[b][1,4]dioxan-6-yl}chroman-3,5-diol (105). $^1$H NMR (DMSO-d$_6$, 400 MHz) δ 9.35 (s, 1H), 9.12 (s, 1H), 9.08 (s, 1H), 6.98 (s, 1H), 6.84-6.75 (m, 2H), 6.42 (d, J=2.0 Hz, 1H), 6.34 (d, J=2.0 Hz, 1H), 5.96 (d, J=2.4 Hz, 1H), 5.86 (d, J=2.4 Hz, 1H), 4.96 (d, J=5.2 Hz, 1H), 4.83-4.80 (m, 2H), 4.56 (d, J=7.2 Hz, 1H), 4.09-4.04 (m, 1H), 3.90-3.78 (m, 3H), 3.77 (s, 3H), 3.35-3.38 (m, 2H), 2.67-2.59 (m, 1H), 2.42-2.37 (m, 1H). MS (ESI, m/z): 511.3[M−H]$^-$.

Example 17: Synthesis of 5-ethoxy-2-{8-hydroxy-3-(4-hydroxy-3-methoxyphenyl)-2-hydroxymethyl-2,3-dihydrobenzo[b][1,4]dioxan-6-yl}chroman-3,7-diol (109)

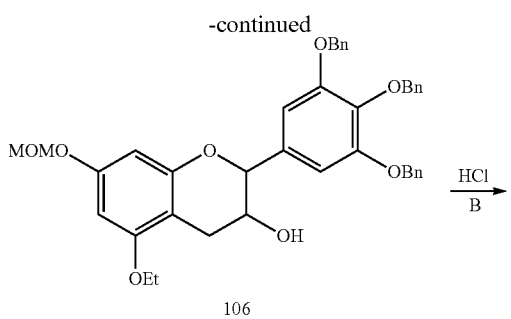
106

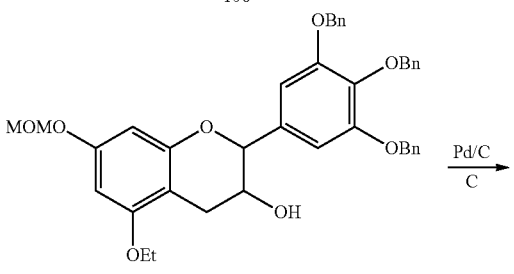
107

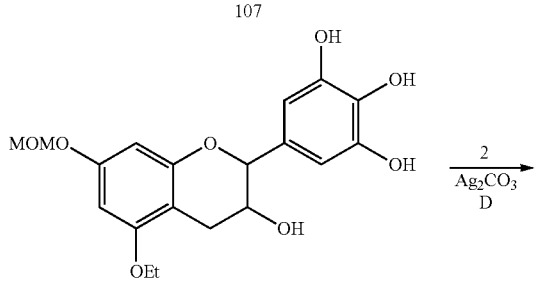
108

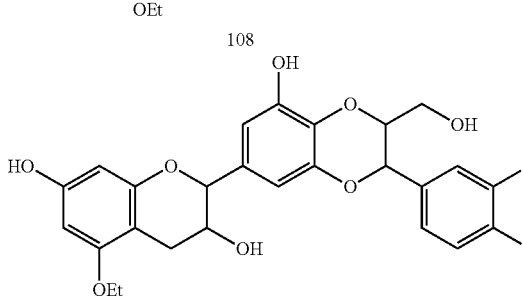
109

Step A: A mixture containing compound 81 (630 mg, 1.01 mmol), potassium carbonate (182 mg, 1.32 mmol), benzyl bromide (260 mg, 1.52 mmol) and DMF (10 mL) was stirred at room temperature overnight. After adding water (20 mL), extraction was performed with ethyl acetate (20 mL×2), and the combined organic phase was washed with saturated brine (20 mL) and dried over anhydrous sodium sulfate. The solvent was evaporated under reduced pressure and the product was purified by column chromatography (200-300 mesh silica gel, ethyl acetate:petroleum ether=1:10-1:5 elution) to give 5-ethoxy-7-methoxymethoxy-2-(3,4,5-tribenzyloxy-phenyl)chroman-3-ol (106) (620 mg). The yield was 94.2%.

Using compound 106 as a raw material, the experimental operation for synthesizing compound 109 was performed according to the preparation method of steps E, F and G in Example 12 to give 5-ethoxy-2-{8-hydroxy-3-(4-hydroxy-3-methyloxyphenyl)-2-hydroxymethyl-2,3-dihydrobenzo[b][1,4]dioxan-6-yl}chroman-3,7-diol (109). ¹H NMR (DMSO-d₆, 400 MHz) δ 9.30 (s, 1H), 9.23 (s, 1H), 9.05 (s, 1H), 7.21 (s, 1H), 7.08-7.07 (m, 1H), 6.97 (s, 1H), 6.94-6.85 (m, 2H), 5.97 (d, J=2.4 Hz, 1H), 5.77 (d, J=2.4 Hz, 1H), 5.08 (d, J=5.6 Hz, 1H), 5.08-5.01 (m, 2H), 4.61 (d, J=7.6 Hz, 1H), 4.35-4.30 (m, 1H), 3.94-3.88 (m, 1H), 3.83 (s, 3H), 3.69-3.67 (m, 1H), 3.65-3.43 (m, 1H), 2.79-2.74 (m, 1H), 2.45-2.39 (m, 1H). MS (ESI, m/z): 511.3 [M−H]⁻.

Example 18: Synthesis of 2-{8-bromo-3-(4-hydroxy-3-methoxyphenyl)-2-hydroxymethyl-2,3-dihydrobenzo[b][1,4]dioxane-6-yl}chroman-3,4,5,7-tetraol (117)

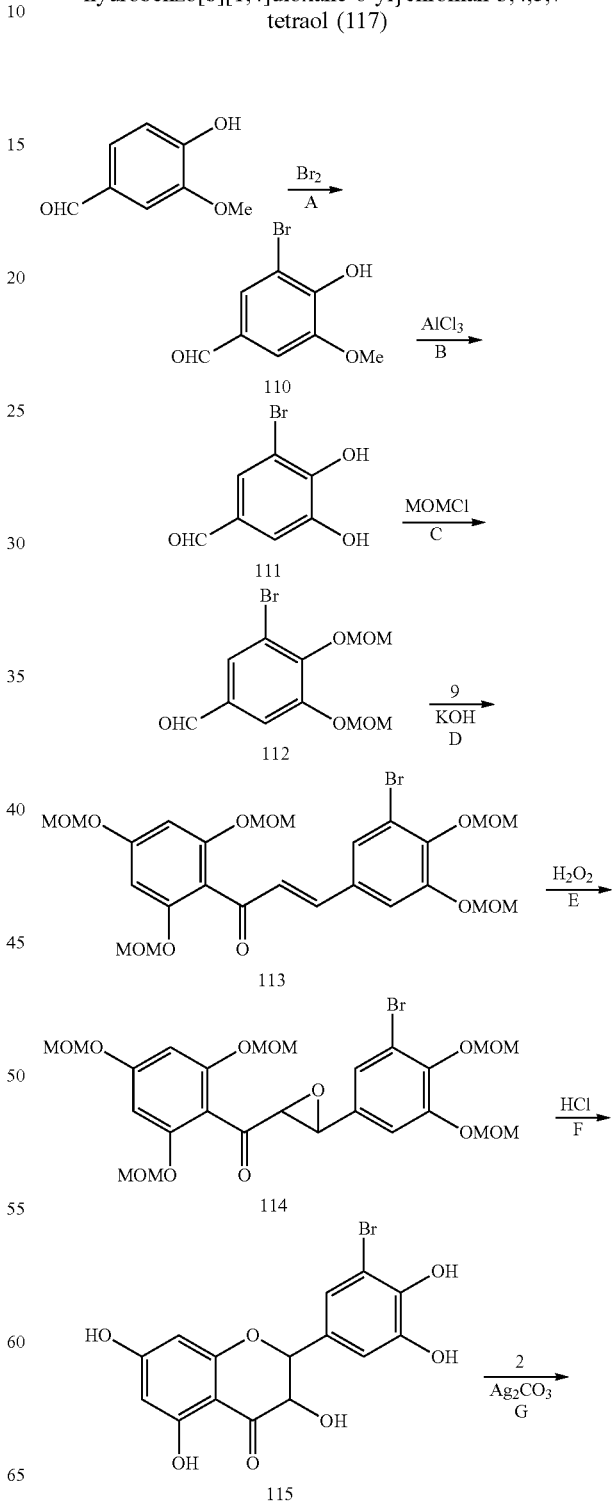

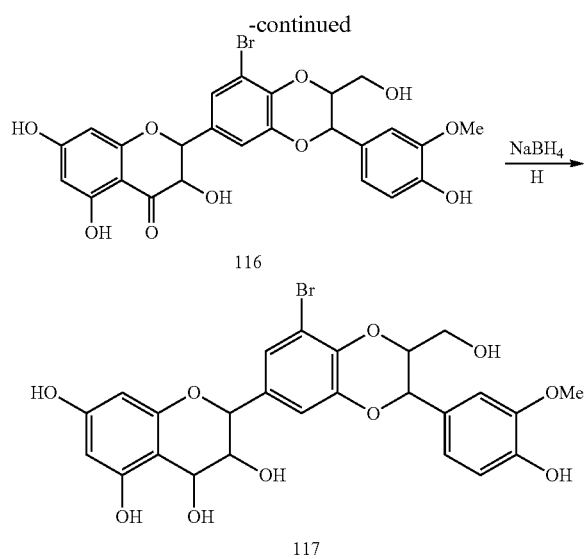

116

117

Step A: 3-methoxy-4-hydroxybenzaldehyde (5 g, 32.9 mmol) and sodium acetate (3.23 g, 39.4 mmol) were dissolved in acetic acid (25 ml), and a solution of bromine (5.78 g, 36.1 mmol) in acetic acid (5 mL) was added dropwise at room temperature. After the addition, the temperature was raised to room temperature and stirring was continued for 1.5 hours. A saturated solution of sodium sulfite (5 ml) and water (50 mL) were added to the reaction solution, which was filtered to give 3-bromo-4-hydroxy-5-methoxybenzaldehyde (110) (6.98 g). The yield was 92.0%

Step B: A mixture containing compound 110 (6.95 g, 30.1 mmol), aluminum trichloride (4.41 g, 33.1 mmol), pyridine (10.7 g, 135.4 mmol) and dichloromethane (50 mL) was stirred overnight under reflux. The solvent was evaporate under reduced pressure, water (50 mL) was added, the pH was adjusted to 3-4 with 2 M hydrochloric acid solution, extraction was performed with ethyl acetate (50 ml×2), and the combined organic phase was washed with saturated brine (50 mL) and dried over anhydrous sodium sulfate. The solvent was evaporated under reduced pressure to give 3-bromo-4,5-dihydroxybenzaldehyde (111) (6.50 g) with a yield of 99.5%.

Step C: Compound 111 (6.40 g, 30.1 mmol), N,N-diisopropylethylamine (11.4 g, 88.5 mmol) were dissolved in dry dichloromethane (50 mL), and chloromethyl methyl ether (5.93 g, 73.7 mmol) was added dropwise under an ice water bath. After the addition, the temperature was raised to room temperature and the stirring was continued for 1 hour. Water (50 mL) was added, the layers were separated, the aqueous layer was extracted with dichloromethane (50 mL), and the combined organic layer was washed with saturated brine (50 mL) and dried over anhydrous sodium sulfate. The solvent was evaporated under reduced pressure and the product was purified by column chromatography (200-300 mesh silica gel, ethyl acetate:petroleum ether=1:50-1:20 elution) to give 3-bromo-4,5-dimethoxymethoxybenzaldehyde (9.00 g) (112), The yield was 93.1%.

Using compound 112 as a raw material, the experimental operation for synthesizing compound 115 was performed according to the preparation method of steps K, L and M in Example 5 to give 2-(3-bromo-4,5-dihydroxyphenyl)-3, 5,7-trihydroxychroman-4-one (115) (2.6 g). The total yield of steps D, E and F was 23.0%.

Using compound 115 as a raw material, the experimental operation for synthesizing compound 116 was performed according to the preparation method of step C in Example 1 to give 2-{8-bromo-3-(4-hydroxy-3-methoxyphenyl)-2-hydroxymethyl-2,3-dihydrobenzo[b][1,4]dioxan-6-yl}-3,5,7-trihydroxychroman-4-one (116). $^1$H NMR (DMSO-d$_6$, 400 MHz) δ 11.94 (s, 1H), 10.94 (br, 1H), 9.26 (s, 1H), 7.40 (s, 1H), 7.19 (s, 1H), 7.09 (s, 1H), 6.95-6.86 (m, 2H), 5.97 (d, J=2.4 Hz, 1H), 5.94 (d, J=2.4 Hz, 1H), 5.16 (d, J=11.6 Hz, 1H), 5.05 (d, J=7.2 Hz, 1H), 4.74-4.68 (m, 1H), 4.40-4.36 (m, 1H), 3.84 (s, 3H), 3.71-3.66 (m, 1H), 3.55-3.52 (m, 1H). MS (ESI, m/z): 583.0[M+Na]$^+$.

Using compound 116 as a raw material, the experimental operation for synthesizing compound 117 was performed according to the preparation method of step D in Example 1 to give 2-{8-bromo-3-(4-hydroxy-3-methoxyphenyl)-2-hydroxymethyl-2,3-dihydrobenzo[b][1,4]dioxan-6-yl}chroman-3,4,5,7-tetraol. MS (ESI, m/z): 585.1 [M+Na]$^+$.

Example 19: Synthesis of 2-{8-bromo-3-(4-hydroxy-3-methoxyphenyl)-2-hydroxymethyl-2,3-dihydrobenzo[b][1,4]di oxan-6-yl}chroman-3,5,7-triol (118)

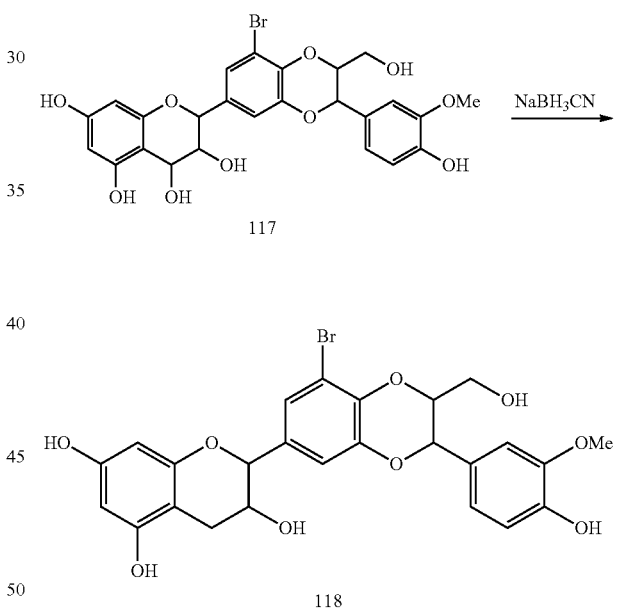

117

118

Using compound 117 as a raw material, the experimental operation for synthesizing compound 118 was performed in accordance with the preparation method in Example 3 to give 2-{8-bromo-3-(4-hydroxy-3-methoxyphenyl)-2-hydroxymethyl-2,3-dihydrobenzo[b][1,4]dioxan-6-yl}chroman-3,4,5,7-tetraol (118). $^1$H NMR (DMSO-d$_6$, 400 MHz) δ 9.30 (s, 1H), 9.23 (s, 1H), 9.05 (s, 1H), 7.21 (s, 1H), 7.07 (s, 1H), 7.06 (s, 1H), 6.98-6.85 (m, 2H), 5.97 (d, J=2.4 Hz, 1H), 5.77 (d, J=2.4 Hz, 1H), 5.08 (d, J=5.6 Hz, 1H), 5.03-5.01 (m, 2H), 4.61 (d, J=7.6 Hz, 1H), 4.35-4.30 (m, 1H), 3.94-3.88 (m, 1H), 3.83 (s, 1H), 3.69-3.65 (m, 1H), 2.79-2.74 (m, 1H), 2.45-2.39 (m, 1H). MS (ESI, m/z): 548.2 [M+Na]$^+$.

Example 20: Synthesis of 2-(4-hydroxy-3-methoxyphenyl)-3-hydroxymethyl-7-(3,5,7-trihydroxychroman-2-yl)-2,3-dihydrobenzo[b][1,4]dioxan-5-carbonitrile (119)

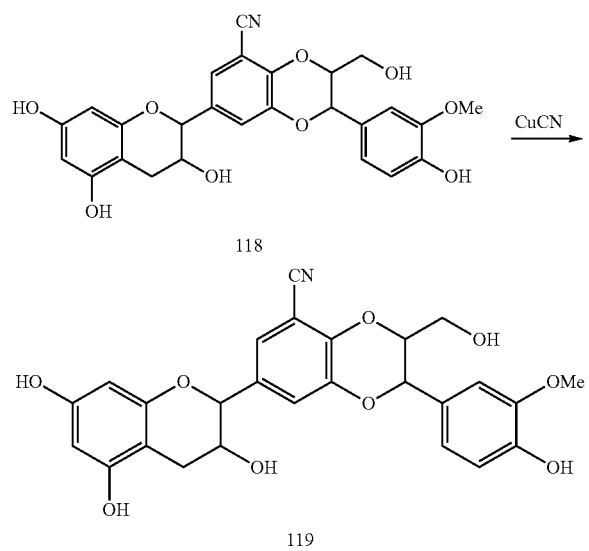

A mixture containing compound 118 (218 mg, 39.8 μmol), cuprous cyanide (39.2 mg, 43.8 μmol) and N-methylpyrrolidone (5 mL) was stirred at 150° C. for 2 hours. After cooling to room temperature, water (15 mL) was added. Extraction was performed with ethyl acetate (15 mL×2), and the combined organic phase was washed with saturated brine (20 mL), and dried over anhydrous sodium sulfate. The solvent was evaporated under reduced pressure and the product was purified by column chromatography (200-300 mesh silica gel, methanol:ethyl acetate:dichloromethane=1:100:100-1:50:50 elution) to give 2-(4-hydroxy-3-methoxyphenyl)-3-hydroxymethyl-7-(3,5,7-trihydroxychroman-2-yl)-2,3-dihydrobenzo[b][1,4]dioxan-5-carbonitrile (119). $^1$H NMR (DMSO-$d_6$, 400 MHz) δ 9.30 (s, 1H), 9.18 (s, 1H), 9.15 (s, 1H), 7.12 (s, 1H), 7.00 (s, 1H), 6.88-6.79 (m, 3H), 6.04 (d, J=2.0 Hz, 1H), 5.02-4.95 (m, 4H), 4.60-4.56 (m, 1H), 4.28-4.21 (m, 1H), 3.86-3.81 (m, 1H), 3.78 (s, 3H), 3.65-3.60 (m, 1H), 3.83 (s, 1H), 2.68-2.57 (m, 1H), 2.37-2.33 (m, 1H). MS (ESI, m/z): 494.1 [M+H]$^+$.

Example 21: Synthesis of (2R,3S)-2-{2-aminomethyl-(2R,3R)-3-(4-hydroxy-3-methoxyphenyl)-2,3-dihydrobenzo[b][1,4]dioxan-6-yl}chroman-3,5,7-triol (126)

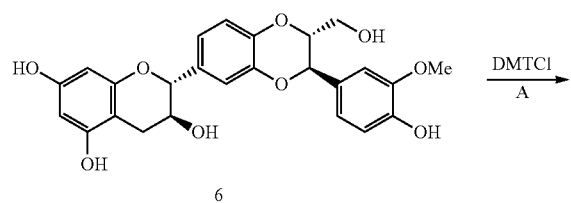

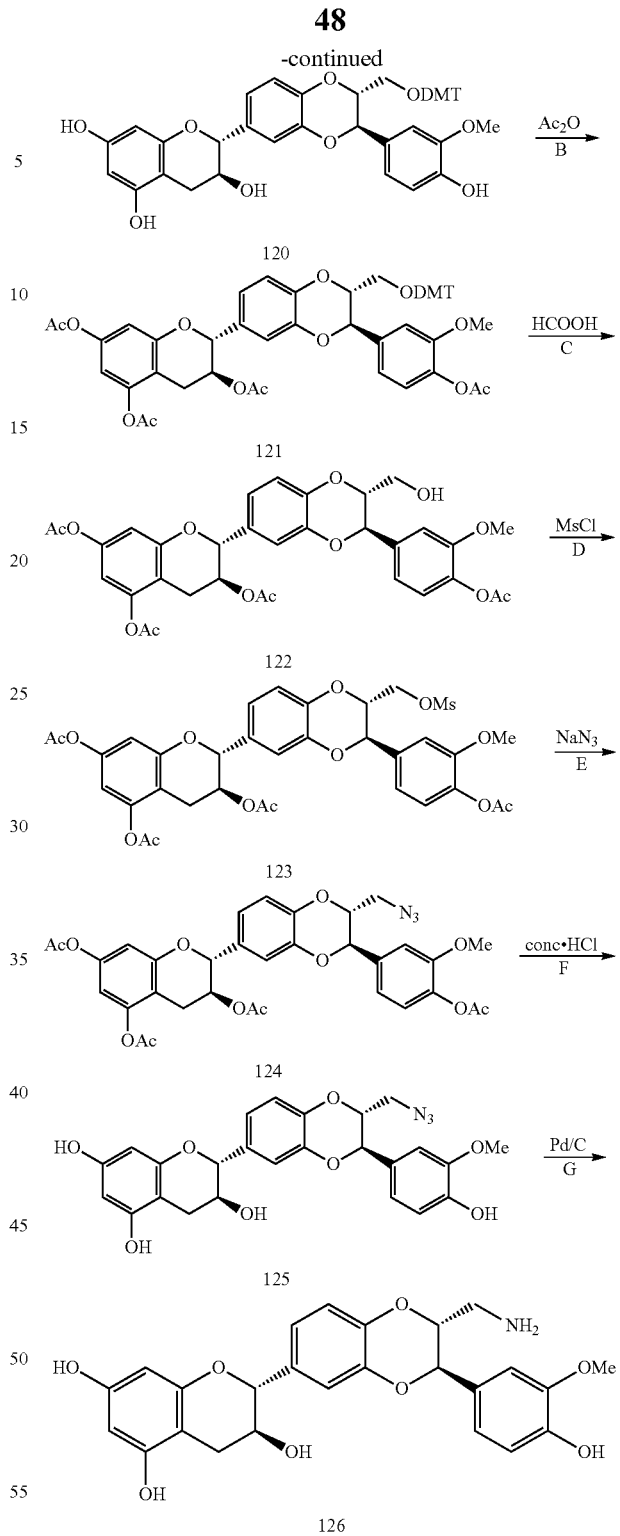

Step A: A mixture of compound 6 (1.50 g, 3.20 mmol), 4,4'-dimethoxytrityl chloride (DMTCl) (1.41 g, 4.16 mmol), DMAP (78.2 mg, 0.64 mmol), Et$_3$N (389 mg, 38.4 mmol) and pyridine (10 mL) was stirred at 100° C. overnight. Most of the pyridine was evaporated under reduced pressure. Ethyl acetate (20 mL×2) and water (20 mL) were added for extraction, and the combined organic phase was washed with saturated brine (20 mL) and dried over anhydrous sodium sulfate. The solvent was evaporated under reduced pressure and the product was purified by column chromatography (200-300 mesh silica gel, ethyl acetate:dichloromethane=1:10-1:5 elution) to give (2R,3S)-2-{2-[Bis-(4-methoxyphenyl)phenyl-methoxymethyl]-(2R,3R)-3-(4-hydroxy-3-methoxyphenyl)-2,3-dihydrobenzo[b][1,4]dioxan-6-yl}chroman-3,5,7-triol (6) (1.15 g). The yield was 46.6%

Step B: A mixture of compound 120 (1.13 g, 1.47 mmol), acetic anhydride (2.99 g, 29.3 mmol) and pyridine (5 mL) was stirred at room temperature overnight. Ethyl acetate (20 mL×2) and water (20 mL) were added for extraction, and the combined organic phase was washed with saturated brine (20 mL) and dried over anhydrous sodium sulfate. The solvent was evaporated under reduced pressure, and the product was purified by column chromatography (200-300 mesh silica gel, ethyl acetate:dichloromethane:petroleum ether=1:10:10-1:5:5 elution) to give 3,5-diacetoxy-(2R,3S)-2-{(2R,3R)-3-(4-acetoxy-3-methoxyphenyl)-2-[bis-(4-methoxyphenyl)phenyl-methoxymethyl]-2,3-dihydrobenzo[b][1,4]dioxan-6-yl}chroman-7-yl acetate (121) (1.38 g). The compound was used directly in the next step without purification.

Step C: Compound 121 (1.38 g, 1.47 mmol) was dissolved in dichloromethane (10 mL), a solution of 10% formic acid in dichloromethane (10 mL) was added, the reaction system was stirred at room temperature for 1 hour. Water (20 mL) was added for extraction. The aqueous phase was washed with dichloromethane (10 mL), and the combined organic phase was washed with saturated sodium bicarbonate and brine, and dried over anhydrous sodium sulfate. The solvent was evaporated under reduced pressure, and the product was purified by column chromatography (200-300 mesh silica gel, ethyl acetate:dichloromethane=1:10-1:5 elution) to give 3,5-diacetoxy-(2R,3S)-2-{(2R,3R)-3-(4-acetoxy-3-methoxyphenyl)-2-hydroxymethyl]-2,3-dihydrobenzo[b][1,4]dioxan-6-yl}chroman-7-yl acetate (122) (855 mg). The yield was 91.4%.

Step D: Compound 122 (850 mg, 1.34 mmol) and Et$_3$N (176 mg, 1.74 mmol) were dissolved in dichloromethane (10 mL) and a solution of methylsulfonyl chloride (184 mg, 1.60 mmol) in methylene chloride (2 mL) was added dropwise under an ice bath and stirred at room temperature for 1 hour. Water (20 mL) was added for extraction. The aqueous phase was washed with dichloromethane (10 mL), the combined organic phase was washed with saturated brine and dried over anhydrous sodium sulfate. The solvent was evaporated under reduced pressure and the product was purified by column chromatography (200-300 mesh silica gel, ethyl acetate:dichloromethane=1:10-1:6 elution) to give 3,5-diacetoxy-(2R,3S)-2-{(2R,3R)-3-(4-acetoxy-3-methoxyphenyl)-2-methanesulfonyloxymethyl-2,3-dihydrobenzo[b][1,4]dioxan-6-yl}chroman-7-yl acetate (123) (905 mg). The yield was 94.9%.

Step E: A mixture of compound 123 (300 mg, 420 μmol), NaN$_3$ (81.9 mg, 1.26 mmol) and DMF (5 mL) was stirred at 70° C. overnight. Ethyl acetate (15 mL×2) and water (15 mL) were added for extraction, the combined organic phase was washed with saturated brine and dried over anhydrous sodium sulfate. The solvent was evaporated under reduced pressure and the product was purified by column chromatography (200-300 mesh silica gel, ethyl acetate:dichloromethane=1:10-1:5 elution) to give 3,5-diacetoxy-(2R,3S)-2-{(2R,3R)-3-(4-acetoxy-3-methoxyphenyl)-2-azidomethyl-2,3-dihydrobenzo[b][1,4]dioxan-6-yl}chroman-7-yl acetate (124) (125 mg). The yield was 45.0%.

Step F: A mixture of compound 124 (120 mg, 181 μmol), concentrated hydrochloric acid (1 mL) and EtOH (4 mL) was stirred at 50° C. for 0.5 hour. Ethyl acetate (10 mL×2) and water (10 mL) were added for extraction. The combined organic phase was washed with saturated sodium bicarbonate and brine and dried over anhydrous sodium sulfate. The solvent was evaporated under reduced pressure and the product was purified by column chromatography (200-300 mesh silica gel, ethyl acetate:dichloromethane=1:5=1:3 elution) to give (2R,3S)-2-{2-Azidomethyl-(2R,3R)-3-(4-acetoxy-3-methoxyphenyl)-2,3-dihydrobenzo[b][1,4]dioxan-6-yl}chroman-3,5,7-triol (125) (55.0 mg). The yield was 61.5%.

Step G: A mixture of compound 125 (50 mg, 101 μmol), Pd/C (5 mg) and methanol (3 mL) was stirred overnight at room temperature. After filtering through a pad of celite, the filtrate was evaporated under reduced pressure to remove the solvent and the product was purified by column chromatography (200-300 mesh silica gel, ethyl acetate:dichloromethane=1:3-2:1 elution) to give (2R,3S)-2-{2-aminomethyl-(2R,3R)-3-(4-hydroxy-3-methoxyphenyl)-2,3-dihydrobenzo[b][1,4]dioxan-6-yl}chroman-3,5,7-triol (126). $^1$H NMR (DMSO-d$_6$, 400 MHz) δ 9.17 (s, 1H), 9.07 (s, 1H), 8.93 (s, 1H), 7.01 (s, 1H), 6.94-6.80 (m, 2H), 5.90 (d, J=2.0 Hz, 1H), 5.70 (d, J=2.0 Hz, 1H), 4.94 (br, 1H), 4.87 (d, J=8.0 Hz, 1H), 4.58 (d, J=5.6 Hz, 1H), 4.18-4.15 (m, 1H), 3.89-3.86 (m, 1H), 3.79 (s, 3H), 3.76-3.74 (m, 1H), 2.74 (br, 2H), 2.69-2.65 (m, 1H), 2.41-2.35 (m, 1H). MS (ESI, m/z): 466.2 [M−H]$^-$.

Example 22: Synthesis of 2-{8-hydroxy-3-(4-hydroxy-3-methoxyphenyl)-2-hydroxymethyl-2,3-dihydrobenzo[b][1,4]dioxan-6-yl}chroman-3,4,6,7-tetraol (136)

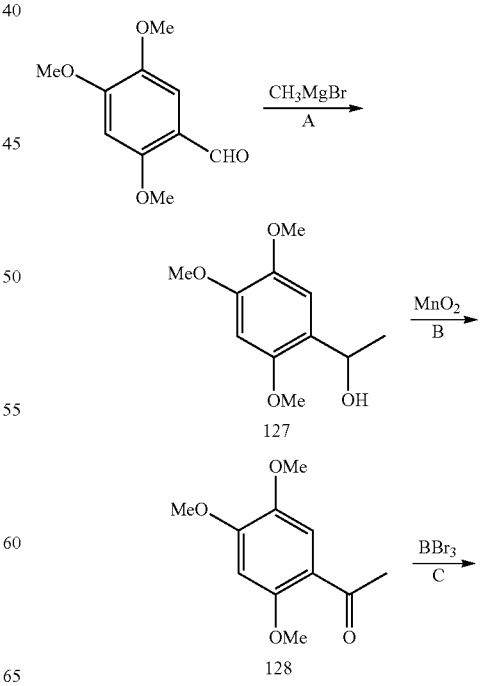

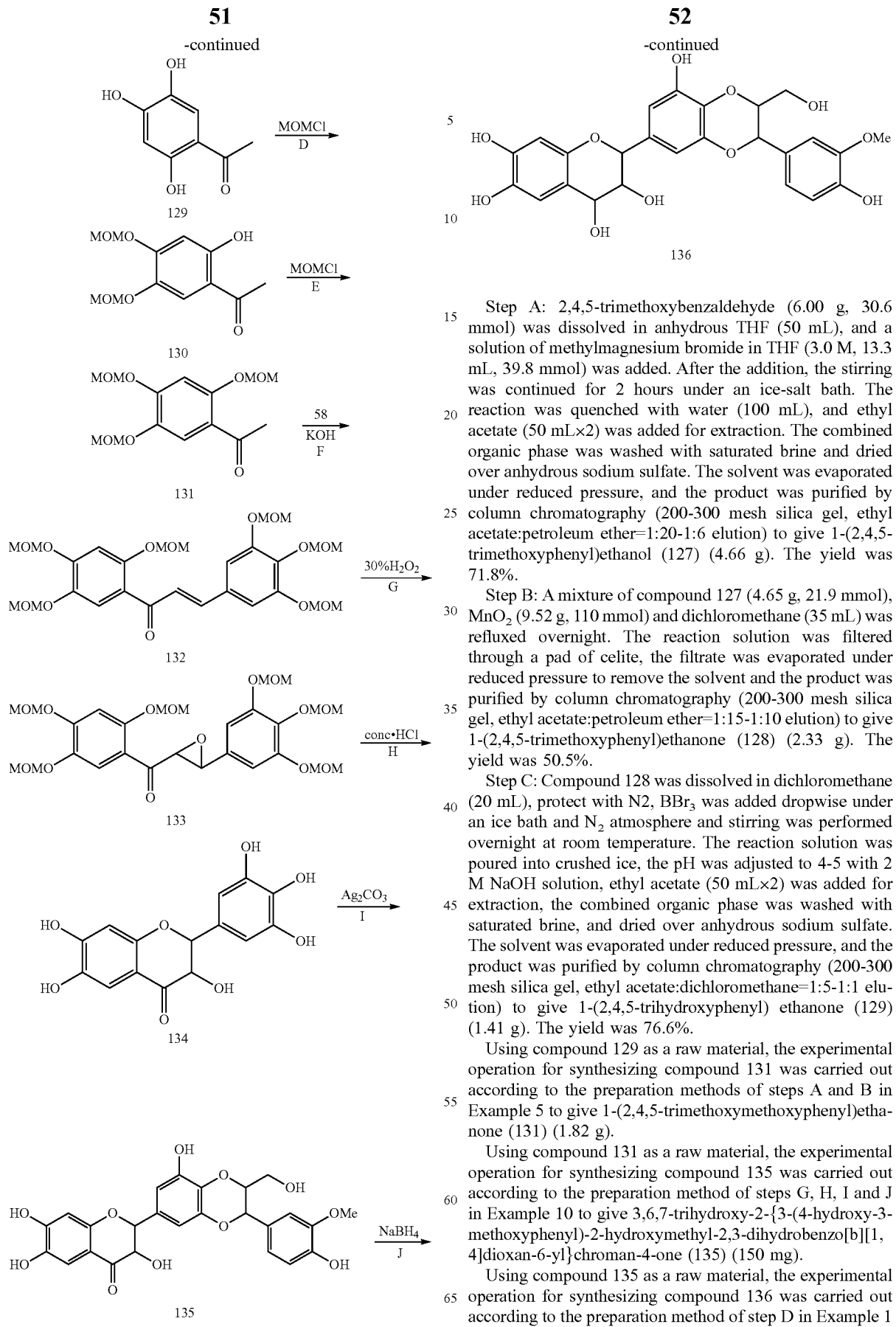

Step A: 2,4,5-trimethoxybenzaldehyde (6.00 g, 30.6 mmol) was dissolved in anhydrous THF (50 mL), and a solution of methylmagnesium bromide in THF (3.0 M, 13.3 mL, 39.8 mmol) was added. After the addition, the stirring was continued for 2 hours under an ice-salt bath. The reaction was quenched with water (100 mL), and ethyl acetate (50 mL×2) was added for extraction. The combined organic phase was washed with saturated brine and dried over anhydrous sodium sulfate. The solvent was evaporated under reduced pressure, and the product was purified by column chromatography (200-300 mesh silica gel, ethyl acetate:petroleum ether=1:20-1:6 elution) to give 1-(2,4,5-trimethoxyphenyl)ethanol (127) (4.66 g). The yield was 71.8%.

Step B: A mixture of compound 127 (4.65 g, 21.9 mmol), $MnO_2$ (9.52 g, 110 mmol) and dichloromethane (35 mL) was refluxed overnight. The reaction solution was filtered through a pad of celite, the filtrate was evaporated under reduced pressure to remove the solvent and the product was purified by column chromatography (200-300 mesh silica gel, ethyl acetate:petroleum ether=1:15-1:10 elution) to give 1-(2,4,5-trimethoxyphenyl)ethanone (128) (2.33 g). The yield was 50.5%.

Step C: Compound 128 was dissolved in dichloromethane (20 mL), protect with N2, $BBr_3$ was added dropwise under an ice bath and $N_2$ atmosphere and stirring was performed overnight at room temperature. The reaction solution was poured into crushed ice, the pH was adjusted to 4-5 with 2 M NaOH solution, ethyl acetate (50 mL×2) was added for extraction, the combined organic phase was washed with saturated brine, and dried over anhydrous sodium sulfate. The solvent was evaporated under reduced pressure, and the product was purified by column chromatography (200-300 mesh silica gel, ethyl acetate:dichloromethane=1:5-1:1 elution) to give 1-(2,4,5-trihydroxyphenyl) ethanone (129) (1.41 g). The yield was 76.6%.

Using compound 129 as a raw material, the experimental operation for synthesizing compound 131 was carried out according to the preparation methods of steps A and B in Example 5 to give 1-(2,4,5-trimethoxymethoxyphenyl)ethanone (131) (1.82 g).

Using compound 131 as a raw material, the experimental operation for synthesizing compound 135 was carried out according to the preparation method of steps G, H, I and J in Example 10 to give 3,6,7-trihydroxy-2-{3-(4-hydroxy-3-methoxyphenyl)-2-hydroxymethyl-2,3-dihydrobenzo[b][1,4]dioxan-6-yl}chroman-4-one (135) (150 mg).

Using compound 135 as a raw material, the experimental operation for synthesizing compound 136 was carried out according to the preparation method of step D in Example 1 to give 2-{8-hydroxy-3-(4-hydroxy-3-methoxyphenyl)-2- hydroxymethyl-2,3-dihydrobenzo[b][1,4]dioxan-6-yl}chroman-3,4,6,7-tetraol (136). MS (ESI, m/z): 499.1 [M–H]⁻.

Example 23: Synthesis of 2-{8-hydroxy-3-(4-hydroxy-3-methoxyphenyl)-2-hydroxymethyl-2,3-dihydrobenzo[b][1,4]dioxan-6-yl}chroman-3,6,7-triol (137)

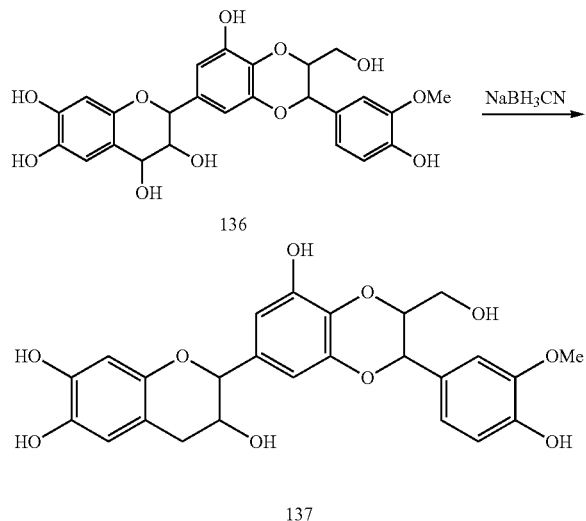

Using compound 136 as a raw material, the experimental operation for synthesizing compound 137 was performed according to the preparation method in Example 3 to give 2-{8-hydroxy-3-(4-hydroxy-3-methoxyphenyl)-2-hydroxymethyl-2,3-dihydrobenzo[b][1,4]dioxan-6-yl}chroman-3,6,7-triol (137). ¹H NMR (DMSO-d₆, 400 MHz) δ 9.12 (s, 1H), 9.05 (s, 1H), 8.71 (s, 1H), 8.26 (s, 1H), 7.01 (s, 1H), 7.00-6.79 (m, 2H), 6.46-6.38 (t, 2H), 6.24 (s, 1H), 4.93 (d, J=5.6 Hz, 1H), 4.92-4.83 (m, 2H), 4.50 (d, J=7.2 Hz, 1H), 4.12-4.09 (m, 1H), 3.89-3.88 (m, 1H), 3.87 (s, 3H), 3.50-3.48 (m, 1H), 3.44-3.43 (m, 1H), 2.75-2.71 (m, 1H), 2.62-2.58 (m, 1H). MS (ESI, m/z): 483.2 [M–H]⁻.

Example 24: Synthesis of {(2R,3R)-3-(4-hydroxy-3-methoxyphenyl)-6-(3,5,7-trihydroxychroman-2-yl)-2,3-dihydrobenzo[b][1,4]dioxan-2-yl}acetic acid (140)

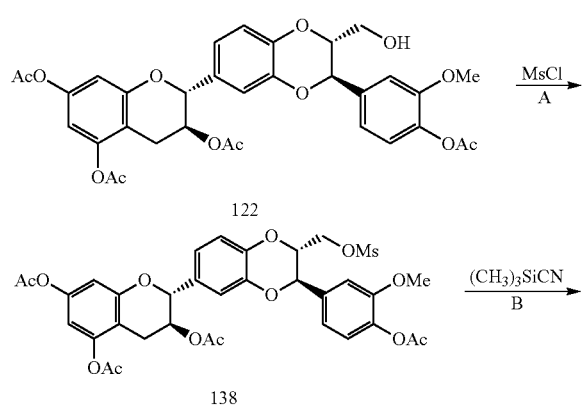

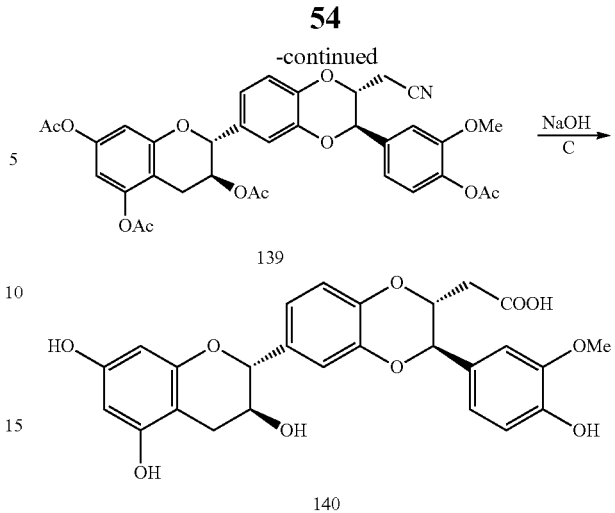

Step A: A mixture of compound 122 (130 mg, 204 μmol), Et₃N (31.0 mg, 306 μmol), MsCl (30.4 mg, 265 μmol) and dichloromethane (3 mL) was stirred at room temperature for 1.5 hours. Dichloromethane (10 mL×2) and water were added for extraction, and the combined organic phase was washed with saturated brine and dried over anhydrous sodium sulfate. The solvent was evaporated under reduced pressure to give 3,7-diacetoxy-(2R,3S)-2-{(2R,3R)-3-(4-acetoxy-3-methoxyphenyl)-2-methanesulfonyloxymethyl-2,3-dihydrobenzo[b][1,4]dioxan-6-yl}chroman-5-yl acetate (138) (143 mg), which was used directly in the next step without purification.

Step B: A mixture of compound 138 (140 mg, 196 μmol), TMSCN (311 mg, 314 mmol), TBAF (666 mg, 255 mmol), THF (3 mL) and acetonitrile (3 mL) was stirred at 80° C. overnight. After cooling to room temperature, ethyl acetate (10 mL×2) and water (10 mL) were added for extraction, and the combined organic phase was washed with saturated brine, and dried over anhydrous sodium sulfate. The solvent was evaporated under reduced pressure, and the product was purified by column chromatography (200-300 mesh silica gel, ethyl acetate:dichloromethane:petroleum ether=1:1:15-1:1:5 elution) to give 3,7-diacetoxy-(2R,3S)-2-((2R,3R)-3-(4-acetoxy-3-methoxyphenyl)-2-cyanomethyl-2,3-dihydrobenzo[b][1,4]dioxan-6-yl}chroman-5-yl acetate (139) (120 mg).

Step C: A mixture of compound 139 (110 mg, 170 μmol) and 4M NaOH aqueous solution (10 mL) was stirred at 80° C. overnight. The pH was adjusted to 3-4 with 2 M hydrochloric acid, ethyl acetate (10 mL×2) and water (10 mL) were added for extraction. The combined organic phase was washed with saturated brine and dried over anhydrous sodium sulfate. The solvent was evaporated under reduced pressure and the product was purified by column chromatography (200-300 mesh silica gel, eluted with ethyl acetate) to give {(2R,3R)-3-(4-hydroxy-3-methoxyphenyl)-6-(3,5,7-trihydroxychroman-2-yl)-2,3-dihydrobenzo[b][1,4]dioxan-2-yl}acetic acid (140). MS (ESI, m/z): 495.1 [M–H]⁻.

Example 25: Determination of Compound Solubility

1. Test Materials

The test compounds were 7, 67 and 85, respectively; the control compound was silymarin, purchased from Shanghai Dibai Biotechnology Co., Ltd., with the batch number HH06. Both the test compounds and the control compound were prepared into 10 mM stock solutions using DMSO. Phosphate buffered saline (PBS), with pH of 4.0 and 7.4, was used to test the solubility of the test compounds.

2. Test Method

Treatment of test compound and control compound: 30 μL of test compound or control compound stock solution (10 mM) per well was added in a specially made solubility sample plate, and then 970 μL of PBS with different pH was added to each well (pH was 4.0 and 7.4, respectively). Repeated wells were set in the test. A stir bar was added to each well that was covered with a polytetrafluoroethylene or silica gel plug. Stirring was performed at 25° C. at 1100 rpm for 2 hours. 10 μL of sample was taken from each well, and then 990 μL of water and acetonitrile mixture (including internal standard substance) was added to mix well, followed by filtering with a filter plate.

Standard treatment: 10 mM stock solution was diluted with DMSO to 300 μM, then 10 μL of compound diluent was taken, and 990 μL of water and acetonitrile mixture (including internal standard substance) was added to mix well and formulated into a standard solution with the final concentration 3 μM.

The solubility sample plate was placed in the autosampler and the LC-MS/MS method was used for analysis. The concentration of the test compound was calculated by the response value of the test compound and standard, and the concentration of the standard.

3. Test Results

As shown in Table 1, in the PBS buffer solution with pH 4.0 and 7.4, the solubility of the test compounds 7, 67 and 85 in the PBS buffer solution was significantly higher than that of silymarin.

TABLE 1

Solubility of compounds in buffer solutions with different pH

| Compound | Solubility (MM) | |
|---|---|---|
| | pH = 4.0 | pH = 7.4 |
| 7 | 209.07 | 213.74 |
| 67 | 148.15 | 146.17 |
| 85 | 159.84 | 150.47 |
| silymarin | 1.08 | 15.00 |

The poor solubility of silymarin has caused the problem of low bioavailability. The solubility of compounds 7, 67 and 85 has been significantly improved, which may increase in vivo absorption of these compounds and increase the bioavailability of the compounds, thereby improving the pharmacological activity of the compounds.

Example 26: Test of Fat Reduction or Elimination Effect of Compounds on Zebrafish Non-Alcoholic Fatty Liver 1. Test Materials (1). Test Compounds 40 mM stock solution of test compounds 4, 5, 6, 7, 46, 67, 78, 85, 92 and 101 were prepared with DMSO, and stored in a refrigerator at −20° C. The positive control compound S-adenosylmethionine (SAM) was purchased from Aladdin Reagent (Shanghai) Co., Ltd., with the batch number F1523051, which was prepared into a 50 mM stock solution with DMSO. The control compound silymarin was purchased from Shanghai Dibai Biotechnology Co., Ltd., with the batch number EE09, which was prepared into a 40 mM stock solution with DMSO. Thioacetamide was purchased from Sigma-Aldrich, with the batch number BCBV3031, which was prepared into a 1 M stock solution with DMSO. Oil Red O was purchased from Sigma-Aldrich, with the batch number SLBP5248V. 4% paraformaldehyde was purchased from Dingguo Biotechnology Co., Ltd., with the batch number 773001800. Propylene glycol was purchased from Sinopharm Chemical Reagent Co., Ltd., with the batch number 20170615.

(2). Experimental Animals

The melanin allele mutant translucent Albino line zebrafish was reproduced in natural paired mating. The fish age was 3 days after fertilization, with 30 fish per experimental group.

The above zebrafish were raised in fish farming water at 28° C. (water quality: 200 mg instant sea salt was added to 1 L of reverse osmosis water, conductivity was 480-510 μS/cm; pH was 6.9-7.2; hardness was 53.7-71.6 mg/L CaCOs), the experimental animal use license number was: SYXK (Zhejiang) 2012-0171. Feeding management met the requirements of international AAALAC certification.

2. Test Method

1. Establishment of Non-Alcoholic Fatty Liver Model in Zebrafish

Three days after fertilization, the normal melanin allele mutant translucent Albino strain of zebrafish was randomly selected and placed in a six well plate with 30 fish per well (i.e. each experimental group), and then thioacetamide with the final concentration of 7 mM was used to treat zebrafish for 72 hours to establish the non-alcoholic fatty liver model.

2. Evaluation of the Efficacy of the Test Compounds

The zebrafish were transferred to a six-well plate, with 30 fish per well (i.e., each experimental group) randomly. Non-alcoholic fatty liver model in zebrafish were induced by thioacetamide. 40 mM test compounds 4, 5, 6, 7, 46, 67, 78, 85, 92 and 101 were quantitatively transferred to a six-well plate, and diluted with water to the corresponding concentration. Test compounds 4, 5, 6 and 7 were formulated into two dose groups with final concentration of 100 μM and 200 μM, respectively; test compound 46 was formulated into a dose group with final concentration of 200 μM; test compounds 67, 78, 85, 92 and 101 were formulated into dose groups with a final concentration of 100 μM; 50 mM positive control SAM was formulated with water to a dose group with final concentration of 50 μM, and a 40 mM positive control silymarin was formulated with water to two concentration dose groups with final concentration of 100 μM and 200 μM. A normal control group (zebrafish treated with fish farming water) and a model control group were set at the same time, and the total volume of each well was 3 mL. Except for the normal control group, the other experimental groups were treated with thioacetamide for 72 hours and stained with Oil Red O. After staining, 10 zebrafish were randomly selected from each experimental group and photographed under a dissecting microscope, NIS-Elements D 3.10 advanced image processing software was used to perform image analysis and collect data, the total optical density (S) of zebrafish liver fat was statistically analyzed, and for the inhibitory effect of each experimental group on liver steatosis of zebrafishwas evaluated by the following formula, the results of statistical analysis were expressed as mean±SE:

Inhibition rate of liver steatosis (%)=[$S$(model control group)−$S$(test compound group)]/[$S$(model control group)−$S$(normal control group)]×100%

Statistical analysis was performed using analysis of variance and Dunnett's T-test, and p<0.05 indicated a significant difference. The inhibition rate of liver steatosis indicated the degree of reduction of liver fat by the test compound on the modeled zebrafish. The larger the value, the more obvious the reduction or elimination effect of the test compound on liver fat.

3. Test Results

As shown in Table 2 and Table 3, the average value of the total optical density of zebrafish liver fat in the model control group was 22816, which was significantly greater than the average value of the normal control group (17734). The statistical analysis between the model control group and the normal control group showed that, p<0.001, indicated that the model was established successfully. Compared with the model control group, the inhibiton rate of liver steatosis by positive control SAM (50 μM) was 89% (p<0.001); The inhibition rates of silybin were 49% and 69% at concentrations of 100 μM and 200 μM, and the p values were <0.05 and <0.01, respectively. It showed that the positive control SAM and silymarin had protective effects on non-alcoholic fatty liver of zebrafish.

The test results were shown in Table 2 and FIG. 1. The inhibition rates of compounds 4, 5, 6 and 7 on liver steatosis of zebrafish were 99%, 86%, 92% and 93% at the concentration of 200 μM, respectively. The lipid droplets (stained with oil red O) of the zebrafish liver in each test compound group were significantly reduced, while at the same concentration, the inhibition rate of positive control silymarin was only 69%. The test results showed that at a concentration of 200 μM, the test compounds 4, 5, 6, 7 and 46 had a significant therapeutic effect on zebrafish non-alcoholic fatty liver, and had a significantly better fat reduction or elimination effect on non-alcoholic fatty liver of zebrafish than that of silymarin.

TABLE 2

The inhibitory effects of test compounds and silymarin on z liver steatosis of ebrafish at 200 μM (the concentration of SAM was 50 μM, n = 10)

| Group | The total optical density of liver fat (Pixels, mean ± SE) | Inhibition rate of liver steatosis % |
|---|---|---|
| normal group | 17734 ± 532 | — |
| model control group | 22816 ± 910 | — |
| 4 | 17802 ± 487 | 99*** |
| 5 | 18452 ± 795 | 86** |
| 6 | 18157 ± 572 | 92*** |
| 7 | 18090 ± 437 | 93*** |
| 46 | 19767 ± 814 | 60* |
| S-adenosylmethionine | 18301 ± 783*** | 89*** |
| silymarin | 19300 ± 502** | 69** |

Compared with the model control group, *p < 0.05, p < 0.01, *p < 0.001

The inhibition rates of test compounds 4, 5, 7, 67, 85, 92 and 101 at the concentration of 100 μM on the liver steatosis were 83%, 84%, 98%, >100%, >100%, 98% and 93%, respectively, the lipid droplets (stained with oil red O) at the zebrafish liver in each test compound group were significantly reduced, while the inhibition rate of positive control silymarin was only 49%, indicating that these compounds has significantly better fat reduction or elimination effects on non-alcoholic fatty liver of zebrafish than that of silymarin. At a concentration of 100 μM, the test compounds 4, 5, 6, 7, 67, 78, 85, 92 and 101 had significant therapeutic effects on non-alcoholic fatty liver of zebrafish. The test results were shown in Table 3 and FIG. 2.

TABLE 3

The inhibitory effects of test compounds and silymarin on liver steatosis of zebrafish at 100 μM (the concentration of SAM was 50 μM, n = 10)

| Group | The total optical density of liver fat (Pixels, mean ± SE) | Inhibition rate of liver steatosis % |
|---|---|---|
| normal group | 17734 ± 532 | — |
| model control group | 22816 ± 910 | — |
| 4 | 18598 ± 608 | 83** |
| 5 | 18496 ± 862 | 85** |
| 6 | 19868 ± 556 | 58* |
| 7 | 17835 ± 351 | 98*** |
| 67 | 16667 ± 469 | >100*** |
| 78 | 19665 ± 1330 | 62** |
| 85 | 17378 ± 710 | >100*** |
| 92 | 17836 ± 639 | 98*** |
| 101 | 18090 ± 837 | 93*** |
| S-adenosylmethionine | 18301 ± 783*** | 89*** |
| silymarin | 20326 ± 924* | 49* |

Compared with the model control group, *p < 0.05, p < 0.01, *p < 0.001

The test results showed that compounds 4, 5, 7, 67, 85, 92 and 101 involved in this patent had significantly higher inhibition rates on liver steatosis than that of silymarin, showing extremely excellent inhibitory effects on non-alcoholic fatty liver of zebrafish.

Example 27: Evaluation of the Efficacy of the Compounds on Non-Alcoholic Steatohepatitis (NASH) Mice 1. Test Materials (1). Preparation of Test Compound and Solution The test compounds were 4 and 7, respectively; the positive control silymarin was purchased from Shanghai Dibai Biotechnology Co., Ltd., with the batch number HH06.

Low-dose group (35 mg/kg) solution preparation: the quantitative test compound was precisely weighed and a certain amount of normal saline was added to prepare the oral suspension solution with the concentration of 3.5 mg/mL. The administration volume was 10 mL/kg.

High-dose group (70 mg/kg) solution preparation: the quantitative test compound was precisely weighed and a certain amount of normal saline was added to prepare the oral suspension solution with the concentration of 7.0 mg/mL. The administration volume was 10 mL/kg.

(2). Feed for Modeling

High-fat feed: basic feed ingredients were corn, flour, imported fish meal, soybean meal, secondary meal, yeast meal, soybean oil, etc. The high-fat feed was prepared from 73.6% basic feed with 10% lard, 10% egg yolk powder, 5% sucrose, 1.2% cholesterol and 0.2% pig bile salt.

(3). Experimental Animals

Source, species, strain: $C_{57}BL/6$ mice, provided by Beijing Vital River Laboratory Animal Technology Co., Ltd. Nanjing Branch (experimental animal production license: SCXK (Su) 2016-0003); experimental animal use license: SYXK (Jun) 2012-0049; age: 6-8 weeks at the beginning of dosing; weight: 18-22 g; gender: half male and half female.

2. Test Method

After 3 days of adaptive feeding with normal feed, the mice were randomly assigned according to body weight: 8 mice were fed with normal feed and set as normal control (NC); the rest of mice were fed with high-fat feed until the end of the experiment. The mice were weighed and recorded every 3 days. After feeding with high-fat diet for 56 days (8 weeks), blood samples were collected from the orbital vein of mice to detect the blood biochemical indexes to identify whether the modelling was successful.

After successful modeling, the mice in the high-fat feed group were randomly divided into 6 groups with 8 animals in each group, including model group, compound 4 low dose group, compound 4 high dose group, compound 7 low dose group, compound 7 high dose group and silymarin high-dose group. The mice in each group were administered intragastrically according to the animal's body weight every day for 28 consecutive days (4 weeks). At the same time, during the administration period, the mice in each administration group and model group continued to be fed with high-fat feed until the end of the experiment. The normal control group was administered the corresponding volume of normal saline.

On the last day of the experiment, the mice in each group were fasted for 8 hours, blood was taken from the orbit and the serum was separated and then stored at −20° C. After blood collection, the mice were sacrificed and the liver was quickly separated, weighed and stored in a refrigerator at −80° C. Serum samples and liver tissue samples were subjected to determinations of serum triglyceride (TG), serum total cholesterol (TC), serum high-density lipoprotein (HDL-C), serum low-density lipoprotein (LDL-C), serum alanine aminotransferase (ALT), serum aspartate aminotransferase (AST), serum tumor necrosis factor alpha (TNFα), liver triglycerides (TG), liver total cholesterol (TC), liver malondialdehyde (MDA), liver superoxide dismutase (SOD); in addition, some livers of mice in the blank control group, model group, compound 7 low-dose group and silymarin high-dose group were fixed in neutral formaldehyde fixed solution and then HE staining was performed to analyzed the pathological changes of liver tissue.

3. Test Results

As shown in Table 4, Table 5, Table 6 and Table 7, the liver coefficient of $C_{57}BL/6$ mice fed with high-fat feed after three months was significantly higher than that of the blank control group (p<0.01). The serum indexes (TC, TG, LDL-C, ALT, AST and TNFα) and liver tissue indexes (TC, TG, MDA and SOD) of the model group were significantly different from those of the blank control group (p<0.01). Compared with the model group, continuous intragasric administration of the positive compound silymarin at 70 mg/kg for 1 month can significantly reduce the levels of ALT, AST, LDL-C and TNFα in the blood, and significantly reduce the TC, TG and MDA levels in the liver tissue, increase SOD activity (p<0.01), and liver coefficient decreased significantly (p<0.05), indicating that the positive compound silymarin had a certain therapeutic effect on NASH mice.

Compared with the model group, compounds 4 and 7 could significantly reduce the ALT and AST levels in the blood, improve the levels of TC, TG and MDA in liver tissue (P<0.01), and significantly reduce the expression of inflammatory factor TNF a. Compound 7 can also significantly reduce the levels of TG and LDL-C in the blood, and increase the activity of SOD in low dose group (p<0.05).

TABLE 4

Effects of compounds on liver weight and liver coefficient in NASH mice ($\overline{X}$ ± SD)

| Group | Dosage (mg/kg/day) | Liver weight (g) | Liver coefficient |
|---|---|---|---|
| normal group | — | 1.12 ± 0.07** | 4.20 ± 0.30** |
| model group | — | 1.84 ± 0.09 | 5.57 ± 0.84 |
| compound 4 low dose group | 35 | 1.39 ± 0.03** | 4.43 ± 0.31* |
| compound 4 high dose group | 70 | 1.43 ± 0.03** | 4.54 ± 0.33* |
| compound 7 low dose group | 35 | 1.40 ± 0.05** | 4.53 ± 0.38* |
| compound 7 high dose group | 70 | 1.41 ± 0.02** | 4.51 ± 0.28* |
| silymarin | 70 | 1.40 ± 0.06** | 4.58 ± 0.40* |

Note:
Compared with the model group, *p < 0.05, **p < 0.01;
liver coefficient (%) = liver weight/body weight * 100%

TABLE 5

Effects of compounds on TC, TG, HDL-C and LDL-C in NASH mice ($\overline{X}$+SD)

| Group | Dosage (mg/kg/day) | TC (mmol/L) | TG (mmol/L) | HDL-C (mmol/L) | LDL-C (mmol/L) |
|---|---|---|---|---|---|
| normal group | — | 2.50 ± 0.12* | 1.09 ± 0.20** | 0.99 ± 0.52 | 0.61 ± 0.33** |
| model group | — | 3.66 ± 1.23 | 1.69 ± 0.40 | 0.68 ± 0.21 | 2.86 ± 0.51 |
| compound 4 low dose group | 35 | 2.59 ± 0.32 | 1.18 ± 0.02* | 0.95 ± 0.33 | 2.55 ± 0.50 |
| compound 4 high dose group | 70 | 2.58 ± 0.30 | 1.24 ± 0.16* | 0.97 ± 0.37 | 2.13 ± 0.54* |
| compound 7 low dose group | 35 | 2.59 ± 0.38 | 1.13 ± 0.06* | 0.83 ± 0.35 | 1.95 ± 0.50** |
| compound 7 high dose group | 70 | 2.63 ± 0.81 | 1.11 ± 0.07** | 0.89 ± 0.46 | 1.85 ± 0.37** |
| silymarin | 70 | 2.75 ± 0.84 | 1.16 ± 0.22* | 0.85 ± 0.48 | 1.91 ± 0.35** |

Note:
Compared with the model group, *p < 0.05, **p < 0.01.

TABLE 6

Effects of compounds on ALT, AST and TNF-α in NASH mice ($\overline{X} \pm SD$)

| Group | Dosage (mg/kg/day) | ALT (U/L) | AST (U/L) | TNF-α (ng/L) |
|---|---|---|---|---|
| normal group | — | 52.12 ± 30.39** | 46.84 ± 5.02** | 359.38 ± 9.92** |
| model group | — | 220.24 ± 59.28 | 288.50 ± 86.43 | 471.04 ± 13.09 |
| compound 4 low dose group | 35 | 89.08 ± 18.93** | 140.13 ± 13.93** | 414.20 ± 13.46* |
| compound 4 high dose group | 70 | 98.29 ± 75.07** | 120.04 ± 12.55** | 415.80 ± 13.54** |
| compound 7 low dose group | 35 | 63.03 ± 30.59** | 115.16 ± 13.42** | 414.26 ± 11.57** |
| compound 7 high dose group | 70 | 75.75 ± 27.48** | 123.61 ± 5.41** | 425.80 ± 9.77** |
| silymarin | 70 | 103.33 ± 26.43** | 127.39 ± 7.75** | 423.36 ± 8.73** |

Note:
Compared with the model group, *p < 0.05, **p < 0.01.

TABLE 7

Effects of compounds on biochemical indexes of liver in NASH mice ($\overline{X} \pm SD$)

| Group | Dosage (mg/kg/day) | TC (mmol/L) | TG (mmol/L) | MDA (nmol/mg) | SOD (U/mg) |
|---|---|---|---|---|---|
| normal group | — | 1.20 ± 0.13** | 1.04 ± 0.03** | 2.27 ± 0.39** | 21.83 ± 2.01** |
| model group | — | 2.54 ± 0.19 | 1.52 ± 0.07 | 3.60 ± 0.52 | 14.72 ± 4.53 |
| compound 4 low dose group | 35 | 1.51 ± 0.06** | 1.21 ± 0.05** | 2.91 ± 0.42** | 18.08 ± 3.90 |
| compound 4 high dose group | 70 | 1.51 ± 0.11** | 1.18 ± 0.06** | 2.80 ± 0.21** | 17.42 ± 4.16 |
| compound 7 low dose group | 35 | 1.53 ± 0.06** | 1.22 ± 0.06** | 2.84 ± 0.24** | 18.54 ± 4.41 |
| compound 7 high dose group | 70 | 1.54 ± 0.09** | 1.25 ± 0.06** | 2.79 ± 0.21** | 19.44 ± 3.11* |
| silymarin | 70 | 1.55 ± 0.08** | 1.24 ± 0.05** | 2.69 ± 0.22** | 24.89 ± 6.09** |

Note:
Compared with the mode group, *p < 0.05, **p < 0.01.

The histopathological results of model group (FIG. 3) showed that the liver cells of the model group had obvious fatty degeneration and necrosis, and had inflammatory cell foci, which indicated that the NASH model was successfully established. However, there were no lipid droplet vacuoles caused by steatosis in the mouse liver cells of the compound 7 low-dose group, and there were very few inflammatory cells in the liver tissues of a few mice. Therefore, it was shown that compound 7 can effectively improve the lipidation degree of liver tissue of NASH mice and reduce inflammation.

The test results showed that the compounds 4 and 7 involved in the patent had significant therapeutic effects on non-alcoholic steatohepatitis in mice.

Example 28: Acute Toxicity Test of Single Administration of Compound in Mice 1. Test Materials
(1). Preparation of Test Compound and Solution
The test compound was compound 7; the positive control silymarin was purchased from Shanghai Dibai Biotechnology Co., Ltd., with the batch number HH06. Immediately before use, the suspension was prepared with normal saline and ultrasound to prepare a suspension with a corresponding concentration.

Low-dose group (1.5 g/kg) solution preparation: the quantitative test compound 7 or positive control compound was precisely weighed, and a certain amount of normal saline was added to prepare the oral suspension solution with the concentration of 75 mg/mL. The administration volume was 20 mL/kg.

High-dose group (3.0 g/kg) solution preparation: the quantitative test compound 7 or positive control compound was precisely weighed, and a certain amount of normal saline was added to prepare the oral suspension solution with the concentration of 150 mg/mL. The administration volume was 20 mL/kg.

(2). Experimental Animals and Breeding Conditions
ICR mice, SPF grade, weight: 16-18 g, 6-8 weeks old. Provided by Nantong University, laboratory animal production license number: SCXK (Su) 2014-0001; laboratory animal use license: SYXK (Su) 2017-0007.

2. Test Method
16 ICR mice were randomly divided into compound 7 low-dose group, compound 7 high-dose group, silymarin low-dose group and silymarin high-dose group, with 4 mice in each group, half male and half female. After fasting for 6 hours, the compound 7 suspension or silymarin suspension was administered at 20 mL/kg by gavage.

3. Test Results
The dosage and mortality of mice in each group were shown in Table 8. There was no immediate toxicity after administration and no delayed toxicity was found in the observation period from 24 hours to 14 days. The animals were in good condition and all mice survived. The maximum tolerated dose of compound 7 and silymarin in the acute toxicity test in mice was 3 g/kg.

TABLE 8

Dosage and mortality of ICR mice

| Group | Animal number | Dosage (g/kg) | Concentration (mg/mL) | Administration volume (mL/kg) | Mortality |
|---|---|---|---|---|---|
| compound 7 low dose group | 4 | 1.5 | 75 | 20 | 0/4 |
| compound 7 high dose group | 4 | 3.0 | 150 | 20 | 0/4 |
| silymarin low dose group | 4 | 1.5 | 75 | 20 | 0/4 |
| silymarin high dose group | 4 | 3.0 | 150 | 20 | 0/4 |

What is claimed is:

1. A compound represented by following formula an optical isomer or pharmaceutically acceptable salt thereof,

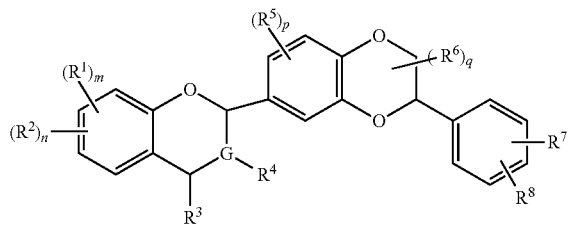

wherein,
i) p is 1:
 $R^1$ or $R^2$ is each independently selected from one or more of the group consisting of hydrogen, deuterium, hydroxyl, halogen, cyano, carboxyl, $C_{1-5}$ alkyl, substituted $C_{1-5}$ alkyl, $C_{1-5}$ alkoxy, substituted $C_{1-5}$ alkoxy, $C_{1-3}$ alkylthio and substituted $C_{1-3}$ alkylthio;
 $R^3$ or $R^4$ is each independently selected from the group consisting of hydrogen, deuterium, hydroxyl, amino, substituted amino, nitro, halogen, cyano, carboxyl, $C_{1-5}$ alkyl, substituted $C_{1-5}$ alkyl, $C_{1-3}$ alkoxy and substituted $C_{1-3}$ alkoxy, the substituent is selected from one or more of the group consisting of deuterium, hydroxyl, amino, nitro, halogen, cyano, carboxyl, $C_{1-3}$ alkyl and glycosyl;
 $R^5$ is selected from one or more of the group consisting of hydroxyl, halogen, cyano, carboxyl, $C_{1-5}$ alkyl, substituted Cis alkyl, $C_{1-3}$ alkoxy, substituted $C_{1-3}$ alkoxy, $C_{1-3}$ alkylthio and substituted $C_{1-3}$ alkylthio;
 $R^6$ is selected from one or more of the group consisting of hydrogen, deuterium, hydroxyl, halogen, cyano, amino, substituted amino, carboxyl, Cis alkyl, substituted Cis alkyl, $C_{1-3}$ alkoxy and substituted $C_{1-3}$ alkoxy, the substituent is selected from one or more of the group consisting of deuterium, hydroxyl, amino, nitro, halogen, cyano, carboxyl and $C_{1-3}$ alkyl;
 $R^7$ or $R^8$ is each independently selected from the group consisting of hydrogen, deuterium, hydroxyl, halogen, amino, substituted amino, nitro, cyano, $C_{1-3}$ alkyl, substituted $C_{1-3}$ alkyl, $C_{1-3}$ alkoxy and substituted $C_{1-3}$ alkoxy, the substituent is selected from one or more of the group consisting of deuterium, hydroxyl, amino, nitro, halogen and cyano;
 m, n or q is 0, 1, 2 or 3;
 the substituents in $R^1$, $R^2$ or $R^5$ are each independently selected from one or more of the group consisting of deuterium, hydroxyl, amino, nitro, halogen, cyano, carboxyl and glycosyl; and
ii) p is 0, m is 1, n is 1:
 $R^1$ or $R^2$ is each independently selected from one or more of the group consisting of hydrogen, deuterium, hydroxyl, halogen, cyano, carboxyl, $C_{1-5}$ alkyl, substituted $C_{1-5}$ alkyl, $C_{1-5}$ alkoxy, substituted $C_{1-5}$ alkoxy, $C_{1-3}$ alkylthio and substituted $C_{1-3}$ alkylthio;
 $R^3$ is selected from the group consisting of amino, substituted amino, nitro, halogen, cyano, carboxyl, $C_{1-5}$ alkyl, substituted $C_{1-5}$ alkyl, $C_{1-3}$ alkoxy and substituted $C_{1-3}$ alkoxy, the substituent is selected from one or more of the group consisting of deuterium, hydroxyl, amino, nitro, halogen, cyano, carboxyl, $C_{1-3}$ alkyl and glycosyl;
 $R^4$ is selected from the group consisting of hydrogen, amino, substituted amino, nitro, halogen, cyano, carboxyl, $C_{1-5}$ alkyl, substituted $C_{1-5}$ alkyl, $C_{1-3}$ alkoxy and substituted $C_{1-3}$ alkoxy, the substituent is selected from one or more of the group consisting of deuterium, hydroxyl, amino, nitro, halogen, cyano, carboxyl, $C_{1-3}$ alkyl and glycosyl;
 $R^5$ is selected from one or more of the group consisting of hydrogen, deuterium, hydroxyl, halogen, cyano, carboxyl, $C_{1-5}$ alkyl, substituted $C_{1-5}$ alkyl, $C_{1-3}$ alkoxy, substituted $C_{1-3}$ alkoxy, $C_{1-3}$ alkylthio and substituted $C_{1-3}$ alkylthio;
 $R^6$ is selected from one or more of the group consisting of hydrogen, deuterium, hydroxyl, halogen, cyano, amino, substituted amino, carboxyl, $C_{1-5}$ alkyl, substituted $C_{1-5}$ alkyl, $C_{1-3}$ alkoxy and substituted $C_{1-3}$ alkoxy, the substituent is selected from one or more of the group consisting of deuterium, hydroxyl, amino, nitro, halogen, cyano, carboxyl and $C_{1-3}$ alkyl;
 $R^7$ or $R^8$ is each independently selected from the group consisting of hydrogen, deuterium, hydroxyl, halogen, amino, substituted amino, nitro, cyano, $C_{1-3}$ alkyl, substituted $C_{1-3}$ alkyl, $C_{1-3}$ alkoxy and substituted $C_{1-3}$ alkoxy, the substituent is selected from one or more of the group consisting of deuterium, hydroxyl, amino, nitro, halogen and cyano;
 q is 0, 1, 2 or 3;
 the substituents in $R^1$, $R^2$ or $R^5$ are each independently selected from one or more of the group consisting of deuterium, hydroxyl, amino, nitro, halogen, cyano, carboxyl and glycosyl.

2. The compound according to claim 1, wherein,
 $R^1$ or $R^2$ is each independently selected from one or more of the group consisting of hydroxyl, fluorine, chlorine, cyano, $C_{1-3}$ alkyl, substituted $C_{1-3}$ alkyl, $C_{1-2}$ alkoxy and substituted $C_{1-2}$ alkoxy, and the substituent is selected from one or more of the group consisting of deuterium, hydroxyl, amino, nitro, fluorine, chlorine, cyano and carboxyl.

3. The compound according to claim 1, wherein,
 $R^3$ is selected from the group consisting of deuterium, hydroxyl, amino, $C_{1-3}$ alkyl and $C_{1-3}$ alkoxy;
 $R^4$ is selected from the group consisting of hydrogen, deuterium, hydroxyl, amino, $C_{1-3}$ alkyl and $C_{1-3}$ alkoxy.

4. The compound according to claim 1, wherein,
 $R^5$ is selected from one or more of the group consisting of hydroxyl, halogen, cyano and $C_{1-2}$ alkoxy;
 $R^6$ is selected from the group consisting of hydrogen, deuterium, hydroxyl, amino, $C_{1-3}$ alkyl, substituted $C_{1-5}$ alkyl, $C_{1-3}$ alkoxy and substituted $C_{1-3}$ alkoxy, and the substituent is selected from one or more of the group consisting of deuterium, hydroxyl, amino, fluorine, carboxyl and cyano.

5. The compound according to claim 1, wherein,
$R^7$ or $R^8$ is each independently selected from the group consisting of hydrogen, deuterium, hydroxyl, $C_{1-3}$ alkoxy and substituted $C_{1-3}$ alkoxy, and the substituent is selected from one or more of the group consisting of deuterium, hydroxyl, amino and halogen.

6. The compound according to claim 1, wherein,
$R^1$ or $R^2$ is each independently selected from the group consisting of hydroxyl, halogen, cyano, $C_{1-3}$ alkyl, $C_{1-3}$ alkoxy, and substituted $C_{1-2}$alkoxy, and the substituent is selected from the group consisting of deuterium, hydroxyl, amino, fluorine and carboxyl;
$R^3$ is selected from the group consisting of hydroxyl, amino, $C_{1-3}$ alkyl, substituted $C_{1-5}$ alkyl, $C_{1-3}$ alkoxy and substituted $C_{1-3}$ alkoxy, and the substituent is selected from the group consisting of deuterium, hydroxyl, amino, fluorine and carboxyl;
$R^4$ is selected from the group consisting of hydroxyl, amino, $C_{1-3}$ alkyl, substituted $C_{1-5}$ alkyl, $C_{1-3}$ alkoxy and substituted $C_{1-3}$ alkoxy, and the substituent is selected from the group consisting of deuterium, hydroxyl, amino, fluorine and carboxyl;
$R^5$ is selected from hydroxyl, halogen, cyano, $C_{1-2}$alkoxy and substituted $C_{1-3}$ alkoxy, and the substituent is selected from the group consisting of deuterium, hydroxyl, fluorine and carboxyl;
$R^6$ is selected from one or more of the group consisting of hydrogen, deuterium, hydroxyl, cyano, amino, $C_{1-3}$ alkyl, substituted $C_{1-3}$ alkyl, $C_{1-3}$ alkoxy and substituted $C_{1-3}$ alkoxy, and the substituent is selected from the group consisting of deuterium, hydroxyl, amino, fluorine and carboxyl; p or q is each independently 0, 1 or 2;
$R^7$ or $R^8$ is each independently selected from one or more of the group consisting of hydrogen, hydroxyl, cyano, $C_{1-3}$ alkyl, substituted $C_{1-3}$ alkyl, $C_{1-3}$ alkoxy and substituted $C_{1-3}$ alkoxy, and the substituent is selected from one or more of the group consisting of deuterium, hydroxyl, amino and fluorine.

7. The compound according to claim 1, wherein, the compound is selected from the group consisting of
2-{8-hydroxy-3-(4-hydroxy-3-methoxyphenyl)-2-hydroxymethyl-2,3-dihydrobenzo[b][1,4]dioxan yl}chroman-3,4,5,7-tetraol;
(2R,3S)-2-{(2R,3R)-3-(4-hydroxy-3-methoxyphenyl)-2-hydroxymethyl-2,3-dihydrobenzo[b][1,4]dioxan-6-yl}chroman-3,4,5,7-tetraol;
2-{8-hydroxy-3-(4-hydroxy-3-methoxyphenyl)-2-hydroxymethyl-2,3-dihydrobenzo[b][1,4]dioxan yl}chroman-3,5,7-triol;
(2R,3S)-4-amino-2-{(2R,3R)-3-(4-hydroxy-3-methoxyphenyl)-2-hydroxymethyl-2,3-dihydrobenzo[b][1,4]dioxan-6-yl}chroman-3,5,7-triol;
(2R,3S)-2-{(2R,3R)-2-hydroxymethyl-3-[3-methoxy-4-(trideuteromethoxy)phenyl]-2,3-dihydrobenzo[b][1,4]dioxan-6-yl}-5,7-bis(trideuteromethoxy)chroman-3-ol;
2-{8-hydroxy-3-(4-hydroxy-3-methoxyphenyl)-2-hydroxymethyl-2,3-dihydrobenzo[b][1,4]dioxan-6-yl}-7-methoxy-chroman-3,4,5-triol;
2-{8-hydroxy-3-(4-hydroxy-3-methoxyphenyl)-2-hydroxymethyl-2,3-dihydrobenzo[b][1,4]dioxan-6-yl}-7-methoxychroman-3,5-diol;
7-{(3-hydroxy-5,7-dimethoxychroman-2-yl)-2-(4-hydroxy-3-methoxyphenyl)-3-hydroxymethyl-2,3-dihydrobenzo[b][1,4]dioxane}-5-ol;
2-{8-hydroxy-3-(4-hydroxy-3-methoxyphenyl)-2-hydroxymethyl-2,3-dihydrobenzo[b][1,4]dioxan-6-yl}-5-methoxychroman-3,7-diol;
2-{8-hydroxy-3-(4-hydroxy-3-methoxyphenyl)-2-hydroxymethyl-2,3-dihydrobenzo[b][1,4]dioxan-6-yl}-5,7-dimethoxychroman-3,4-diol;
7-fluoro-2-{8-hydroxy-3-(4-hydroxy-3-methoxyphenyl)-2-hydroxymethyl-2,3-dihydrobenzo[b][1,4]dioxan-6-yl}chroman-3,4,5-triol;
7-ethoxy-2-{8-hydroxy-3-(4-hydroxy-3-methoxyphenyl)-2-hydroxymethyl-2,3-dihydrobenzo[b][1,4]dioxan-6-yl}chroman-3,5-diol;
5-ethoxy-2-{8-hydroxy-3-(4-hydroxy-3-methoxyphenyl)-2-hydroxymethyl-2,3-dihydrobenzo[b][1,4]dioxan-6-yl}chroman-3,7-diol;
2-{8-bromo-3-(4-hydroxy-3-methoxyphenyl)-2-hydroxymethyl-2,3-dihydrobenzo[b][1,4]dioxan yl}chroman-3,4,5,7-tetraol;
2-{8-bromo-3-(4-hydroxy-3-methoxyphenyl)-2-hydroxymethyl-2,3-dihydrobenzo[b][1,4]dioxan yl}chroman-3,5,7-triol;
2-(4-hydroxy-3-methoxyphenyl)-3-hydroxymethyl-7-(3,5,7-trihydroxychroman-2-yl)-2,3-dihydrobenzo[b][1,4]dioxan-5-carbonitrile;
2-{8-hydroxy-3-(4-hydroxy-3-methoxyphenyl)-2-hydroxymethyl-2,3-dihydrobenzo[b][1,4]dioxan-6-yl}chroman-3,4,6,7-tetraol; and
2-{8-hydroxy-3-(4-hydroxy-3-methoxyphenyl)-2-hydroxymethyl-2,3-dihydrobenzo[b][1,4]dioxan-6-yl}chroman-3,6,7-triol.

8. A pharmaceutical composition, using the compound, optical isomers or pharmaceutically acceptable salts thereof according to claim 1 as active ingredients or main active ingredients, supplemented by pharmaceutically acceptable excipients.

* * * * *